US008367859B2

(12) United States Patent
Frost et al.

(10) Patent No.: US 8,367,859 B2
(45) Date of Patent: Feb. 5, 2013

(54) CYCLOHEXANE 1,4 CARBOXYLATES

(75) Inventors: John W. Frost, Okemos, MI (US);
Adeline Miermont, Toledo, OH (US);
Dirk Schweitzer, Okemos, MI (US); Vu Bui, Davis, CA (US); Douglas A. Wicks, Minneapolis, MN (US)

(73) Assignee: Amyris, Inc., Emeryvillle, CA (US)

( * ) Notice: Subject to any disclaimer, the term of this patent is extended or adjusted under 35 U.S.C. 154(b) by 169 days.

(21) Appl. No.: 12/816,742

(22) Filed: Jun. 16, 2010

(65) Prior Publication Data
US 2011/0288310 A1 Nov. 24, 2011

Related U.S. Application Data

(60) Provisional application No. 61/187,444, filed on Jun. 16, 2009.

(51) Int. Cl.
C07C 69/75 (2006.01)
C07C 61/09 (2006.01)
(52) U.S. Cl. ........................ 560/127; 562/509
(58) Field of Classification Search .................. 560/127;
562/509
See application file for complete search history.

(56) References Cited

U.S. PATENT DOCUMENTS

| | | | |
|---|---|---|---|
| 3,671,572 A | 6/1972 | Driscoll | |
| 3,733,309 A | 5/1973 | Wyeth et al. | |
| 3,940,431 A | 2/1976 | Wulf et al. | |
| 4,024,173 A | 5/1977 | Lenz et al. | |
| 4,028,307 A | 6/1977 | Ure | |
| 4,074,062 A | 2/1978 | Murakami et al. | |
| 4,138,580 A | 2/1979 | Umemira et al. | |
| 4,234,740 A | 11/1980 | Umemura et al. | |
| 4,255,588 A | 3/1981 | Hillman | |
| 4,260,810 A | 4/1981 | Umemira et al. | |
| 4,392,001 A | 7/1983 | Don et al. | |
| 4,588,688 A | 5/1986 | Maxwell | |
| 4,657,863 A * | 4/1987 | Maxwell et al. ............... | 435/142 |
| 4,661,558 A | 4/1987 | Bell et al. | |
| 5,021,173 A | 6/1991 | Waddoups et al. | |
| 5,145,987 A | 9/1992 | Molzahn et al. | |
| 5,320,765 A | 6/1994 | Fetterman, Jr. et al. | |
| 5,412,108 A | 5/1995 | Fisher et al. | |
| 5,420,227 A | 5/1995 | Pfeil et al. | |
| 5,476,933 A | 12/1995 | Keana et al. | |
| 5,487,987 A | 1/1996 | Frost et al. | |
| 5,616,496 A | 4/1997 | Frost et al. | |
| 5,705,723 A | 1/1998 | Kallenbach et al. | |
| 6,171,797 B1 | 1/2001 | Perbost | |
| 6,307,099 B1 | 10/2001 | Turner et al. | |
| 6,323,373 B1 | 11/2001 | Spreitzer et al. | |
| 6,355,817 B1 | 3/2002 | Woods et al. | |
| 6,392,088 B1 | 5/2002 | Bertola et al. | |
| 6,610,215 B1 | 8/2003 | Cai et al. | |
| 6,646,155 B2 | 11/2003 | Herzog et al. | |
| 6,916,950 B2 | 7/2005 | Gubisch et al. | |
| 7,208,545 B1 | 4/2007 | Brunner et al. | |
| 7,271,282 B1 | 9/2007 | Kawahara et al. | |
| 7,282,601 B2 | 10/2007 | Kawahara et al. | |
| 7,309,754 B2 | 12/2007 | Brock et al. | |
| 7,319,161 B2 | 1/2008 | Noe et al. | |
| 2002/0026070 A1 | 2/2002 | Bertola et al. | |
| 2004/0054220 A1 | 3/2004 | Noe et al. | |
| 2005/0038283 A1 | 2/2005 | Kawahara et al. | |
| 2005/0067373 A1 | 3/2005 | Brock et al. | |
| 2007/0129565 A1 | 6/2007 | Sutton et al. | |
| 2007/0208160 A1 | 9/2007 | Agarwal et al. | |
| 2009/0017240 A1 | 1/2009 | Charbonnel et al. | |
| 2009/0099368 A1 | 4/2009 | Kotrel et al. | |
| 2009/0105377 A1 | 4/2009 | Vijayendran et al. | |
| 2009/0124829 A1 | 5/2009 | Gong | |
| 2009/0171037 A1 | 7/2009 | Aoshima et al. | |
| 2009/0246430 A1 | 10/2009 | Kriegel et al. | |
| 2009/0299109 A1 | 12/2009 | Gruber et al. | |
| 2009/0312470 A1 | 12/2009 | Bradshaw et al. | |
| 2010/0168371 A1 | 7/2010 | Berti et al. | |
| 2010/0168372 A1 | 7/2010 | Berti et al. | |
| 2010/0168373 A1 | 7/2010 | Berti et al. | |
| 2010/0168461 A1 | 7/2010 | Berti et al. | |
| 2010/0314243 A1 | 12/2010 | Frost et al. | |
| 2011/0282078 A1 | 11/2011 | Frost et al. | |
| 2011/0288263 A1 | 11/2011 | Frost et al. | |
| 2011/0288311 A1 | 11/2011 | Frost et al. | |

FOREIGN PATENT DOCUMENTS

| | | |
|---|---|---|
| DE | 5 261 68 C | 6/1931 |
| DE | 10 2007 055242 A1 | 5/2009 |
| EP | 0 522 839 A2 | 1/1993 |
| EP | 0 450 512 B1 | 1/1995 |
| EP | 1 347 005 A1 | 9/2003 |
| EP | 0 971 870 B1 | 10/2003 |
| EP | 1 386 937 A1 | 2/2004 |
| EP | 1 683 819 A1 | 7/2006 |
| EP | 1 736 497 A1 | 12/2006 |
| EP | 1 842 868 A1 | 10/2007 |
| EP | 1 882 712 A1 | 1/2008 |
| GB | 1 021 520 A | 3/1966 |
| GB | 1 022 870 A | 3/1966 |
| WO | 96/15112 | 5/1996 |

(Continued)

OTHER PUBLICATIONS

Translation of Achmatowicz, 1958, Roczniki Chemii Annales Societatis Chimicae Polonorum, vol. 32, p. 499-511.*

(Continued)

*Primary Examiner* — Golam M M Shameem
*Assistant Examiner* — Karen Cheng
(74) *Attorney, Agent, or Firm* — Jennifer A. Camacho; Fang Xie

(57) ABSTRACT

The present invention relates to cyclohexanes having carboxylate derivatives at the 1 and 4, and optionally the 2, position. The invention also relates to processes for preparing such compounds wherein a portion of the starting materials utililzed is derived from renewable resources.

19 Claims, 3 Drawing Sheets

FOREIGN PATENT DOCUMENTS

| | | |
|---|---|---|
| WO | 97/32913 | 9/1997 |
| WO | 98/38150 A1 | 9/1998 |
| WO | 99/40049 | 8/1999 |
| WO | 2009/064515 A1 | 5/2009 |
| WO | 2009/120457 A3 | 10/2009 |
| WO | 2010/078328 | 7/2010 |

OTHER PUBLICATIONS

Carbon-14, Human Health Fact Sheet from Argonne National Laboratory, 2005.*

Isoda, 1979, Chem. Pharm. Bull, vol. 27, p. 2735-2742.*

Mar. 1992, Advanced Organic Chemistry, John Wiley & Sons, 4th Edition, p. 1212 and 1214.*

Jackson, S. David, "Metal Catalysed Hydrogenation" available at http://www.chem.gla.ac.uk/staff/sdj/mch.html accessed Apr. 22, 2009.

Achmatowicz et al., *The Application of Muconic Ester to Diene Additions*, 3 Bulletin de l'Academie Polonaise des Sciences 557-564 (1955).

Jerry March, Advanced Organic Chemistry Reactions Mechanisms, and Structure 1073-1074 (Robert H. Summersgill and Anne T. Vinnicombe eds., McGraw-Hill, Inc. 1977) (1968).

Farmer et al., *Properties of Conjucated Compounds*, J. Chemical Society 897-909 (1929).

Alder et. al., *Über den sterischen Verlauf von Dien-Synthesen mit acyclischen Dienen*, 571 Justua Lieb. Ann. Chem. 153-157 (1950).

Niu et. al., *Benzene-Free Synthesis of Adipic Acid*, 18 Michigan State University, Department of Chemistry, Biotechnological Program 201-211 (2002).

International Search Report and Written Opinion for Corresponding PCT Application No. US2010/038811 filed Jun. 16, 2010 and Published on Dec. 23, 2010 as WO 2010/148080 A2 mailed Aug. 18, 2011.

Copending U.S. Appl. No. 12/816,600, filed Jun. 16, 2010.

Copending U.S. Appl. No. 12/816,763, filed Jun. 16, 2010.

Copending U.S. Appl. No. 12/816,701, filed Jun. 16, 2010.

Achatowicz et al., *O Przydatnosci Estru Mukonowego do Syntez Dienowych. I. Kodensacja Estru Mukonowego z Cyjamkiem Winylu, Akroleina I Styrenem*, Roczniki Chemi I Annales Societatis Chimicae Pokonorum, Jan. 1, 1958, 499-505, 32.

Alder et al., *Darstellung und Sterochemie Der 1.2.3.4-Tetracarbonsäuren Des Cyclopentans Und Cyclohexans*, Justus Liebigs Annalen Der Chemie, Jan. 27, 1958, 7-32, 611, 1.

Anzalone et al., *Substituent Effects on Hydrogenation of Aromatic Rings: Hydrogenation vs. Hydrogenolysis in Cyclic Analogous of Benzyl Ethers*, Journal of Organic Chemistry, Jan. 1, 1958, 50, 1.

Avram et al., *Investigation in the cyclobutane series. X: Some reactions of dibenzotricyclo-octadiene and of dibenzocyclo-octatetraene*, Tetrahedron, 1963, 309-317, 19, 2.

Bachmann et al., *The Diels—Alder Reaction of 1-Vinylapthalene with alpha,beta- and, beta, gamma, delta-Unsaturated Acids and Derivatives*, Journal of the American Chemical Society, Sep. 1, 1949, 3062-3072, 71, 9.

Baeyer, *Über Die Constitution Des Benzols*, Justus Liebigs Annalen Der Chemie, 1888, 103-190, 245.

Bolchi et al., *Peptidomimetic inhibitors of farnesyltransferase with high in vitro activity and significant cellular potency*, Bioorganic & Medical Chemistry Letters, Oct. 12, 2007, 6192-6196, 17, 22.

Burdett, *An Improved Acid Chloride Preparation via Phase Transfer Catalysis*, Synthesis, Jun. 1991, 441-442, 6.

Chang et al., *Synthesis and binding properties of a macrocycle with two binding subcavities*, Tetrahedron Letters, Jun. 19, 2006, 4141-4144, 47, 25.

Cook et al., *Conformation analysis of substituted 1,2-dihyronaphthalenes*, Journal of The Chemical Society, Jan. 1, 1972, 1901-1905.

Deno, *The Diels-Alder Reaction with alpha,beta, gamma,delta-Unsaturated Acids*, Journal of the American Chemical Society, Sep. 1, 1950, 4057-4059, 72, 9.

Dewar et al., *Factors influencing the Stabilities of nematic liquid crystals*, Journal of the American Chemical Society, Nov. 1975, 6658-6662, 97, 23.

Elvidge et al., *The third isomeric (cis-trans-) muconic acid*, Journal of Chemistry Society (Resumed), 1950, 2235-2241.

Ferguson et al., *Selective Oxidation of Alkyl Groups*, Journal of Organic Chemistry, Apr. 1960, 668-670, 25.

Gajewski et al., *Deuterium kinetic isotope effects in the 1,4-dimethylenecyclohexane boat Cope rearrangement*. Journal of the American Chemical Society, Feb. 1986, 108,3.

Grundmann, *Zur Kenntnis der Oxydation von Phenolen mit Peressigsäure*, Berichte Der Deutschen Chemischen Gesellschaft, Jul. 8, 1936, 1755-1757, 69, 7.

Hörhammer et al., *Terephthalsäuredimethylester in den Blüten von Sarothamnus scoparius L.*, Naturwissenschaften, 1966, 584, 53.

Kaufmann et al., *Diels-Alder-Reaktionen auf dem Fettgebiet VIII Die Reaktion von Polyenfettsäuren und trocknenden Ölen mit Acetylen; eine neue Synthese der Terephthalsaure*, Fette, Sceifen, Anstrichmittel, 1963, 856-858, 65, 10.

Khan et al., *Cotonoates A and B, New Aromatic Esters from Cotoneaster racemiflora*, Zeitschrift für Naturforschung B (Chemical Sciences), 2008, 1219-1222, 63b.

Korver et al., *The diels-alder reaction of styrene with trans-penta-1,3-diene: Methyl 2-trans,4-pentadienoate, and dimethyl 2-trans, 4-trans-hexadienedioate*, Tetrahedron, 1969, 4109-4115, 25, 17.

Koshel et al., *Liquid-phase Catalytic Oxidation of 2,5-Dimethylbiphenyl*, Russian Journal of Organic Chemistry, Jan. 1, 2001, 877-880, 37, 6.

Lyszczek, *Thermal and spectroscopic investigations of new lanthanide complexes with 1,2,4-benzenetricarboxylic acid*, Journal of Thermal Analysis and Calorimetry, Apr. 29, 2007, 533-539, 90, 2.

Lee et al., *Photochemistry of bicycle [2.2.2.]octenones: an uncommon oxidative decarbonylation*, Chemical Communication, 1999, 801-802, 1999, 9.

Freund et al., *Synthese von Indandionen*, Justus Liebigs Annalen Der Chemie, 1916, 14-38, 411, 1.

McMillan et al., *Hexamethylene-I,6-bis-t-amines in which Part of the Six Carbon Chain is also Part of the Six-member Ring*, Journal of the American Chemical Society, Aug. 1956, 78, 16.

Meshram et al., *Zinc Promoted Convenient and General Synthesis of Thiol Esters*, Synlett, Aug. 1, 1998, 877-878.

Morrison, *A Synthesis of Flurene-3-carboxylic Acid*, The Journal of Organic Chemistry, Sep. 1958, 23, 9.

Reddy et al., *Chemical Examination of Pods of Cassia roxburghii*, Journal of the Indian Chemical Society, 1990, 783-784, 67.

Reggel et al., *The Lithium-Ethylenediamine System. II. Isomerization of Olefins and Dehydrogenation of Cyclic Diens*, Journal of Organic Chemistry, Aug. 1958, 1136-1139, 23.

Roll et al., *Proton magnetic resonance spectra and stereochemistry of some 5,6-disubstituted bicycle[2.2.2]oct-2-enes*, Journal of Pharmaceutical Sciences, Aug. 1965, 1110-1117, 54, 8.

Shimasaki et al., *Retinoidal Dienamides and Related Aromatic Amides. Replacement of the 9-ene Structure of Retinoic Acid with a Trans- or Cis-Amide Group*, Chemical and Pharmaceutical Bulletin, Jan. 1, 1995, 100-107, 43, 1.

Sih et al., *The naphthalene route to anthracyclinones*, Tetrahedron Letters, 1979, 1285-1288, 20-15.

Talapatra et al., *On the Chemistry of Indian Orchidaceae Plants-II*, Tetrahedron, 1985, 2765-2769, 41.

Talapatra et al., *Polyphenolic Constituents of Magnolia pterocarpa Roxb*, Journal of Indian Chemical Society, 1983, 96-98, 60.

Thakur et al., *Terephthalic Acid and its Methyl Esters from Zizyphus sativa*, Planta Medica, Oct. 1975, 172-173, 28.

Widman et al., *Über die Oxydation des Cymols und das sogenannte Nitrocymol*, Berichte der Deutschen Chemischen Gesellschaft (European Journal for Inorganic Chemistry), 1886, 583-589, 19.

Wintersteiner et al., *Degradation of Veratramine to Benzene-1,2,3,4-tetracarboxylic Acid*, Journal of American Chemical Society, Jun. 1953, 2781-2782, 75, 11.

Yagupol'Skii, et al., *Fluorination of aromatic carboxylic acids by sulfur tetrafluoride*, Journal of Organic Chemistry USSR, (English Translation), 1973, 710-716, 9.

Zuercher et al., *Tandem ring opening-ring closing metathesis of cyclic olefins*, Journal of the American Chemical Society, Jan. 1, 1996, 6634-6640, 118, 28.

Alder, et al., "Presentation and Stereochemistry of the 1.2.3.4. Tetracarboxylic Acids of Cyclopentane and Cyclohexane", Justus Liebigs Annalen der Chemie, 1958, pp. 7-32.

Kaufmann et al., "Diels-Alder Reactions in the Field of Fats VIII: The Reaction of Polyene Fatty Acids and Drying Oils with Acetylene: A New Synthesis of Terephthalic Acid", Fette, Seifen, Anstrichmittel, 1963, pp. 856-858.

* cited by examiner

US 8,367,859 B2

CYCLOHEXANE 1,4 CARBOXYLATES

CROSS-REFERENCE TO RELATED APPLICATIONS

This application claims priority from U.S. Provisional Application Ser. No. 61/187,444 filed Jun. 16, 2009 titled "NOVEL TEREPHTHALIC AND TRIMELLITIC BASED ACIDS AND CARBOXYLATE DERIVATIVES THEREOF" incorporated herein by reference.

FIELD OF INVENTION

The present invention relates to novel benzene 1,4-dicarboxylate compounds (terephthalic acid and carboxylate derivatives thereof) and products prepared therefrom having a significant renewable content. The invention also relates to processes for preparing benzene 1,4-dicarboxylate compounds (terephthalic and carboxylate derivatives thereof) wherein a portion of the starting materials utililzed is derived from renewable resources. The invention also relates to novel cyclohexene 1,4-dicarboxylate based intermediates prepared in these processes and to conversion of these intermediates to substituted and unsubstituted cyclohexane 1,4-dicarboxylates and derivatives thereof. The invention also relates to products prepared from such compounds derived from starting materials themselves derived from renewable resources.

BACKGROUND OF THE INVENTION

Terephthalic acid and trimellitic acids comprise a benzene ring with carboxylate groups at the 1,4 and the 1,2,4 positions respectively. These acids and their carboxylate derivatives are useful in a variety of commercial products such as polyesters and plasticizers. At the present time these acids and their carboxylate derivatives are synthesized commercially from petroleum based starting materials, such as p-xylene. Due to volatility in hydrocarbon markets and the limited amount of hydrocarbons available for future use it is desirable that methods of preparing such important compounds from renewable resources be developed.

Some large agricultural crops such as corn and sugar cane and the by-products associated with their harvesting and processing which cannot be used as a food source contain starch or cellulosic materials which can be broken down to simple sugars which can then be converted to useful products. See, for instance, Frost et. al. U.S. Pat. No. 5,629,181; Frost U.S. Pat. No. 5,168,056; Frost et. al. U.S. Pat. No. 5,272,073; Frost U.S. Patent publication 2007/0178571, and Frost et. al. U.S. Pat. No. 5,616,496, incorporated herein by reference.

There is a need for substituted and unsubstituted benzene 1,4-dicarboxylate compounds (terephthalic acid and carboxylate derivatives thereof) and processes for preparing such compounds from starting materials that can be made or derived from renewable resources, such as, for example, biomass or simple sugars which can then be derived from biomass.

SUMMARY OF THE INVENTION

The present invention provides a method for preparing compounds containing at least one benzene ring and carboxylate derivatives at the 1 and 4 positions of the benzene ring, and optionally at the 2 position of the benzene ring. Such compounds include substituted and unsubstituted terephthalic acid and carboxylate derivatives thereof. Substituted terephthalates include compounds having a benzene ring with carboxylic acid groups or carboxylate derivatives thereof at the 1 and 4 position wherein the benzene ring may be substituted on other carbons. In one preferred embodiment, the benzene ring is substituted at the 2 position. One preferred subsituent at the 2 position is a carboxylic acid or carboxylate derivative thereof. Another preferred group of substituents comprise a phenyl, an alkyl or a halogen group. Included in more preferred substituted terephthalates are trimellitic acid and phenylterephthalic acid. As used herein, the term carboxylate refers to any group which contains a carbonyl group ($C=O$) wherein the carbonyl group is bonded to an anion so as to form a salt, to a heteroatom, such as oxygen, nitrogen, sulfur or one or more halogens. The heteroatom may be further bonded by a covalent bond to one or more other groups, such as hydrogen or hydrocarbyl groups which may optionally contain one or more heteroatoms, or may be electronically bonded to a cation to form a salt. Alternatively, the carboxylate derivative can be a nitrile. Preferably, the carboxylate is an acyl halide, carboxylic acid, amide, ester, thiol ester, mercaptocarbonyl, anhydride, nitrite, salt with an anion or salt with a cation. Preferred cations include alkali metals and unsubstituted and hydrocarbyl substituted ammonium ions. The term carboxylate as used herein includes the carboxylic acid form of carboxylate derivatives. The term carboxylic acid or acid is used herein in contexts wherein the acid form is distinguished from other carboxylate forms. The particular use hereinafter is clear from the context. The method comprises: contacting one or more muconic acid dienes or carboxylate derivatives thereof with one or more dienophiles under conditions such that the one or more muconic acids or carboxylate derivatives thereof and one or more dienophiles form one or more cyclohexene ring containing compounds; and contacting the cyclohexene ring containing compounds with one or more dehydrogenation catalysts, optionally in the presence of one or more oxidants, under conditions such that compounds containing an aromatic ring with carboxylate derivatives at the 1 and 4 position, and optionally the 2 position, are prepared. Where there are carboxylate derivatives at the 1 and 4 position, the compounds are referred to herein as terephthalic acid or carboxylate derivatives thereof. Where the final compounds additionally contain a carboxylate at the 2 position of the aromatic ring in addition to the carboxylate derivatives at the 1 and 4 positions, the compounds are referred to herein as a trimellitic acids or carboxylate derivatives thereof. In a preferred embodiment, the carboxylate derivatives are esters of the carboxylic acids, preferably hydrocarbyl carboxylates. The one or more muconic acids, or carboxylate derivatives thereof, and the one or more dienophiles may be contacted neat or in the presence of a solvent. In another preferred embodiment, the one or more muconic acids or carboxylate derivatives thereof are contacted with one or more dienophiles at a temperature of about 130° C. to about 170° C. In yet another embodiment, the one or more muconic acids or carboxylate derivatives thereof and the one or more dienophiles are contacted in the presence of one or more compounds which inhibit the polymerization of compounds containing unsaturated groups. In yet another embodiment, the one or more muconic acids or carboxylate derivatives thereof and the one or more dienophiles are contacted in the presence of a Diels-Alder cycloaddition catalyst (Lewis acid). In yet another embodiment, the one or more muconic acids or carboxylate derivatives thereof and the one or more dienophiles are contacted in the presence of a isomerization catalyst, which interconverts the different muconic acids or carboxylate derivatives thereof to the trans,trans isomer.

Preferably, the one or more muconic acids, or carboxylate derivatives thereof, reacted with the dienophile are in the trans,trans isomeric arrangement. In a preferred embodiment, the starting muconic acid is cis,cis muconic acid prepared by microbial synthesis. The product of known microbial synthesis is the cis,cis muconic acid isomer. Preferably, the muconic acid or the carboxylate derivatives used in the process of reacting one or more muconic acids or carboxylate esters thereof with one or more dienophiles are prepared by isomerization of cis,cis muconic acid or cis,trans muconic acid. In a preferred embodiment, the one or more muconic acids or carboxylate derivatives thereof are prepared from one or more of cis,trans and cis,cis muconic acid or carboxylate derivatives thereof by contacting one or more of cis,cis and cis,trans muconic acid or carboxylate derivatives thereof with one or more isomerization catalysts, ultraviolet radiation sources or both, in a solvent under conditions such that the cis,cis and/or cis,trans muconic acid or carboxylate derivatives thereof isomerize to the trans,trans muconic acid or carboxylate derivatives thereof. In another preferred embodiment, the cis,cis muconic acid is convened to trans,trans muconic acid by the process comprising: a) exposing cis,cis muconic acid in water to elevated temperatures, above room temperature (about 23° C.) to form cis,trans muconic acid; b) cooling the muconic acid in water to a temperature at which the cis,trans isomer precipitates from water; c) recovering the cis,trans muconic acid; and d) contacting the cis,trans muconic acid and one or more isomerization catalysts, ultraviolet radiation sources or both, under conditions such that the cis,trans muconic acid isomerizes to trans,trans muconic acid.

In one preferred embodiment, an ester form of muconic acid is reacted with one or more dienophiles. Preferably, the ester is in the trans,trans isomeric form. The sequence of isomerization and esterification of muconic acid is not critical. Thus, the esterified form of muconic acid may be subjected to isomerization after esterification. Preferably, muconic acid is isomerized to the trans,trans isomer before being esterified. The esterification step can be performed by contacting one or more muconic acids with one or more esterifying agents under conditions that one or more dihydrocarbyl muconates are formed. The one or more esterifying agents can be any compounds which are capable, under reasonable reaction conditions, of replacing the hydrogens on the carboxylic acids located on the one or more muconic acids with hydrocarbyl groups wherein the resulting esters are capable of reacting with the dienophiles as described hereinbefore. Preferred esterification agents are hydrocarbon based compounds containing hydroxyl groups. More preferred esterifying agents include alkanols, benzyl alcohol or phenol. In one preferred embodiment, the trans,trans esters of muconic acid are prepared by a) contacting cis,cis muconic acid and one or more isomerization catalysts, ultraviolet radiation sources, or both, in a solvent under conditions such that the cis,cis muconic acid isomerizes to the trans,trans muconic acid; b) recovering the trans,trans muconic acid; and c) contacting the trans,trans muconic acid with an esterifying agent under conditions that trans,trans dihydrocarbyl muconate is formed. In another embodiment, the one or more esters of muconic acid contacted with the dienophile are prepared by: a) exposing cis,cis muconic acid to elevated temperatures in water; b) cooling the muconic acid in water to a temperature at which the cis,trans isomer precipitates from water; c) recovering the cis,trans muconic acid; and d) contacting the cis,trans muconic acid and one or more isomerization catalysts, ultraviolet radiation sources or both, in a solvent under conditions such that the cis,trans muconic acid isomerizes to the trans,trans muconic acid; c) recovering the trans,trans muconic acid; and f) contacting the trans,trans muconic acid with an esterifying agent in the presence of one or more acids under conditions that trans,trans dihydrocarbyl muconate is formed. In another embodiment, the invention is a method for preparing trans,trans dihydrocarbyl muconate comprising: a) contacting cis,cis muconic acid with an esterifying agent in the presence of an acid under conditions that one or more of cis,cis and cis,trans dihydrocarbyl muconate is formed; b) recovering the one or more of cis,cis and cis,trans dihydrocarbyl muconate; and c) contacting the one or more of cis,cis and cis,trans dihydrocarbyl muconate and one or more isomerization catalysts, ultraviolet radiation sources or both, in a solvent for a period of time such that the cis,cis and cis,trans dihydrocarbyl muconate isomerize to the trans,trans dihydrocarbyl muconate.

In one preferred embodiment, the invention is a method for preparing a substituted or unsubstituted benzene 1,4 dicarboxylate (terephthalic acid or terephthalate carboxylate ester based compound) comprising a) contacting cis,cis muconic acid and iodine in the presence of ultraviolet light in a protic or aprotic solvent at a temperature for a period of time such that the cis,cis muconic acid isomerizes to the trans,trans muconic acid; b) recovering the trans,trans muconic acid; and c) contacting the trans,trans muconic acid with one or more alkanols in the presence of one or more strong acids under conditions that one or more trans,trans dialkyl muconates are formed; d) contacting the one or more dialkyl muconates with one or more dienophiles at a temperature of about 130° C. to about 170° C. under conditions such that the dialkyl muconates and dienophiles form one or more cyclohexene ring containing compounds; and contacting the one or more cyclohexene ring containing compounds with one or more dehydrogenation catalysts, optionally in the presence of one or more oxidants, under conditions such that one or more compounds containing a benzene ring with hydrocarbyl carboxylate esters or carboxylic acid groups at the 1 and 4 position are prepared.

In one embodiment, the isomerization of the one or more dihydrocarbyl esters of muconic acid to the trans,trans isomer can be performed in situ in the same reaction mixture as the reaction of the esters with the dienophiles. In this embodiment, one or more compounds containing a benzene ring with hydrocarbyl carboxylates esters at the 1 and 4 position (one or more terephthalate ester based compounds) are prepared by the process comprising contacting one or more of cis,cis or cis,trans muconic acid esters with one or more dienophiles at elevated temperatures under conditions such that the one or more muconic acid esters and the one or more dienophiles form one or more compounds with a cyclohexene ring having carboxylate ester groups at the 1 and 4 position; and contacting the one or more cyclohexene ring containing compounds with one or more dehydrogenation catalysts, optionally in the presence of one or more oxidants, under conditions such that one or more compounds containing a benzene ring with hydrocarbyl carboxylate esters at the 1 and 4 position are prepared. This process is preferably conducted in a solvent, preferably a nonpolar aprotic solvent. Preferably this reaction is carried out at a temperature of about 130° C. to about 170° C. In one embodiment, the isomerization of the one or more isomers of muconic acid to the trans,trans isomer can be performed in situ in the same reaction mixture as the reaction of the muconic acids with the dienophiles. In this embodiment, one or more compounds containing a benzene ring with hydrocarbyl carboxylates esters at the 1 and 4 position (one or more terephthalate ester based compounds) are prepared by the process comprising contacting one or more of cis,cis or cis,trans muconic acid with one or more dienophiles at elevated temperatures under conditions such that the one or more muconic acid isomers and the one or more dienophiles form one or more compounds with a cyclohexene ring having carboxylic acid groups at the 1 and 4 position; and contacting the one or more cyclohexene ring containing compounds with one or more dehydrogenation catalysts, optionally in the presence of one or more oxidants, under conditions such that one or more compounds containing a benzene ring with carboxylic acids groups at the 1 and 4 position are prepared and/or reacted with an esterifying agent under conditions such that carboxylic acid groups are converted to hydrocarbyl carboxylate groups. The hydrogenation and esterification steps may be performed in either sequence.

In one embodiment, the one or more starting dienophiles is one or more alkene based compounds. In this embodiment, the reaction of the one or more muconic acids, or carboxylate derivatives thereof, with the one or more alkene based compounds comprises contacting one or more muconic acids or carboxylate derivatives thereof with one or more alkene based compounds under conditions such that the one or more muconic acids, or carboxylate derivatives thereof, and the one or more alkene compounds form one or more compounds containing a cyclohexane ring having carboxylate groups at the 1 and 4 position.

In another embodiment, the invention is a method for preparing one or more trimellitate based compounds comprising contacting one or more muconic acids, or carboxylate derivatives thereof, with one or more alkynes, having a carboxylate ester bound to one carbon of the triple bond, under conditions such that the one or more muconic acids, or carboxylate derivatives thereof, and one or more alkynes form one or more trimellitate based acids, or carboxylate derivatives thereof. In this embodiment, an oxidant, such as oxygen, present in the reaction mixture affects oxidation to the aromatic compound, so no separate dehydrogenation step is required.

In another embodiment the invention relates to the products prepared by the processes described herein. In those embodiments wherein the starting muconic acid is prepared from biomass, the resulting products of the process contain a significant percentage of carbon derived from renewable resources. Such products are unique because the products contain a detectable trace or amount of carbon 14, and preferably up to about 1 part per trillion, as determined according to ASTM D6866-08. The resulting products preferably contain 6 or greater carbons, more preferably 8 or greater carbons, derived from renewable resources, such as biomass, preferably by microbial synthesis. The resulting products are prepared from renewable resources prepared by microbial synthesis. In embodiments wherein the products are utilized to prepare polymers, the monomer units preferably contain 6 or greater carbons, and more preferably 8 or greater carbons, derived from renewable resources, such as biomass.

DESCRIPTION OF THE PREFERRED EMBODIMENT

Figure 1:
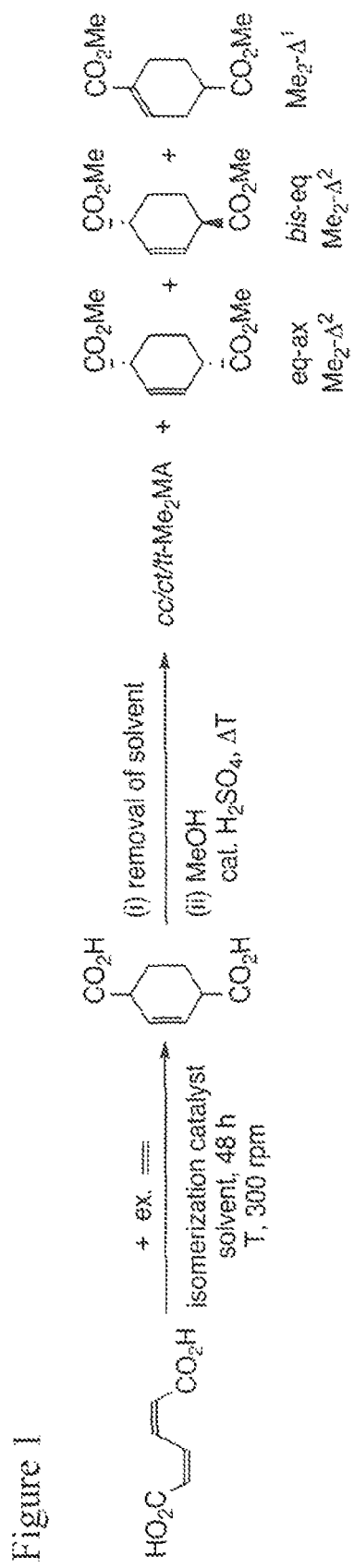
FIG. 1 shows the reaction sequence of Examples 43 to 47.

The following discussion applies to the teachings as a whole. Unless otherwise stated, all ranges include both endpoints and all numbers between the endpoints. The use of "about" or "approximately" in connection with a range applies to both ends of the range. Thus, "about 20 to 30" is intended to cover "about 20 to about 30", inclusive of at least the specified endpoints.

The disclosures of all articles and references, including patent applications and publications, are incorporated by reference for all purposes. References to the term "consisting essentially of" to describe a combination shall include the elements, ingredients, components or steps identified, and such other elements ingredients, components or steps that do not materially affect the basic and novel characteristics of the combination. The use of the terms "comprising" or "including" to describe combinations of elements, ingredients, components or steps herein also contemplates embodiments that consist essentially of the elements, ingredients, components or steps.

Plural elements, ingredients, components or steps can be provided by a single integrated element, ingredient, component or step. Alternatively, a single integrated element, ingredient, component or step might be divided into separate plural elements, ingredients, components or steps. The disclosure of "a" or "one" to describe an element, ingredient, component or step is not intended to foreclose additional elements, ingredients, components or steps. Likewise, any reference to "first" or "second" items is not intended to foreclose additional items (e.g., third, fourth, or more items); such additional items are also contemplated, unless otherwise stated. All references herein to elements or metals belonging to a certain Group refer to the Periodic Table of the Elements published and copyrighted by CRC Press, Inc., 1989. Any reference to the Group or Groups shall be to the Group or Groups as reflected in this Periodic Table of the Elements using the IUPAC system for numbering groups. Monomer units as used herein refer to the repeating unit of a polymeric structure. Derived from means prepared from or prepared using. Hydrocarbyl as used herein refers to a group containing one or more carbon atom backbones and hydrogen atoms, which may optionally contain one or more heteroatoms. Where the hydrocarbyl group contains heteroatoms, the heteroatoms may form one or more functional groups well known to one skilled in the art. Hydrocarbyl groups may contain cycloaliphatic, aliphatic, aromatic or any combination of such segments. The aliphatic segments can be straight or branched. The aliphatic and cycloaliphatic segments may include one or more double and/or triple bonds. Included in hydrocarbyl groups are alkyl, alkenyl, alkynyl, aryl, cycloalkyl, cycloalkenyl, alkaryl and aralkyl groups. Cycloaliphatic groups may contain both cyclic portions and noncyclic portions.

The present invention pertains generally to the synthesis of monomeric materials, polymeric materials or both. In one aspect, the invention is directed at synthesis that uses as a source of at least one starting material a biomass-derived product. For example, one preferred approach that is addressed herein pertains to the use of at least one dicarboxylic acid (e.g., muconic acid) or carboxylate derivative thereof derived from microbial synthesis. Examples of microbial synthesis processes taught in the art include, without limitation, Frost et. al. U.S. Pat. No. 5,616,496, incorporated herein by reference.

Another aspect of the invention pertains to the isomerization of at least one dicarboxylic acid (e.g., muconic acid) or carboxylate derivative thereof. More specifically, according to this aspect, cis,cis muconic acid or an ester thereof, is isomerized to a trans,trans configuration. The isomerization may be pursued wider an approach that includes one or more of a step of esterifying cis,cis muconic acid and then isomerizing the resulting ester, a step of isomerizing cis,cis muconic acid and then esterifying the resulting isomer, or a step of in situ isomerization (pursuant to which trans,trans muconic acid is reacted in the presence of one or more dieneophiles).

Another aspect of the invention relates to the formation of one or more cyclohexenes from one or more muconic acids or carboxylate derivatives thereof. For example, pursuant to this aspect a trans,trans muconic acid or a carboxylate derivative thereof (e.g., the trans,trans muconic acid or a carboxylate derivative thereof described above, optionally derived from biomass) may be reacted to form a cyclohexene having a carboxylate derivatives located in at least two positions, such as the 1 and 4 positions, of the cyclohexene rings.

Yet another aspect of the invention relates to the formation of one or more carboxylate derivatives of the above described one or more cyclohexene ring containing compounds. In particular, the teachings herein describe reactions for hydrogenating or dehydrogenating one or more cyclohexene containing compounds (e.g., derived from one or more muconic acids or carboxylate derivatives thereof) to form cyclohexene hydrogenation products (e.g. substituted cyclohexane products) or cyclohexene dehydrogenation products thereof (e.g. substituted benzene products). The dehydrogenation products are one or more products selected from substituted or unsubstituted terephthalic acid or carboxylate derivatives thereof.

Yet another aspect of the invention herein pertains to unique products that have the characteristics realized from the reactions described, and use of these products in subsequent applications.

The processes of the invention include the preparation of compounds having at least one benzene ring and carboxylates at the 1 and 4 position of the benzene ring and optionally at the 2 position of the benzene ring. In preferred embodiments these products can be referred to as substituted or unsubstituted terephthalic acid or carboxylate derivatives thereof. The process of the invention requires reaction of one or more muconic acids or carboxylate derivatives thereof with one or more dienophiles. Several other process steps may be included with this step. The following steps may be included in the preparation of the desired products: conversion of sugars, carbohydrates or cellulosic matter contained in biomass to muconic acid, typically the cis,cis isomer of muconic acid; isomerization of cis,cis and/or cis,trans muconic acid, or an ester thereof, to the trans,trans isomer; esterification of the one or more muconic acids to form one or more dihydrocarbyl esters of muconic acid; conversion of the one or more carboxylic acids or carboxylate esters thereof to another carboxylate derivative form; formation of one or more cyclohexene or benzene ring containing compounds having carboxylates at the 1 and 4, and optionally the 2 position, of the rings; dehydrogenation of the one or more cyclohexene compounds to form benzene ring containing compounds or hydrogenation of the one or more cylohexene compounds to form cyclohexane ring containing compounds; and esterification of one or more benzene, cyclohexene, cyclohexane having carboxylate groups at the 1,4 and optionally 2, positions.

Muconic acid can be prepared from biomass by any means known in the art, including the process described in Frost et. al U.S. Pat. No. 5,616,496, incorporated herein by reference. The resulting product is typically recovered by filtration techniques in the form of the cis,cis isomer of muconic acid. The cis,cis and cis,trans isomers of muconic acid do not react with dienophiles and therefore need to be isomerized for use in the reaction with dienophiles as described herein. Other methods of preparing muconic acid are known and muconic acid prepared by these processes can be used as the starting material in the processes of this invention. Preferably, the muconic acid used in the process steps described herein is prepared from biomass and more preferably by a microbial synthesis itself utilizing biomass or compounds dereived from biomass such as, for example carbohydrates.

In the embodiment where cis,cis and/or cis,trans muconic acids are used as the starting materials, they may be used in crude form or in purified form. When used in crude form it is preferred to remove microorganisms used as host cells in the preparation of muconic acid from sugars, starches, cellulosic materials and the like. The microorganisms are removed to prevent their interference with the various synthetic steps performed in the process. The microorganisms may be removed by means well known in the art, such as by filtration. The crude muconic acids may contain proteins, inorganic salts and the like. In certain processing sequences, as described hereinafter, it is preferable to purify the muconic acids. Preferably, purified cis,cis and/or cis,trans muconic acid are used for these processes: for the in situ isomerization of muconic acid and subsequent reaction with a dienophile in the same reaction vessel and where the cis,cis or cis,trans are esterified before isomerization to the trans,trans isomeric form.

Crude cis,cis and/or cis,trans muconic acid can be purified by dissolution in water or organic solvents and subsequent recrystallizaton from solution. Generally, the crude muconic acid and water or organic solvents need to be heated to dissolve the muconic acid. Cooling to ambient temperature, about 23° C., typically results in precipitation of purified muconic acid. Cooling to less than ambient, down to about 0° C. facilitates higher recovery or yields of purified muconic acids. The mixture of crude muconic acid and water or organic solvent is preferably heated to about 50° C. or greater to dissolve the muconic acid. The upper limit on heating of the mixture is limited by decomposition of the muconic acid and practicality. Preferred organic solvents for this process step are polar aprotic solvents, with alkanols being more preferred. Alkanols useful as solvents comprise straight and branched hydrocarbon chain further containing compounds further one or more, preferably one, hydroxyl groups. Preferred alkanols are $C_{1-6}$ straight and branched chain alkanols, with methanol, ethanol, and isopropanol most preferred. After precipitation of the purified muconic acid, the solvent is decanted off and the solid muconic acid is further dried, that is the residual solvent is removed by evaporation under reduced pressure. Preferably, the feedstock for this process is crude cis,cis muconic acid.

Cis,cis muconic acid can be isomerized directly to trans, trans muconic acid or isomerized to cis,trans muconic acid and then the cis,trans muconic acid can be isomerized to trans,trans muconic acid. Mixtures of cis,cis and cis,trans muconic acid can be isomerized to trans,trans muconic acid. Either muconic acid, or a carboxylate ester thereof, may be reacted with dienophiles to prepare the desired compounds. When an ester is used, the muconic acid can be isomerized or esterified first and then the other process step performed. Thus, in the isomerization step or steps performed to transform cis,cis muconate to the trans,trans muconate, the starting material can be in the acid or the carboxylate ester form.

In one embodiment, the cis,cis muconic acid, or ester thereof, may be converted to the cis,trans isomer in a discrete step. In such discrete step, the cis,cis muconic acid or ester thereof is dissolved or dispersed in water and exposed to elevated temperatures to convert the cis,cis muconic acid, or ester thereof, to the cis,trans isomer. Preferably, a sufficient amount of base is added such that the pH of the reaction mixture is about 4 or greater and more preferably about 4.5 or greater. Preferably, a sufficient amount of base is added such that the pH of the reaction mixture is about 6 or less and more preferably about 5.5 or less. Temperatures which may be used for this process steps include any temperature at which the isomerization proceeds. In one embodiment, the process is performed under reflux conditions. This process step is performed as long as required to convert the desired amount of cis,cis muconic acid or ester thereof to the cis,trans isomer. Preferably, this process step is performed for about 10 minutes or greater. Preferably, this process step is performed for about 60 minutes or less and more preferably about 30 minutes or less. The pH of the reaction mixture, the reaction temperature and the reaction time are interdependent. Within the preferred ranges recited, as the pH and temperature are increased the required reaction times are decreased. Preferably, the temperature, pH and reaction time are chosen to minimize the time required to perform the isomerization, while avoiding unwanted reactions or impractical operations.

In one embodiment, the starting muconic acid or carboxylate derivative thereof, are contacted with one or more isomerization catalysts, a source of ultraviolet radiaton or both, in solvent to form the trans,trans muconic acid. The starting muconic acid or carboxylate derivative thereof can be in the cis,cis, cis,trans or any combination of both isomeric forms. Any source of ultraviolet radiation which generates a radical under the conditions of the process may be used. Among preferred sources of ultraviolet radiation are light bulbs, xenon lamps, medium pressure mercury lamps or electrodeless lamps, natural light and the like. To enhance radical formation, where the radical former is ultraviolet radiation, a photoinitiator may be used in combination with the ultraviolet radiation source. Any commonly known photoinitiator useful with olefinically unsaturated compounds may be used in the processes described herein. Included in photoinitiators useful in this process are those disclosed in Baikerikar et. al. US Patent Publication 2007/0151178 paragraphs 0029, 0030 and 0032 incorporated herein by reference. Among preferred photoinitiators are alpha aminoketones, alpha hydroxyketone, phosphine oxides, phenylglyoxalates, thioanthones, benzophenones, benzoin ethers, oxime esters, amine synergists, maleimides, mixtures thereof and the like. Isomerization catalysts include any compounds which form radicals in unsaturated compounds when exposed to the reaction conditions, preferably under thermal conditions. Any isomerization catalyst with a suitable half life at the reaction temperatures of this process step can be used. Among preferred isomerization catalysts are compounds contained in the following classes: elemental halogens; dialkyl peroxides, such as di-tertiary-butyl peroxide, 2,5-dimethyl-2,5-di-tertiary-butyl-peroxyhexane, di-cumyl peroxide; alkyl peroxides, such as, tertiary-butyl hydroperoxide, tertiary-octyl hydroperoxide, cumene hydroperoxide; aroyl peroxides, such as benzoyl peroxide; peroxy esters, such as tertiary-butyl peroxypivalate, tertiary-butyl perbenzoate; and azo compounds, such as azo-bis-isobutyronitrile, and the like. More preferred compounds useful as isomerization catalysts are elemental halogens; with bromine, chlorine and iodine even more preferred; and iodine most preferred. Alternatively, the isomerization catalyst can be a hydrogenation catalyst as described hereinafter. Among preferred hydrogenation catalysts useful as an isomerization catalyst are nickel, platinum and palladium in homogeneous and heterogeneous forms. More preferred are heterogeneous catalysts, with carbon as the most preferred support. A most preferred catalyst for this purpose is palladium on carbon. The amount of isomerization catalyst used is that amount which catalyzes the isomerization of the muconic acid or a carboxylate derivative thereof. If too little is used the reaction does not proceed at a practical rate. If too much is used the isomerization catalyst may add to one of the double bonds of the muconic acid or carboxylate derivative thereof. The isomerization catalysts are preferably present in the reaction mixture in an amount of about 0.0001 equivalents or greater based on the equivalents of muconic acid or carboxylate derivatives thereof, more preferably about 0.001 equivalents or greater and most preferably about 0.005 equivalents or greater. The isomerization catalysts are preferably present in the reaction mixture in an amount of about 1.0 equivalent or less based on the equivalents of the muconic acid or carboxylate esters thereof, more preferably about 0.1 equivalents or less and about 0.01 equivalents or less. Any temperature at which isomerization of the muconic acid or ester thereof to the trans,trans isomeric form occurs may be used. Preferably, the temperature is about 23° C. or greater and most preferably about 60° C. or greater. Preferably, the temperature is about 150° C. or less, more preferably about 120° C. or less and most preferably about 100° C. or less. This process step is preferably performed at ambient temperatures or elevated temperatures. The limiting factor is solubility of the starting muconic acid or carboxylate esters in the solvents. Preferably, the solvent is saturated with muconic acid or one or more carboxylate derivatives thereof. The use of elevated temperatures renders the process more efficient by allowing a greater amount of starting muconic acid or carboxylate esters thereof to contact the isomerization catalyst. Preferably this process step is performed in a solvent. Any solvent which dissolves or disperses the reactants and which does not interfere in the desired reaction may be used for this step. Preferably, the solvent is polar and may be protic or aprotic. Protic in regard to a solvent means the solvent has a proton which freely dissociates, such an active hydrogen. Aprotic in regard to a solvent means the solvent does not have a proton which freely dissociates. Among preferred solvents are cyclic ethers, acyclic ethers, acetonitrile, dimethyl sulphoxide, N-methylpyrrolidone, ketones, alkyl acetates, alkanols or dimethylformamide and the like. More preferred solvents include $C_{1-4}$ alkanols, cyclic ethers, acyclic ethers, ethyl acetate, acetone and acetonitrile. This process step is performed as long as required to convert the desired amount of cis,cis and/or cis,trans muconic acid or ester thereof to the trans,trans isomer. In one preferred embodiment wherein cis, trans muconic acid is the starting material, the solvent used is aprotic and is more preferably an aprotic solvent from which trans,trans muconic acid precipitates at ambient temperatures. In this embodiment, the preferred solvents are cyclic ethers, alkyl acetates, and nitriles; with tetrahydrofuran, alkyl substituted tetrahydrofuran, dioxane, and acetonitrile more preferred; and tetrahydrofuran and methyl tetrahydrofuran most preferred. In a preferred embodiment, the starting muconic acid or carboxylate derivatives thereof are contacted with an isomerization catalyst and a source of ultraviolet radiation at elevated temperatures. The trans,trans muconic acid or carboxylate derivatives thereof are insoluble in the preferred solvents and precipitate from the reaction mixture. It can be recovered by simple removal, for instance by decantation, of the solvent from the reaction mixture. Preferably, the yield of trans,trans muconic acid or ester thereof is about 80 percent by weight or greater based on the weight of the starting muconic acid or ester thereof, more preferably about 90 percent by weight or greater and most preferably about 99 percent by weight or greater. Preferably, the trans,trans muconic acid recovered exhibits a purity of about 99 percent by weight or greater. Preferably the trans,trans muconic acid exhibits a detectable trace of carbon 14 number and more preferably up to about 1 part per trillion of carbon 14. In a preferred embodiment, the recovered trans,trans muconic acid or ester thereof has about 6 carbon atoms or greater derived from renewable resources such as biomass.

In the embodiment wherein muconic acid, or an ester thereof, is in the cis,trans isomeric arrangement, a preferred means of converting the cis,trans muconic acid, or ester thereof, to the trans,trans muconic acid or an ester thereof comprises contacting the cis,trans muconic acid, or an ester thereof, with an isomerization catalyst in an organic solvent. This is because cis,trans muconic acid or an ester thereof exhibit a higher solubility in organic solvents than the cis,cis and trans,trans isomers cis,cis.

Muconic acid and the esters of muconic acid can be represented by the following formulas

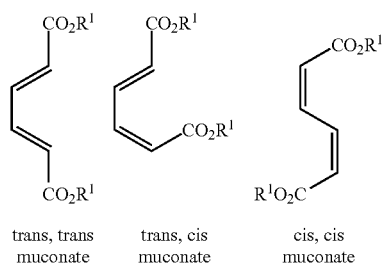

trans, trans muconate    trans, cis muconate    cis, cis muconate wherein $R^1$ is independently in each occurrence hydrogen, a hydrocarbyl group optionally containing a heteroatom containing functional group wherein the hydrocarbyl group does not interfere in the formation of a cyclohexene compound.

Muconic acid is esterified by contact with an esterifying agent under conditions that a hydrocarbyl group replaces the hydrogen on the oxygen of the carboxylic acid. The esterifying agent can be any compound which under the reaction conditions forms an ester on the carboxylate groups $(C(O)_2)$ of the muconic acid. The esterification agent can be any hydroxyl containing compound which reacts to form an ester under reaction conditions. Preferred esterification agents include hydrocarbon compounds having hydroxyl groups bonded thereto. More preferred esterifying agents include compounds corresponding to the formula $R^1OH$ wherein $R^1$ is a hydrocarbyl group, optionally containing a heteroatom containing functional group, wherein the hydrocarbyl group does not interfere in the formation of the cyclohexene compound. Preferred classes of esterifying agents include alkanols, aryl alcohols and aryl substituted alkanols. Preferred esterifying agents include alkanols, with $C_{1-10}$ alkanols being more preferred and methanol being most preferred. Among preferred aryl substituted alkanols is benzyl alcohol. Among preferred aryl alcohols are phenol and the various isomers of dihydroxy benzene. In another embodiment, the esterifying agent can be a polyglycol having one or more hydroxyl groups and one or more ether groups.

Muconic acid in one or more of its isomeric forms is contacted with one or more esterifying agents in the presence of one or more acids. The acids utilized can be any acids which facilitate the replacement of the hydroxyl group on the carboxylic acids with hydrocarbyloxy groups. Preferred acids are Bronsted acids. Bronsted acids are acids containing a protonic hydrogen that disassociates in solution. The acids are preferably strong acids. Strong acids as used herein mean acids with a pKa of lower than about 0. In a more preferred embodiment, the acids are strong mineral acids. Preferred strong mineral acids include sulfuric acid, nitric acid, phosphoric acid and hydrochloric acid, with sulfuric acid being most preferred. The acids are present in a sufficient amount to facilitate the esterification reaction. Where the esterification agent is in the liquid state no solvent is required. If the esterification agent is a solid or cannot function as a solvent, a solvent may be utilized. Preferred solvents are polar aprotic solvents as described hereinbefore which solubilize the muconic acid. More preferred solvents are cyclic and acyclic ethers, with cyclic ethers, such as tetrahydrofuran, more preferred. The esterification agent is preferably present in a sufficient amount to convert substantially all of the muconic acid to the carboxylate ester form. In a more preferred embodiment, the esterification agent is present in greater than an equivalent ratio based on the equivalents of muconic acid. Preferably, the esterification agent is present in a two to one molar ratio or greater as compared to the muconic acid. Where the esterification agent is also the solvent, the equivalent and molar ratios are much greater. The reaction can take place at any temperature wherein the esterification reaction proceeds at a reasonable rate. Preferably, the temperature is elevated. Elevated temperatures increase the amount of muconic acid which can be dissolved and contacted with the esterification agent. Preferably the temperature of the reaction is about 23° C. or greater, more preferably about 0.50° C. or greater and most preferably about 120° C. or greater. Preferably the temperature of the reaction is about 200° C. or less and most preferably about 150° C. or less. The reaction time utilized is chosen to give the desired yield of product. The product recovered may be a monohydrocarbyl muconate, a dihydrocarbyl muconate or a mixture thereof, in a more preferred embodiment the product is substantially dihydrocarbyl muconate. More preferred dihydrocarbyl muconates include dialkyl muconates, more preferably a $C_{1-10}$ dialkyl muconates and most preferably dimethyl muconate. The hydrocarbyl groups can be substituted with substituents which do not interfere with the reaction of the dihydrocarbyl muconate with one of more dienophiles. The trans,trans muconate esters precipitate from the solution upon cooling. Preferably the reaction mixture is cooled to less than about 40° C. to facilitate precipitation, and preferably to ambient (23° C.) or less. The dihydrocarbyl muconate may be recovered by simple removal of the solvent or excess esterification agent, such as by decantation. Preferably, the yield of dihydrocarbyl muconate is about 70 percent by weight or greater based on the weight of the starting muconic acid. Preferably, dihydrocarbyl muconate recovered exhibits a purity of about 99 percent by weight or greater and most preferably about 99.5 percent by weight or greater. Preferably, the dihydrocarbyl muconate exhibits a detectable amount of carbon 14 number and preferably of up to about one part per trillion. In a preferred embodiment, the recovered dihydrocarbyl muconate has about 6 carbon atoms or greater derived from renewable resources, such as biomass.

In another embodiment, muconic acid may be contacted with an esterifying agent in an aqueous base solution to form a dihydrocarbyl muconate. Preferably this reaction is performed at a temperature of from ambient to (about 23° C.) to about 40° C. The base can be any base which binds the protons of the carboxyl groups of muconic acid. Preferably, the esterifying agents are present in an equivalent ratio of about 2:1 or greater. The upper limit on the equivalents is practicality. The dihydrocarbyl muconate is recovered by extraction into organic solvent and subsequent evaporation of the extracting organic solvent.

The one or more muconic acids can be converted to other forms of carboxylate derivative groups using reaction sequences known to those skilled in the art. As used herein the term carboxylate derivative refers to any group which contains a carbonyl group (C=O) or a nitrile group

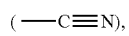

wherein the carbonyl group is bonded to an anion so at to form a salt or to a heteroatom, such as oxygen, nitrogen, sulfur or one or more halogens. The heteroatom may be further bonded by a covalent bond to one or more other groups, such as hydrocarbyl groups which may optionally contain one or more heteroatoms, or may be electronically (electrostatically) bonded to a cation to form a salt. Preferably, the carboxylate derivative is an acyl halide, carboxylic acid, amide, ester, thiol ester, mercaptocarbonyl, an anhydride, a nitrile, a salt with an anion or a salt with a cation. Preferred cations include alkali metal ions and unsubstituted and hydrocarbyl substituted ammonium ions. Preferred carboxylate derivatives comprise carboxylic acids, acyl halides, amides, anhydrides and esters. More preferred carboxylate derivatives include carboxylic acids and esters, with esters most preferred. Preferred carboxylate derivative groups correspond to the formula

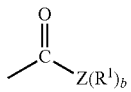

wherein $R^1$ is independently in each occurrence hydrogen, a hydrocarbyl group optionally containing one or more heteroatoms or a cation;

Z is independently in each occurrence an anion, oxygen, nitrogen, sulfur, a nitrite, or a halogen; and, b is independently in each occurrence 0, 1 or 2 with the proviso that b is 0 when Z is an anion, halogen or nitrite; 1 when Z is oxygen or sulfur and 2 when Z in nitrogen. $R^1$ is preferably hydrogen or a $C_{1-12}$ hydrocarbyl group which may contain one or more heteroatoms, more preferably hydrogen or a $C_{1-10}$ alkyl group which may contain one or more heteroatoms, more preferably hydrogen or a $C_{1-3}$ alkyl group and most preferably hydrogen or methyl.

Acyl halides preferably correspond to the formula

wherein X is a halogen. X is preferably chlorine or bromine, with chlorine most preferred.

Amides preferably correspond to the formula

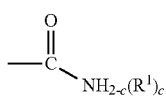

wherein c is separately in each occurrence 0, 1 or 2, with 0 or 1 being preferred.

Esters preferably correspond to the formula

Mercaptocarbonyls preferably correspond to the formula

Thiol esters preferably correspond to the formula

Anhydrides preferably correspond to the formula

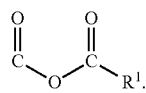

Nitriles preferably correspond to the formula:

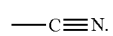

Carboxylate derivatives of muconic acid can be represented by the following formulas

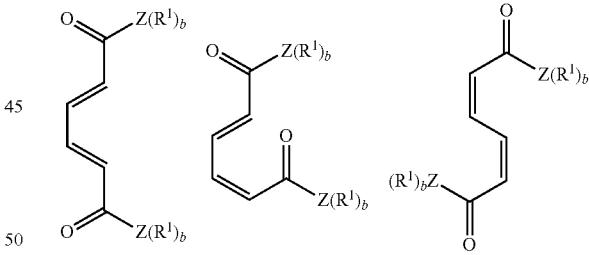

wherein $R^1$ is as defined hereinbefore In alternative embodiments, the dihydrocarbyl muconates, especially the trans, trans isomeric versions, can be prepared from muconic acid by any known synthetic sequence. For example the dihydrocarbyl muconates may be prepared by the processes disclosed in the following sections of Jerry March, *Advanced Organic Chemistry*, $2^{nd}$ Edition, Wiley, 1977, at pages 361-367, incorporated herein by reference: section 0-22 alcoholysis of acyl halides, section 0-23 alcoholysis of anhydrides, and section 0-24 esterification of acids. Amide based carboxylate derivatives may be prepared by processes known to those skilled in the art including those disclosed in March, ibid, in sections 0-52 amination of alkanes, 0-53 formation of nitriles, 0-54 acylation of amines by acyl halides, and 0-55 acylation of amines by anhydrides at pages 381 to 384, incorporated herein by reference. Acyl halides may be prepared by processes known to those skilled in the art including those disclosed in March, ibid, section 0-75 formation of acyl halides from acids at page 398 incorporated herein by reference. Thiolesters of muconic acid may be prepared by processes known to those skilled in the art, including those disclosed in March, ibid, wherein muconic acid is converted to acyl halides as described above and then convened to a thiol or a thiol ester by the process disclosed in section 0-40 on pages 375 and 376, incorporated herein by reference. Muconic acids may be convened to dianhydride analogs by processes known to those skilled in the art such as disclosed in March, ibid, section 0-29 acylation of acids with acyl halides and section 0-30 acylation of acids with acids, at pages 369 and 370 incorporated herein by reference. Muconic acids may be converted to nitriles by processes known to those skilled in the art such as disclosed in March, second edition, section 6-63 at pages 883 and 884 conversion of acid salts to nitriles.

One or more muconic acid or carboxylate derivatives thereof are reacted with one or more dienophiles to prepare a cyclohexene compound having carboxylate groups

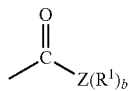

in the 1 and 4 positions, and optionally in the 2 position. One or more muconic acids means that a mixture of isomers may be used. In one preferred embodiment the starting muconic acid or carboxylate thereof is in the trans-trans isomeric form. Preferably such carboxylates are in the trans,trans isomeric arrangement. In one embodiment, the cis,cis and/or cis,trans isomers of muconic acid or carboxylate derivatives thereof may be utilized as starting materials. In this embodiment, it is believed that the muconic acid or carboxylate derivatives thereof isomerize in situ before reacting with the dienophile. Carboxylate esters are preferred as starting materials in this reaction. The dienophile can be any compound having unsaturation which reacts with muconic acid or a carboxylate derivative thereof to form a cyclohexene compound. Preferred dienophiles correspond to the following formula

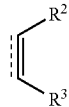

wherein
$R^2$ is independently in each occurrence hydrogen, halogen, a hydrocarbyl group optionally containing one or more heteroatoms or heteroatom containing functional groups wherein the hydrocarbyl group does not interfere in the formation of the cyclohexene compound; and
$R^3$ is independently in each occurrence hydrogen, halogen or a hydrocarbyl group optionally containing one or more heteroatoms or heteroatom containing functional groups wherein the hydrocarbyl group does not interfere in the formation of the cyclohexene compound; with the proviso that $R^2$ and $R^3$ may be combined to form a cyclic ring which may contain heteroatoms. Preferred classes of dienophiles include alkenes, unsaturated cyclic compounds, alkynes, aromatic compounds having unsaturated substituents, and the like.

Preferred alkenes useful as dienophiles include any straight or branched aliphatic compound containing at least one double bond wherein such compounds may contain heteroatoms or heteroatom containing functional groups which do not interfere in the formation of the compounds having 6 membered cyclic rings. Such heteroatoms include oxygen, nitrogen, phosphorous, sulfur and halogens. Preferred halogens include chlorine and bromine, with chlorine preferred. Preferred alkenes include unsaturated acids, carbonates containing unsaturation, unsaturated esters, unsaturated nitriles, vinyl chloride, vinyl acetate, unsaturated aliphatic hydrocarbons having one or more double bonds (including ethylene, propylene, all isomers of butene, pentene, hexane, heptene, octene), and the like. Alkenes useful herein can have unsaturation at any point of the carbon chain. Preferred alkenes are those having unsaturation at the terminal end of a chain, which is between the 1 and 2 carbon atoms. Among preferred unsaturated carbonates is vinylidene carbonate. Among unsaturated acids are any carboxylic acids having unsaturation in the backbone of the carbon chain including methacrylic and acrylic acids. Ethylene and propylene are more preferred unsaturated aliphatic hydrocarbons, and ethylene is most preferred. Preferred unsaturated cylic compounds include cyclopropene, cyclobutene, cyclopentene, cyclohexene which may optionally contain a heteroatom or be substituted with a heteroatom containing subsituent as described hereinbefore. Any unsaturated ester which reacts with muconic acid, or a carboxylate derivative thereof, may be used as a dienophile in this process. Preferred unsaturated acids or esters correspond to the formula

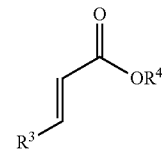

wherein $R^3$ is as described hereinbefore, and
$R^4$ is independently in each occurrence hydrogen, a hydrocarbyl group optionally containing a heteroatom containing functional group. Preferred unsaturated esters include hydrocarbyl acrylates, hydrocarbyl alkylacrylates and the like. Preferably, the double bond is located on a terminal carbon. More preferred unsaturated esters include hydrocarbyl acrylates and hydrocarbyl alkylacrylates, such as methyl methacrylate, with the hydrocarbyl acrylates being more preferred. The unsaturated esters may contain heteroatoms or heteroatom containing functional groups which do not interfere in the formation of the compounds having 6 membered cyclic rings as described hereinbefore. Preferred hydrocarbyl acrylates include $C_{1-10}$ alkyl acrylates with methyl acrylate, butyl acrylate and 2-ethylhexyl acrylate being more preferred. The aromatic compounds having unsaturated subsituents useful as dienophiles include any aromatic compound having an unsaturated subsituent which reacts with muconic acid or a carboxylate derivative thereof under the reaction conditions defined herein. Among preferred aromatic compounds containing unsaturated subsituents are styrene, alpha-methylstyrene, o-methylstyrene, m-methylstyrene, p-methylstyrene, ar-ethylstyrene, ar-vinylstyrene, ar-chlorostyrene or ar-bromostyrene, and the like. Preferably, the unsaturated aromatic compound corresponds to the formula

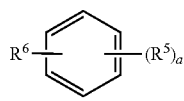

wherein
R⁵ is independently in each occurrence a hydrocarbyl group optionally containing a heteroatom containing functional group or a halogen; and
R⁶ is an alkenyl group optionally containing a heteroatom containing functional group. Another preferred class of cyclic unsaturated compounds is cyclic unsaturated anhydrides. Among preferred cyclic anhydrides is maleic anhydride, and the like, with maleic anhydride preferred. The alkyne containing compounds useful as dienophiles include any compound containing a triple bond

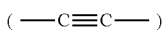

which reacts with muconic acid or a carboxylate derivative thereof under the reaction conditions. The triple bond can be located at any position in the carbon chain of the alkyne, and is preferably between two terminal carbon atoms. Preferably alkyne containing compounds include all isomers of $C_{2-n}$ alkynes, acetylenecarboxylic acid and carboxyate derivatives thereof and acetylene dicarboxylic acid and carboxylate derivatives thereof. More preferable alkynes include acetylene, acetylenic esters, propyne, butyne and the like, with acetylenic esters being most preferred. Preferred alkynes correspond to the formula

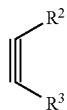

wherein $R^2$ and $R^3$ are as described herein before. Preferred acetylenic esters correspond to one of the formulas

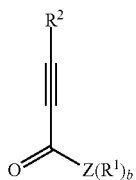

and more preferably

wherein $R^1$, $R^2$, $R^3$, Z and b are as described hereinbefore. Preferred acetylenic esters comprise one or more carboxylate esters bonded directly to carbons of the triple bond.

Preferably the reactants are contacted at a temperature at which they are in liquid form so as to mix intimately or are in a solvent which dissolves the starting materials. Preferably, the reaction is performed neat, that is, in the absence of solvent. The one or more muconic acids, or carboxylate derivatives thereof, and one or more dienophiles are contacted at elevated temperatures. Any temperature at which the one or more muconic acids, or carboxylate derivatives thereof, and dienophiles are in the same phase and react at a reasonable rate may be used. Preferably, the temperature is about 100° C. or greater, more preferably about 130° C. or greater and more preferably about 140° C. or greater. Preferably, the temperature is about 180° C. or less, more preferably about 170° C. or less, even more preferably about 160° C. or less and most preferably about 150° C. or less. The reaction can take place neat, that is, in the absence of a solvent, or in the presence of a solvent. In those embodiments wherein a solvent is used, any solvent which facilitates the reaction and which does not interfere in the reaction may be used. Preferred solvents are aprotic solvents. Preferred solvents are nonpolar. More preferred solvents are hydrocarbons, acyclic ethers, alkyl polyethers, and cyclic ethers which can be used at the temperatures of the reaction, that are liquid at the reaction temperatures, that is, have a boiling point above the reaction temperature. Among preferred solvents are xylene, decaline, toluene, cyclic ethers, glycol ethers and polyglycol ethers and the like. In the embodiment where trans,trans muconic acid is used as a starting material it is preferable to perform the reaction in water or in a solvent which does not transesterify the acid groups of the muconic acid to avoid side reactions and in which the muconic acid is soluble. The reaction is allowed to proceed until the desired yield of product is obtained. Preferably, the reaction time is about 24 hours or greater. Preferably, the reaction time is about 48 hours or less. Optionally, the reactants are reacted in the presence of a Lewis acid. The Lewis acid may be present in a catalytic amount, preferably about 0.01 percent by weight or greater of the reaction mixture and more preferably about 0.1 percent by weight or greater of the reaction mixture; and preferably about 10.0 percent by weight or less of the reaction mixture and more preferably about 1.0 percent by weight or less of the reaction mixture. The Lewis acid may be homogeneous or heterogeneous and is preferably heterogeneous. In a preferred embodiment, the reaction is carried out in the presence of the one or more compounds which inhibit the polymerization of unsaturated compounds. Any compound which prevents the polymerization of unsaturated compounds may be used in the reaction. Among preferred classes of compounds which prevent the polymerization of unsaturated compounds are hydroquinones, benzoquinones, phenothiazines and anisoles, mixtures thereof and the like. Among preferred compounds which prevent the polymerization of unsaturated compounds are benzoquinone, hydroquinone, t-butyl benzoquinone, methyl ether of hydroquinone, catechol, alkylated catechols, butylated hydroxyanisoles and the like, with hydroquinone being more preferred. The compounds which inhibit the polymerization of unsaturated compounds are present in the reaction mixture in a sufficient amount to prevent polymerization. Preferably, compounds which inhibit the polymerization of unsaturated compounds are present in an amount of about 0.05 percent by weight or greater based on the weight of the muconic acid, or carboxylate derivative thereof, most preferably about 0.01 percent by weight or greater. Preferably, compounds which inhibit the polymerization of unsaturated compounds are present in an amount of about 10.0 percent by weight or less based on the weight of the one or more muconic acids or carboxylate dereivative thereof, more preferably about 2.0 percent by weight or less and most preferably about 1.0 percent by weight or less. The ratio of the one or more muconic acids or carboxylate derivatives thereof to one or more dienophiles is selected to maximize the yield of the desired products. Preferably, the mole ratio of dienophiles to muconic acid and carboxylate derivatives thereof is about 1.7:1.0 or greater, more preferably about 2.0:1.0 or greater and most preferably about 3.0:1.0 or greater. The upper limit of the mole ratio of dienophiles to muconic acid and carboxylate derivatives thereof is based on practicality and is preferably about 10.0:1.0 or less. In those embodiments wherein a solvent is utilized, the concentration of the one or more muconic acids, or carboxylate derivatives thereof, in the solvent is preferably about 0.2 Molar (M) or greater, and most preferably about 0.5 M or greater. In those embodiments wherein a solvent is utilized, the concentration of one or more muconic acids or carboxylate derivatives thereof in the solvent is dictated by solubility of the muconic acid in the solvent and is preferably about 4.0 Molar (M) or less and most preferably about 3.0 M or less. The concentration of dienophile in the solvent is chosen in accordance with the concentration of the one or more muconic acids or carboxylate derivatives thereof in the solvent and the desired mole ratios of dienophiles to muconic acids or carboxylate derivatives thereof as described hereinbefore. The concentration of dienophile in the solvent is preferably about 0.5 M or greater and most preferably about 1.0 M or greater. The upper limit of the concentration of dienophile in the solvent is practicality. Preferably the dienophile is also used as the solvent. Where the dienophile is not the solvent a practical upper limit is about 2.4 M or less.

The cyclohexene compound may be recovered by any means which allows isolation of the cyclohexene compound in a manner wherein the cyclohexene compound is recovered in the desired purity and yields, where the reaction is performed neat, the cyclohexene compound may be recovered by distillation or contacting the mixture with a low polar solvent, such as an ether, in a manner such that the cyclohexene compound dissolves, filtering off the unreacted materials which do not dissolve and concentrating the solvent by evaporation to give relatively pure cyclohexene compound. Where a solvent is used, recovery is performed by distillation of the reaction mixture or by chromatographic separation. Preferably, the yield of cyclohexene compound is about 70 percent by weight or greater based on the weight of the starting muconic acid. Preferably, cyclohexene compound recovered exhibits a purity of about 90 percent by weight or greater and most preferably about 99 percent by weight or greater. Preferably the cyclohexene compound exhibits a detectable amount of carbon 14 and preferably up to about 1 part per trillion. In a preferred embodiment the recovered cyclohexene compound has about six or greater, preferably about eight or greater, of its carbon atoms derived from renewable resources such as biomass.

In the embodiment wherein the muconic acid or carboxylate derivatives thereof are in the cis,cis or cis,trans isomeric form, the reaction with dienophiles is preferably performed in solvent. Preferably, in this embodiment carboxylate esters of muconic acid are reacted with the dienophiles. In this embodiment the process can be performed in the presence of an isomerization catalyst and/or the presence of Lewis acid catalyst as described herein.

In the embodiment wherein the starting dienophile is an alkene which is in the gaseous form at ambient pressure and temperature, the one or more muconic acids or carboxylate derivatives thereof are preferably dissolved in a solvent, as described hereinbefore, and the solution is contacted with the alkene gas. Where the alkenes are liquid, the one or more muconic acids or carboxylates thereof are preferably dissolved in a solvent or alkene in as high a concentration as possible, the concentration is limited by the solubility of the one or more muconic acid's or carboxylate derivatives thereof. Preferably, the one or more muconic acids or carboxylate derivatives thereof are dissolved in the solvent or alkene at a molarity of about 0.01 M or greater and more preferably about 0.12 M or greater. Preferably, the one or more muconic acids or carboxylate derivatives thereof are dissolved in the solvent or alkene at a molarity of about 4.0 M or less and more preferably about 3.0 M or less. The process is performed at ambient or elevated pressures. Elevated pressures are preferred as this allows the use of a significant excess of alkene. When elevated pressures are utilized, it is preferred to utilize a closed system and elevate the pressure by adding the alkene up to the chosen reaction pressure. Preferably, after the reaction system, containing one or more muconic acids and/or carboxylate derivatives thereof in the solvent of choice, optionally in the presence of a catalyst, is closed, it is evacuated at normal pressure to remove air and refilled with the gaseous alkene. This evacuation/refilling cycle is preferably repeated several times. The reaction system is then filled up to the chosen gaseous alkene pressure and stirred for up to 30 minutes so as to saturate the solvent with the gaseous alkene. Then is the reaction system closed and heated to the desired reaction temperature. Air or an inert gas may also be present in the system but this is not desirable because this lowers the reaction rate. The pressure chosen is limited by the equipment used in the reaction and the equipment used to deliver the alkene and any other gas present. Preferably, the pressure is about 14.7 psi (0.101 MPa) or greater, more preferably 100 psi (0.689 MPa) or greater and most preferably about 250 psi (1.72 MPa) or greater. Preferably, the pressure is about 50,000 psi (345 MPa) or less, more preferably 15,000 psi (103 MPa) or less, even more preferably about 10,000 psi (68.9 MPa) and most preferably about 270 psi (1.86 MPa) or less. Where the alkene is a gas, the alkene is preferably introduced in a significant excess and the desired pressure to be used dictates the amount of the excess utilized. If the alkene is liquid it is preferred to use the alkene as the solvent provided the muconic acid or carboxylate derivatives thereof are soluble in the alkene at reaction temperatures. Preferably the resulting product is soluble in the liquid alkene where used as the solvent. The reaction rate is significantly impacted by the reaction temperature and the pressure of the alkene present where it is a gas. Thus the reaction temperature is chosen such that the reaction rate is reasonable. Preferably, the reaction temperature is about 100° C. or greater, more preferably about 120° C. or greater and most preferably about 150° C. or greater. Preferably, the reaction temperature is less than about 170° C. as the products decompose near this temperature and more preferably the temperature is about 160° C. or less. The reaction time is selected to allow preparation of the cyclohexene compounds in the desired yield. Preferably, the reaction time is about 1 hour or greater and most preferably about 6 hours or greater. Preferably, the reaction time is about 24 hours or less, more preferably about 12 hours or less and most preferably about 9 hours or less. The cyclohexene compound may be recovered by removing the solvent by evaporation. Where the reaction is performed neat the resulting product is recoverd by distillation Preferably, the yield of cyclohexene compound is about 90 percent by weight or greater based on the weight of the starting muconic acid or carboxylate derivatives thereof and more preferably about 95 percent by weight or greater. Preferably, cyclohexene compound recovered exhibits a purity of about 95 percent by weight or greater and most preferably about 99 percent by weight or greater. Preferably, the cyclohexene compound exhibits a detectable amount of carbon 14 number and preferably up to about one part per trillion. In a preferred embodiment, the recovered cyclohexene compound has about six or greater, preferably about eight or greater, of its carbon atoms derived from renewable resources such as biomass. In one preferred embodiment, the alkene is derived from renewable resources, such as ethylene derived from ethanol. Processes for the preparation of alkenes from renewable resources are well known in the art. In such embodiments, the number of renewable carbon atoms in the final product is about 8 or greater.

In the embodiment wherein the alkene dienophiles are reacted with muconic acid in water as a solvent, the product undergoes partial tautomerization. The resulting product mix includes products with the double bond between the 1 and 2 carbons of the cyclohexene ring and products with a double bond between the 2 and 3 carbons of the cyclohexene ring. In the embodiment wherein muconic acid is the starting material and the solvent is an esterifying agent, such as an alkanol, the resulting cyclohexene product undergoes esterification.

In the embodiment wherein the one or more dienophiles includes one or more alkynes which are in the gaseous form, such as acetylene, the one or more dienophiles are dispersed or dissolved in one or more solvents, such as those used for the reaction of dienophiles with alkenes. The reaction can be performed at atmospheric pressure or at elevated pressures by providing the alkyne in sufficient amount to pressurize the reaction mixture. Alternatively the alkyne can be introduced in admixture with an inert gas. Any gas which is inert and which can carry the dienophiles can be used. Among preferred gases are air, nitrogen, argon, and the like. Where the alkyne is liquid, the alkyne may be used as the solvent or the one or more alkynes and dienophiles may be contacted in one or more solvents. Preferred solvents are non polar solvents which are liquid under reaction conditions. Preferred solvents are cyclic and acyclic ethers and hydrocarbon solvents, such as xylene or decalin. Preferably, the reaction is performed with an excess of the alkyne as the reaction medium. Preferably, the reaction is performed in a closed reactor under pressure. The pressure is chosen to provide an excess of the alkyne and to keep liquid alkynes in the liquid state under the reaction conditions, such as at elevated temperatures. Preferably, the alkyne is present in a molar excess. More preferably, the alkyne is present in a molar excess or about 3.0:1.0 or greater and more preferably about 5.0:1.0 or greater. The upper limit on the excess of the alkyne is practicality and the ratio is preferably about 6.0:1.0 or less. The temperature of the reaction is chosen such that the reaction rate is reasonable and to be below the decomposition temperature of the reactants and the products. Preferably, the temperature is about 130° C. or greater, more preferably about 140° C. or greater and most preferably about 150° C. or greater. Preferably the temperature is about 160° C. or less. The reaction time is preferably about one hour or greater, more preferably about 2 hours or greater and most preferably about 4 hours or greater. The reaction time is preferably about 24 hours or less and most preferably about 16 hours or less. The resulting product has a six membered aromatic ring in the desired products. Aromatic compounds with five membered rings are also prepared as by-products. The products are separated by column chromatography. Preferably, the yield of desired products is about 80 percent by weight or greater based on the weight of the starting muconic acid or carboxylate derivatives thereof and more preferably about 90 percent by weight or greater. Preferably, desired compounds recovered exhibit purity of about 90 percent by weight or greater and most preferably 99 percent by weight or greater. Preferably the desired product exhibits a detectable amount of carbon 14 and preferably up to about one part per trillion. In a preferred embodiment, the recovered compound has about six or greater, preferably about 8 or greater, of its carbon atoms derived from renewable resources such as biomass.

In a preferred embodiment, the cyclohexene compounds prepared correspond to one of the formulas

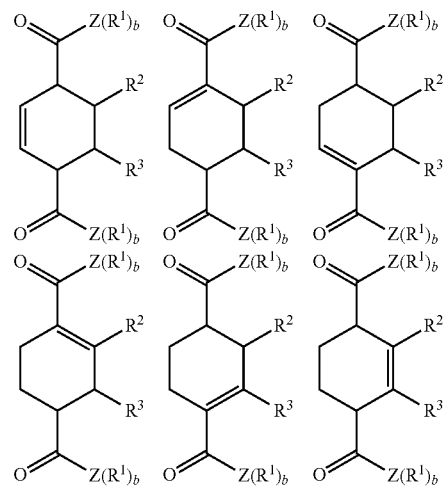

wherein $R^1$, $R^2$, $R^3$, Z and b are as described herein before.

In a more preferred embodiment, the cyclohexene compounds prepared correspond to one of the formula

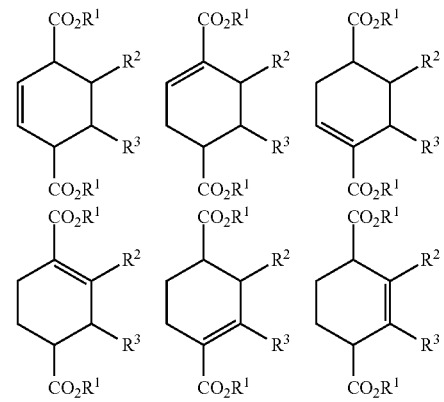

wherein $R^1$, $R^2$ and $R^3$ are as described herein before. In the embodiment wherein the dienophile is an unsaturated ester the cyclohexene compound preferably corresponds to one of the formulas

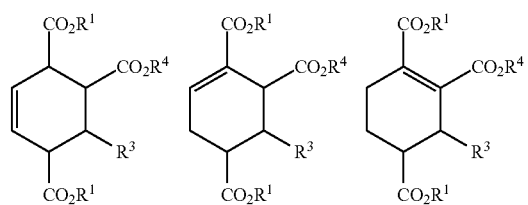

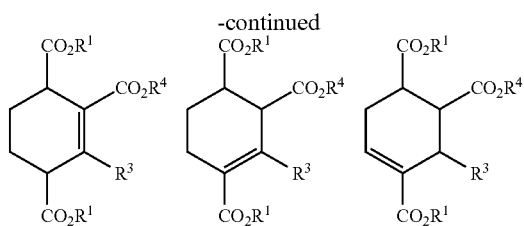

wherein $R^1$, $R^3$ and $R^4$ are as described hereinbefore. In the embodiment, the wherein the starting dienophiles comprise maleic anhydride or an analog thereof the cyclohexene formed preferably corresponds to one of the formulas

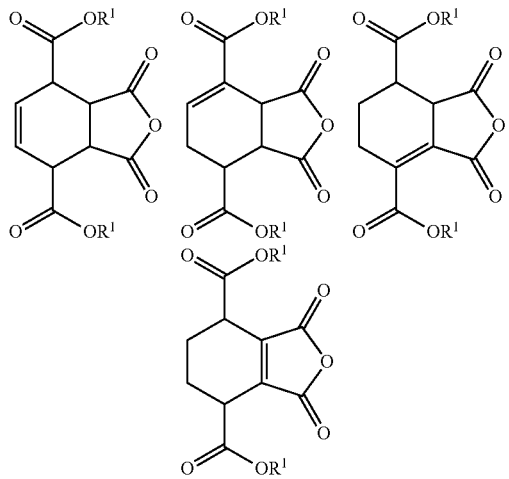

wherein $R^1$ is as described hereinbefore. In the embodiment, wherein the starting dienophile is an aromatic compound having an unsaturated substituent the cyclohexene formed preferably corresponds to one of the formulas

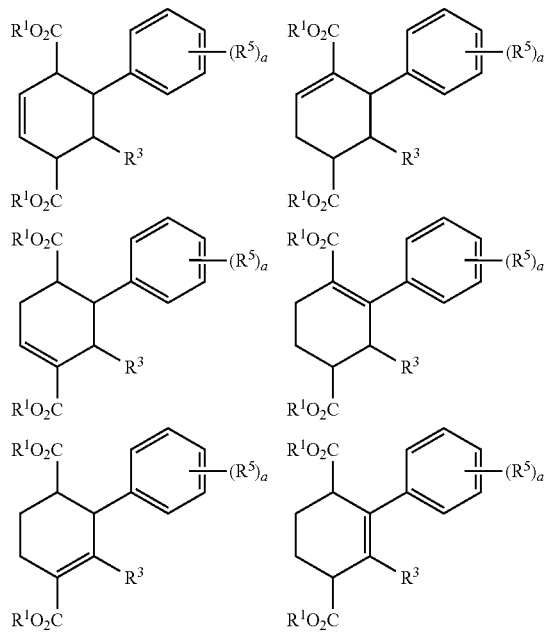

wherein $R^1$, $R^3$ and $R^5$ are as described hereinbefore. In the embodiment where the starting dienophile is an acetylenic ester the product is a trimellitate or a derivative thereof which corresponds to the formula

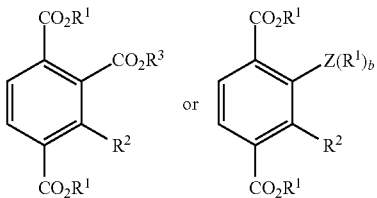

wherein $R^1$, $R^2$, $R^3$, Z and b are as described hereinbefore.

Preferably $R^1$ is independently in each occurrence hydrogen, or an alkyl, haloalkyl, aryl, haloaryl, alkylaryl, alkyloxy, or carboxyl group containing not more than 10 carbon atoms. Even more preferably, $R^1$ is independently in each occurrence a $C_{1-10}$ alkyl group; and most preferably $R^1$ is methyl. Preferably, $R^2$ and $R^3$ are independently in each occurrence hydrogen, halogen, alkyl, alkaryl, aryl, alkyl carboxylate or may be combined to form a cyclic ring which may contain one or more hetero atoms. More preferably, $R^2$ and/or $R^3$ are independently in each occurrence hydrogen, halogen, or an alkyl, haloalkyl, aryl, haloaryl, alkylaryl, alkyloxy, or carboxyl group containing not more than 10 carbon atoms. Even more preferably, $R^2$ and $R^3$ are independently in each occurrence hydrogen, chloro, bromo, $C_{1-8}$ alkyl, phenyl, or $C_{1-8}$ alkyl carboxylate or may be combined to form a cylic anhydride. $R^2$ is even more preferably hydrogen, chloro, methyl, ethyl or phenyl. Preferably, $R^4$ is independently in each occurrence a $C_{1-10}$ alkyl group. More preferably, $R^4$ is independently in each occurrence a $C_{1-8}$ alkyl group. Most preferably, $R^4$ is independently in each occurrence methyl, butyl or ethylhexyl. Preferably, $R^5$ is independently in each occurrence a hydrocarbyl group optionally containing a heteroatom containing functional group. More preferably, $R^5$ is independently in each occurrence a $C_{1-10}$ alkyl group. Preferably, a is independently in each occurrence 0 or 1, and most preferably a is 0. In one embodiment, $R^2$ is independently in each occurrence halogen, an alkyl, haloalkyl, aryl, haloaryl, alkylaryl, alkyloxy, or carboxyl group containing not more than 10 carbon atoms and $R^3$ is hydrogen; even more preferably, $R^2$ is independently in each occurrence hydrogen, chloro, bromo, $C_{1-8}$ alkyl, phenyl, or $C_{1-8}$ alkyl carboxylate and $R^3$ is hydrogen; and $R^2$ is even more preferably hydrogen, chloro, methyl, ethyl or phenyl while $R^3$ is hydrogen.

To prepare compounds having at least one benzene ring having carboxylate groups at the 1 and 4, and optionally at the 2 position, such as substituted or unsubstituted terephthalic acid or carboxylate derivatives thereof (including trimellitic acid or carboxylate derivatives thereof), from the cyclohexene compounds prepared by the reaction of muconic acid and/or carboxylate derivatives thereof with dienophiles as described herein, the cyclohexene compounds are subjected to dehydrogenation, which can also be called oxidation or aromatization. In the dehydrogenation step, the cyclohexene compounds are contacted with one or more dehydrogenation catalysts. In one embodiment, the cylcohexene compound is contacted with an oxidant and one or more dehydrogenation catalysts, at elevated temperatures. In one preferred embodiment the cyclohexene compound is contacted with the dehydrogenation catalyst in the absence of an oxidant. Preferably, an inert gas is passed through the reactor to carry away hydrogen gas generated in the dehydrogenation process. Oxidants as used herein refer to any element of compound which facilitates the oxidation of a cyclic ring to remove hydrogen atoms and to form unsaturated bond in a ring. Preferably the oxidation of the cyclic ring results in the formation of an aromatic ring. Among preferred oxidation agents are oxygen, monoclinic sulfur, nitric acid, peroxides, hyprochlorites and persulfates, chloranial and dicyanodichlorobenzoquinone. Oxygen in the form of air is a preferred oxidant. The oxidation agent is present in stoichiometric or greater amounts, preferably greater than stoichiometric amounts. The excess is chosen so as to drive the rate of the reaction. In one preferred embodiment the reaction is performed in the presence of an oxidant that reacts with the hydrogen generated in the process. Oxidants that react with hydrogen include oxygen. The reactants can be contacted neat or in a solvent. Preferable solvents are aprotic solvents with hydrocarbons, ethers (such as tetrahydrofuran) and pyrolidones (such as N-methylpyrolidone). Preferably, the solvents are liquid under reaction conditions. The cyclohexene ring containing compound concentration in solvent is at a concentration below the concentration at which disproportionation occurs. Preferably, the cyclohexene ring containing compound concentration in solvent is about 3.0 M or less and most preferably about 2.0 M or less. Preferably, the cyclohexene ring containing compound concentration in solvent is about 0.05 M or greater and most preferably about 0.10 M or greater. In one embodiment the reaction is performed at atmospheric pressure (14.7 psi, 0.101 MPa). At atmospheric pressure, the reaction can be performed at reflux of the solvent, provided the solvent boils at acceptable temperatures. Alternatively, the reaction can be performed at elevated pressures. Preferably, the oxidation agents are present in a molar excess of greater than about 2.0:1.0. Preferably, the oxidation agents are present in a molar excess of about 8.0:1.0 or less. Suitable temperatures are those at which hydrogen is abstracted from the cyclohexene compound to form double bonds in the ring of the cyclohexene containing compound. Preferably, the temperature is about 120° C. or greater and more preferably about 130° C. or greater. Preferably, the temperature is about 400° C. or less, more preferably about 350° C. or less and most preferably about 325° C. or less. If the reaction is performed at elevated pressures, the pressure is preferably about 14.7 psi (0.101 MPa) or greater and more preferably about 100 psi (0.689 MPa) or greater. If the reaction is performed at elevated pressures, the pressure is preferably about 1,000 psi (6.89 MPa) or less, more preferably about 600 psi (4.14 MPa) or less and most preferably about 500 psi (3.45 MPa) or less. The reaction time is chosen to facilitate preparing the desired compounds in the desired yield. Preferably, the reaction time is about 12 hours or greater, even more preferably about 18 hours or greater and most preferably about 24 hours or greater. Preferably the reaction time is about 48 hours or less, even more preferably about 36 hours or less and most preferably about 24 hours or less. The catalyst can be any dehydrogenation catalyst which under the reaction conditions abstracts hydrogen from the cyclohexene ring to form an aromatic ring. Preferred dehydrogenation catalysts are based on metals, more preferably Group VIII metals. The metals can be present in pure form, as alloys, in the form of metal oxides or mixtures thereof. The catalysts can also contain modifiers to impact or enhance the catalytic effect or selectivity of the catalyst. Such modifiers are well known in the art. Preferred reaction modifiers are transition metals and compounds containing transition metals. Preferred metals upon which the catalysts are based are platinum, palladium and nickel, with palladium most preferred. The catalyst can be used in a homogeneous manner but is preferably a heterogeneous catalyst on a support. The catalysts can also be in the form of sponge metals which are known to those of skill in the art. The support can be any support useful for heterogeneous catalysts. Among preferred supports are aluminum oxides, spinels, zeolites and carbon. The most preferred supports are carbon supports. The dehydrogenation reaction can be performed in a solvent. Preferably, the reaction is performed at reflux in a solvent. Preferably the solvent has a boiling point at the temperatures of reaction described earlier. Where the reaction is performed in a solvent at reflux, oxygen, preferably in the form of air, may be bubbled through the refluxing solvent. The catalyst is present in a sufficient amount such that the reaction proceeds in a reasonably efficient manner to give the desired product in the desired yield. The catalyst is preferably present in an amount of about 0.01 mole percent or greater based on the amount of the cyclohexene containing compound, more preferably about 0.03 mole percent or greater and most preferably about 1 mole percent or greater. The catalyst is preferably present in an amount of about 10 mole percent or less based on cyclohexene ring containing compound, more preferably about 5 mole percent or less and most preferably about 3 mole percent or less. The product is recovered by any means known in the art which allows isolation of the desired product at the desired yields and purity. Preferred means of recovering the desired products include filtering the reaction medium to remove the catalyst, concentrating the product by evaporation and separating the products recovered by chromatographic separation, distillation, and/or recrystallization from a suitable solvent. Preferably, the yield of products is about 60 percent by weight or greater based on the weight of the starting cyclohexene compound and more preferably about 65 percent by weight or greater. Preferably, the products recovered exhibit a purity of about 90 percent by weight or greater and most preferably about 99 percent by weight or greater. Preferably, the products exhibit a detectable amount of carbon 14, preferably up to about one part per trillion. In a preferred embodiment, the recovered products have greater than about 6 carbon atoms derived from renewable resources such as biomass and more preferably greater than about 8 carbon atoms derived from renewable resources such as biomass.

Preferably, the dehydrogenation is performed in a continuous flow mode. In this embodiment the dehydrogenation is performed at a temperature at which reasonable rates occur. Preferably, the temperature is about 200° C. or greater and more preferably about 300° C. or greater. Preferably, the temperature is about 400° C. or less and more preferably about 350° C. or less. Preferably the dehydrogenation is performed under the flow of an inert gas, preferably nitrogen. Preferably the catalyst is a heterogeneous catalyst and the reactants are flowed through a bed of catalyst. The flow rates, reactions temperatures and concentrations of the reactions impact therate of reaction. The product stream can be recirculated to enhance the product yield.

The reaction of one or more of muconic acid and carboxylate derivatives thereof with one or more dienophiles and the dehydrogenation reaction step may be performed without recovery of the cyclohexene from the solvent after the first reaction step. Both reactions can be performed as described hereinbefore. In the embodiment wherein the reaction of one or more of muconic acid and carboxylate derivatives thereof with one or more dienophiles is performed in the presence of a Lewis Acid, preferably the Lewis Acid is removed prior to dehydrogenation. The dehydrogenation catalyst is added to the reaction mixture containing the cyclohexene compound before the dehydrogenation step is initiated. In this embodiment the solvent is a glycol ether, polyglycol ether, aromatic hydrocarbon, such as xylene, and the like. More preferred solvents are dimethyl glycol ether and xylene. The dehydrogenation catalyst may be added to the reaction at any temperature up to the desired reaction temperature.

In a preferred embodiment the product recovered corresponds to the formula

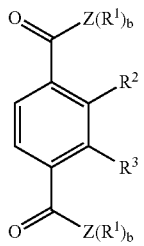

wherein $R^1$, $R^2$, Z and b are as described hereinbefore.

In a more preferred embodiment the product recovered corresponds to the formula

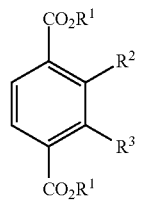

wherein $R^1$ and $R^2$ are as described hereinbefore. In the embodiment wherein the starting dienophile is an unsaturated ester the product is a trimellitate preferably corresponding to the formula

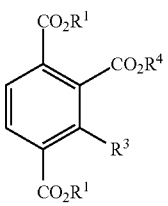

wherein $R^1$, $R^3$ and $R^4$ are as described hereinbefore. In the embodiment wherein the starting dienophile is maleic anhydride the resulting product preferably corresponds to the formula

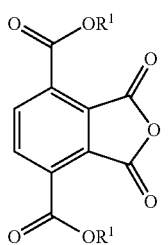

wherein $R^1$, $R^3$ and $R^4$ are as described hereinbefore. Wherein the starting dienophile used to make the cyclohexene was an aromatic compound with an unsaturated subsituent the product preferably corresponds to the formula

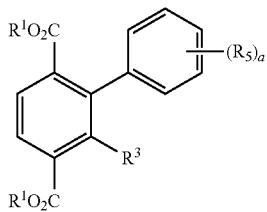

wherein $R^1$, $R^3$ and $R^5$ are as described hereinbefore.

To prepare cyclohexane based compounds from the cyclohexene compounds prepared by the reaction of muconic acid and/or carboxylate derivatives thereof with dienophiles as described herein the cyclohexene compounds are subjected to hydrogenation. In the hydrogenation step, the cyclohexene compounds are contacted with hydrogen in the presence of one or more hydrogenation catalysts. Suitable temperatures are those at which hydrogen is inserted to the cyclohexene compound to remove double bonds in the ring at a reasonable rate. Preferably, the cylcohexene compound is contacted with hydrogen and one or more hydrogenation catalysts at ambient temperature. The reaction can be performed at atmospheric and elevated pressures. The upper limit on elevated pressures is the capability of the reaction equipment to handle the pressures. Preferably the pressure is less than about 200 psi (1.38 MPa). Preferably, pressure is applied by adding hydrogen gas to achieve the desired pressures. At atmospheric pressure hydrogen is bubbled through the reaction medium and/or the reaction mixture is stirred under atmospheric pressure. The reaction time is chosen to facilitate preparing the desired compounds in the desired yield. Preferably the reaction time is about 0.5 hours or greater, more preferably about 1.0 hour or greater and most preferably about 2.0 hours or greater. Preferably the reaction time is about 24 hours or less, more preferably about 16 hours or less, most preferably about 8 hours or less, and most preferably about 3 hours or less. The catalyst can be any hydrogenation catalyst which under the reaction conditions inserts hydrogen to the cyclohexene ring to form a cyclohexane ring. Preferred hydrogenation catalysts are based on metals, preferably Group VIII metals. The metals can be present in pure form, as alloys, in the form of metal oxides or mixtures thereof. The catalysts can also contain modifiers to impact or enhance the catalytic effect or selectivity of the catalyst. Such modifications are well known in the art. Preferred metals upon which the catalysts are based are platinum, palladium and nickel, with palladium most preferred. The catalyst can be used in a homogeneous manner but is preferably a heterogeneous catalyst on a support. The catalysts may also be sponge metal catalysts known to those skilled in the art. The support can be any support useful for heterogeneous catalysts. Among preferred supports are aluminum oxides, spinels, zeolites and carbon. The most preferred support is carbon. The hydrogenation reaction can be performed in a solvent. Among preferred solvents are chlorinated hydrocarbons, acyclic ethers, cyclic ethers and alcohols (such as alkanols and acetyl alcohol), and the like. Preferably, cyclohexene compounds are present in an amount of about 5 percent by weight or greater based on the solvent and most preferably about 8 percent by weight or greater. Preferably, the cyclohexene compounds are present in an amount of about 15 percent by weight or less based on the solvent and most preferably about 12 percent by weight or less. The catalyst is present in a sufficient amount such that the reaction proceeds in a reasonably efficient manner to give the desired product in the desired yield. The catalyst is preferably present in an amount of about 0.01 mole percent or greater based on the amount of the cyclohexene containing compound, more preferably about 0.03 mole percent or greater and most preferably about 1.0 mole percent or greater. The catalyst is preferably present in an amount of about 10.0 mole percent or less based on cyclohexene ring containing compound, more preferably about 5.0 mole percent or less and most preferably about 3.0 mole percent or less. The product is recovered by any means known in the art which allows isolation of the desired product at the desired yields and purity. Preferred means of recovering the desired product (here cyclohexane ring containing compounds) in the desired yield include filtering the reaction medium to remove the catalyst, concentrating the product by evaporation and separating the products recovered by chromatographic separation, distillation, and/or recrystallization from a suitable solvent. Preferably, the yield of cyclohexane ring containing compounds is about 0.90 percent by weight or greater based on the weight of the starting cyclohexene compound and more preferably about 99 percent by weight or greater. Preferably, cyclohexane ring containing compounds recovered exhibit a purity of about 90 percent by weight or greater and most preferably about 99 percent by weight or greater. Preferably, the cyclohexane ring containing compounds exhibit a detectable amount of carbon 14, preferably up to about one part per trillion. In a preferred embodiment, the recovered cyclohexane ring containing compounds have about 6 or greater carbon atoms derived from renewable resources such as biomass and more preferably about 8 greater carbon atoms derived from renewable resources such as biomass.

In a preferred embodiment the hydrogenated product recovered corresponds to the formula

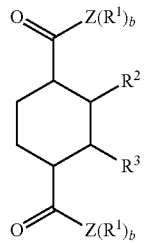

wherein $R^1$, $R^2$, Z and b are as described hereinbefore.

In a more preferred embodiment the hydrogenated product recovered corresponds to the formula

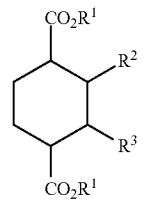

wherein $R^1$ and $R^2$ are as described hereinbefore. In the embodiment wherein the starting dienophile is an unsaturated ester the product is a cyclohexane preferably corresponding to the formula

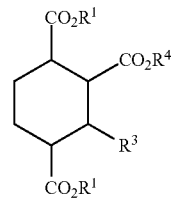

wherein $R^1$, $R^3$ and $R^4$ are as described hereinbefore. In the embodiment wherein the starting dienophile is maleic anhydride, the resulting product preferably corresponds to the formula

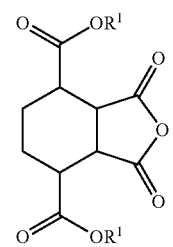

wherein $R^1$, $R^3$ and $R^4$ are as described hereinbefore. Wherein the starting dienophile used to make the cyclohexane was an aromatic compound with an unsaturated subsituent, the product preferably corresponds to the formula

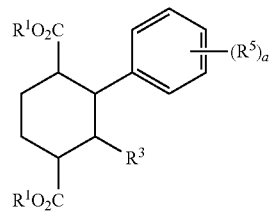

wherein $R^1$, $R^3$ and $R^5$ are as described hereinbefore.

The cyclohexane compounds having carboxylate groups at the 1 and 4, and optionally the 2, positions may be subjected to conditions to convert the carboxylate groups to methylol groups. Such conditions are well known in the art. In one embodiment the cyclohexane compounds having carboxylate groups at the 1 and 4, and optionally the 2, positions may be subjected to catalytic hydrogenation under conditions such that the carboxylate groups are converted to methylol groups, as disclosed in section 20.22 of *Organic Chemistry*, 4$^{th}$ ed. Morrsion and Boyd, Allyn and Bacon, New York, 1983, incorporated herein by reference. Generally, higher pressures and temperatures are utilized for hydrogenation of carboxylate groups. Alternatively, the carboxylate groups may be converted to methylol groups by chemical reduction as disclosed in Morrison and Boyd, supra. Generally, the cyclohexane compounds having carboxylate groups at the 1 and 4, and optionally the 2, positions are contacted with sodium metal and alcohol or with lithium aluminum hydride. In yet another embodiment, the conversion is achieved by contacting the cyclohexane compounds having carboxylate groups at the 1 and 4, and optionally the 2, positions with acid at elevated temperatures according to Advance Organic Chemistry, 2d, Edition March, McGraw Hill, New York 1977. In another embodiment the process of U.S. Pat. No. 4,302,595, incorporated hereinby reference, may be utilized. The cyclohexane compounds having carboxylate groups at the 1 and 4, and optionally the 2, positions, preferably correspond to the formula;

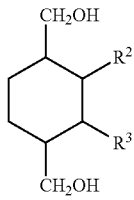

wherein $R^2$ may comprise a methylol group where the starting compound had carboxylate at the 2 position.

The benzene, cyclohexene and cyclohexane compounds having carboxylic acid groups at the 1 and 4, and optionally the 2, positions; can be esterified to add hydrocarbyl groups at the 1 and 4, and optionally the 2, positions to form carboxylate groups at these positions. The esterification reaction can be performed by any esterification process known to those skilled in the art including the processes discloses at March, ibid, pages 363 to 365 and the processes disclosed hereinbefore. In one embodiment an esterifying agent, an alcohol as described hereinbefore, is contacted with the benzene, cyclohexene and cyclohexane compounds having carboxylic acid groups at the 1 and 4, and optionally the 2, positions in the presence of a strong acid with removal of the water and ester formed or a significant excess alcohol. The acidic catalysts are described hereinbefore.

The compounds prepared in this invention can be used as monomers to prepare a variety of known polymers. Some of the compounds can be used as plasticizers for various polymeric systems. The phenyl substituted terephthalates may be used to prepare liquid crystal polymers as described in U.S. Pat. No. 4,391,966, relevant disclosure incorporated herein be reference. The benzene, cyclohexene and cyclohexane compounds having carboxylic acid groups at the 1 and 4, and optionally the 2, positions, preferably terephthalic acid or dimethyl terephthalates, can be reacted with alkylene glycols, such ethylene glycol or 1,4-butane diol, to prepare polyesters. Processes for preparing such polyesters are well known in the art. For instance, terephthalic acid can be reacted with ethylene glycol to prepare polyethylene terephalate as described in "Contemporary Polymer Chemistry" Second Edition, Harry R. Alcock, Frederick W. Lampe, 1990, Prentice-Hall at pages 27 and 28, incorporated herein by reference. In one embodiment the invention relates to methods for preparing polyalkylene polyester comprising a) contacting cis-cis muconic acid and one or more isomerization catalysts, sources of ultraviolet radiation, or both in a solvent at elevated temperatures for a period of time such that the cis-cis muconic acid isomerizes to trans-trans muconic acid; b) recovering the trans-trans muconic acid; c) optionally, contacting the trans-trans muconic acid with one or more esterifying agents in the presence of one or more strong acids under conditions such that one or more trans-trans dihydrocarbyl muconates are formed; d) contacting one or more trans-trans muconic acid or dihydrocarbyl muconates with one or more dienophiles at elevated temperatures under conditions such that the one or more muconic acid dihydrocarbyl muconates and dienophiles form one or more cyclohexene ring containing compounds; and e) contacting the cyclohexene ring containing compounds with one or more alkylene glycols under conditions such that one or more polyalkylene polyesters are prepared.

In another embodiment the invention relates to methods for preparing polyalkylene polyesters comprising a) contacting cis-cis muconic acid and one or more isomerization catalysts, sources of ultraviolet radiation, or both in a solvent at elevated temperatures for a period of time such that the muconic acid isomerizes to trans-trans muconic acid; b) recovering the trans-trans muconic acid; c) optionally, contacting the trans-trans muconic acid with one or more esterifying agents in the presence of one or more strong acids under conditions such that one or more trans-trans dihydrocarbyl muconates are formed; d) contacting one or more trans-trans muconic acids or dihydrocarbyl muconates with one or more dienophiles at elevated temperatures under conditions such that the one or more muconic acids or dihydrocarbyl muconates and dienophiles form one or more cyclohexene ring containing compounds; and e) contacting the cyclohexene ring containing compounds with a hydrogenation catalyst under conditions such that one or more cyclohexane compounds having carboxylic acid groups at the 1 and 4, and optionally the 2, positions are prepared; f) contacting one or more cyclohexane compounds having carboxylic acid groups at the 1 and 4, and optionally the 2, positions with one or more alkylene glycols under conditions such that one or more polyalkylene polyesters are prepared. In one embodiment the invention relates to methods for preparing polyalkylene terephthalate comprising a) contacting cis-cis muconic acid and one or more isomerization catalysts, sources of ultraviolet radiation, or both in a solvent at elevated temperatures for a period of time such that the cis-cis muconic acid isomerizes to trans-trans muconic acid; b) recovering the trans-trans muconic acid; c) optionally, contacting the trans-trans muconic acid with one or more esterifying agents in the presence of one or more strong acids under conditions such that one or more trans-trans dihydrocarbyl muconates are formed; d) contacting one or more trans-trans muconic acids or dihydrocarbyl muconates with one or more dienophiles at elevated temperatures under conditions such that the one or more muconic acids or dihydrocarbyl muconates and dienophiles form one or more cyclohexene ring containing compounds; and e) contacting the cyclohexene ring containing compounds with a dehydrogenation catalyst, optionally in the presence of an oxidant, under conditions such that one or more of terephthalic acid or dihydrocarbyl terephthalates are prepared; f) contacting one or more of terephthalic acid or dihydrocarbyl terephthalates with one or more alkylene glycols under conditions such that one or more polyalkylene terephthalates are prepared. In another embodiment the invention is a method for preparing polyethylene terephthalate comprising a) contacting cis-cis muconic acid and iodine, a source of ultraviolet radiation or both in a solvent at elevated temperatures for a period of time such that the cis-cis muconic acid isomerizes to trans-trans muconic acid; b) recovering the trans-trans muconic acid; c) contacting the trans-trans muconic acid with methanol in the presence of one or more strong acids under conditions such that trans,trans dimethyl muconate is formed; d) contacting trans-trans dimethyl muconate with ethylene at elevated temperatures under conditions such that dimethyl cyclohex-2-ene-1,4-dicarboxylate, and/or its 1-ene-tautomer, is prepared; e) contacting the dimethyl cyclohex-2-ene-1,4-dicarboxylate with a dehydrogenation catalyst, optionally in the presence of an oxidant under conditions such that dimethyl terephthalate is prepared; f) hydrolyzing dimethyl terephthalate to form terephthalic acid; and g) contacting terephthalic acid with ethylene glycol under conditions such that polyethylene terephthalate is prepared. In yet another embodiment the invention is a method for preparing polyethylene terephthalate comprising a) contacting cis-cis muconic acid and iodine, a source of ultraviolet radiation or both in a solvent at elevated temperatures for a period of time such that the cis-cis muconic acid isomerizes to trans-trans muconic acid: b) recovering the trans-trans muconic acid; c) contacting trans-trans muconic acid with ethylene at elevated temperatures under conditions such that cyclohex-2-ene-1,4-dicarboxylic acid, and/or its 1-ene tautomer, is prepared; d) contacting the cyclohex-2-ene-1,4-dicarboxylic acid with a dehydrogenation catalyst, optionally in the presence of an oxidant, under conditions such that terephthalic acid is prepared; and e) contacting terephthalic acid with ethylene glycol under conditions such that polyethylene terephthalate is prepared. The invention also includes a method for preparing polybutylene terephthalate comprising a) contacting cis-cis muconic acid and iodine, a source of ultraviolet radiation or both in a solvent at elevated temperatures for a period of time such that the cis-cis muconic acid isomerizes to trans-trans muconic acid; b) recovering the trans-trans muconic acid; c) contacting the trans-trans muconic acid with methanol in the presence of one or more strong acids under conditions such that trans,trans dimethyl muconate is formed; d) contacting trans-trans dimethyl muconate with ethylene at elevated temperatures under conditions such that dimethyl cyclohex-2-ene-1,4-dicarboxylate, and/or its 1-ene tautomer, is prepared; e) contacting the dimethyl cyclohex-2-ene-1,4-dicarboxylate with a dehydrogenation catalyst, optionally in the presence of an oxidant, under conditions such that dimethyl terephthalate is prepared; f) contacting dimethyl terephthalate with 1,4-butanediol under conditions such that polybutylene terephthalate is prepared. The resulting polyesters contain at least about 6 carbons per monomer unit, and preferably at least about 8 carbon atoms, derived from renewable resources, that are from muconic acid or muconic acid and ethylene precursors. In a preferred embodiment the resulting polyesters contain a detectable amount of carbon 14 and preferably up to about 1 part per trillion. This invention relates to polyesters wherein a portion, up to and including all, of the benzene, cyclohexene and cyclohexane compounds having carboxylic acid groups at the 1 and 4, and optionally the 2, positions used to prepare the polyesters are synthesized from one or more of muconic acid or carboxylate derivatives thereof derived from biomass. The muconic acid or carboxylate derivatives thereof may be derived from biomass by microbial synthesis. The benzene, cyclohexene and cyclohexane compounds having carboxylic acid groups at the 1 and 4, and optionally the 2, positions used to prepare the polyesters may be synthesized from ethylene derived from a renewable resource. The benzene, cyclohexene and cyclohexane compounds having carboxylic acid groups at the 1 and 4, and optionally the 2, positions used to prepare the polyesters may be synthesized from one or more of muconic acid or carboxylate derivatives thereof derived from biomass and from ethylene derived from a renewable resource. In another embodiment, the diol, such as ethylene glycol and butanediol, reacted with the benzene, cyclohexene and cyclohexane compounds having carboxylic acid groups at the 1 and 4, and optionally the 2, positions may be derived from renewable resources, such as biomass or derivatives thereof, as is known in the art. In this embodiment, the number of carbon atoms in each monomer unit derived from renewable resources may be about 10 or greater or about 12 or greater.

The novel compounds of the invention and those prepared by the novel processes of the invention are preferably derived from renewable resources. Compounds prepared from renewable resources exhibit a characteristic $^{13}C/^{12}C$ ratio as described in U.S. Pat. No. 7,531,593 Column 6 line 60 to column 8 line 42, incorporated herein by reference.

It is understood that the above description is intended to be illustrative and not restrictive. Many embodiments as well as many applications besides the examples provided will be apparent to those of skill in the art upon reading the above description. It is further intended that any combination of the features of different aspects or embodiments of the invention may be combined. The explanations and illustrations presented herein are intended to acquaint others skilled in the art with the invention, its principles, and its practical application. Those skilled in the art may adapt and apply the invention in its numerous forms, as may be best suited to the requirements of a particular use. Accordingly, the specific embodiments of the present invention as set forth are not intended as being exhaustive or limiting of the invention. The scope of the invention should, therefore, be determined not with reference to the above description, but should instead be determined with reference to the appended claims, along with the full scope of equivalents to which such claims are entitled. Other combinations are also possible as will be gleaned from the following claims, which are also hereby incorporated by reference into this written description. The omission in the following claims of any aspect of subject matter that is disclosed herein is not a disclaimer of such subject matter, nor should it be regarded that the inventors did not consider such subject matter to be part of the disclosed inventive subject matter.

Specific Embodiments

Unless otherwise stated, all parts and percentages are by weight.

Purification of cis,cis Muconic Acid

EXAMPLE 1

Purification of Crude cis,cis Muconic Acid

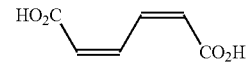

In two separate 125 ml Erlenmeyer flask, a suspension in each of crude cis,cis muconic acid (10.0 g each for a total of 20.0 g) in methanol (50 ml) is heated to reflux with a heat-gun. The hot suspension is filtered. Additional methanol (30 ml) is added to the residue. It is heated again to reflux and filtered through the same filter paper into the same round-bottom flask. All solid present on the filter paper is now moved back into the Erlenmeyer flask, additional methanol (30 ml) is added and the heating to reflux followed by filtering sequence is repeated. The combined methanol solution (110 ml) is allowed to cool to room temperature, then placed into an ice bath. After warming to room temperature overnight, the mother liquid is decanted to reveal a microcrystalline beige solid, which after drying under high vacuum weights 4.84 g. This exact sequence is now repeated with the second 10 g batch of cis,cis-muconic acid to obtain 4.23 g. The mother liquids from both recrystallizations are then combined and evaporated to dryness. A single recrystallization of the remaining residue from methanol (75 ml) yields an additional 2.82 g. In total, 11.89 g (59 percent mass recovery) of pure cis,cis muconic acid.

EXAMPLE 2

Purification of Crude Muconic Acid

A stirred suspension of dried (less than 5 weight percent of water), crude cis,cis or cis,trans muconic acid (200 g) in tetrahydrofuran (THF) (1.8 liter (l)) is heated to 50° C. Within 45 minutes at 50° C. most of the solid dissolves. Activated charcoal (35 g) is added. After 1 hour, the hot suspension is clarified by filtration through a bed of Celite™ diatomaceous earth. The filtrate is evaporated to dryness and the residue is dried under high vacuum to yield pure cis,cis or cis,trans muconic acid (166 g, 83 percent mass recovery). In the case of cis,cis muconic acid, any traces of cis,trans muconic acid can be removed by resuspending the solid twice in refluxing ethyl acetate, which is removed each time by decantation from the cooled solution. The approximate solubilities at room temperature in ethyl acetate are 1 mg/ml for cis,cis muconic acid, 5 mg/ml for cis,trans muconic acid, and 0.1 mg/ml for trans,twins muconic acid.

Isomerization to Cis,Trans and Trans,Trans Muconic Acid

EXAMPLE 3

Synthesis of Cis,Trans Muconic Acid from Crude Cis,Cis Muconic Acid

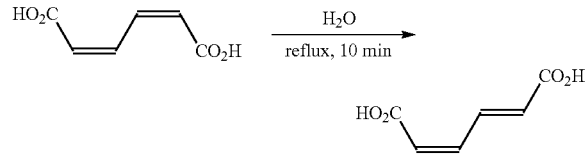

Crude cis,cis muconic acid (15.0 g) suspended in water (250 ml) is heated to reflux for 10 minutes using a heat gun. At reflux, everything is in solution. The hot solution is allowed to cool to room temperature, and then placed into an ice bath. After warming to room temperature overnight, the mother liquid is decanted to reveal pure cis,trans muconic acid as a microcrystalline beige solid, which after drying under high-vacuum weighs 9.0 g, giving a 60 percent mass recovery.

EXAMPLE 4

Synthesis of Cis,Trans Muconic Acid from Pure Cis,Cis Muconic Acid

An aqueous (150 ml) suspension of purified cis,cis muconic acid (15.0 g) is heated to reflux for 15 minutes using a heat gun. After cooling to room temperature overnight, the precipitated solid, pure cis,trans muconic acid, is collected by filtration, washed with a small amount of water, and dried under high vacuum (10.4 g, 69 percent). A sample of the mother liquid is concentrated, and the entire remaining residue is dissolved in DMSO-$d_6$ for NMR analysis. The bulk of the mother liquid is evaporated to dryness (4.2 g). Based on integration of the $^1$H NMR spectrum of the evaporation residue of the mother liquid sample, 3 percent of the total muconic acid remained in solution as the cis,trans isomer, 25 percent is converted to its internal lactone, and the remaining 3 percent undergoes lactone-hydrolysis followed by decarboxylation to form laevulinic acid.

EXAMPLE 5

Synthesis of Trans,Trans Muconic Acid from Pure Cis,Cis or Cis,Trans Muconic Acid A mixture consisting of purified cis,cis or cis,trans muconic acid (12.5 g, 88 mmol), $I_2$ (110 mg, 0.5 mol percent), and THF (110 ml, 0.8 M) is refluxed for 4 hours. After cooling to room temperature, the precipitated solid, pure trans, trans muconic acid, is collected by filtration. To remove all traces of $I_2$, the solid is resuspended on the frit in room temperature THF, which is again removed via aspirator vacuum filtration. The material is dried under high vacuum (11.3 g, 90 percent).

EXAMPLES 6 to 13

Synthesis of Trans,Trans Muconic Acid from Crude Cis,Cis or Cis,Trans Muconic Acid Dried, purified cis,cis muconic acid (5.0 g, 35.2 mmol) is suspended in THF (44 ml, 0.8 M). Either pure water (1, 5, 10, or 20 weight percent) or $(NH_4)_2SO_4$ (1, 5, 10, or 20 weight percent) is added. $I_2$ (45 mg, 0.5 mol percent) is added and the mixture is heated to reflux for 4 hour. After cooling to room temperature, the precipitated trans,trans muconic acid is collected by filtration and dried. In the case of the $(NH_4)_2SO_4$ experiments, the mass of collected trans,trans muconic acid is corrected for the presence of $(NH_4)_2SO_4$. A sample of the mother liquid is concentrated and all of the residue is dissolved in DMSO-$d_6$ for $^1$H NMR analysis. Integration allowed an estimation of the composition of the mother liquid. The results are compiled in Tables 1 and 2

Tables 1 and 2:

| Ex | added H$_2$O (weight %) | tt-MA isolated (g) | tt-MA isolated (% yield) | composition of the mother liquid | | |
|---|---|---|---|---|---|---|
| | | | | % tt-MA | % ct-MA | % lactone |
| 6 | 1 | 4.1 | 82 | 94 | 4 | 2 |
| 7 | 5 | 4.5 | 90 | 95 | 3 | 2 |
| 8 | 10 | 4.2 | 84 | 93 | 6 | 2 |
| 9 | 20 | 4.2 | 84 | 82 | 13 | 5 | tt-MA = trans-trans muconic acid,
ct-MA = cis-trans muconic acid.

| Ex | added H$_2$O (weight %) | tt-MA isolated (g) | tt-MA isolated (% yield) | composition of the mother liquid | | | |
|---|---|---|---|---|---|---|---|
| | | | | % tt-MA | % ct-MA | % cc-MA | % lactone |
| 10 | 1 | 3.9 | 78 | 30 | 45 | 25 | traces |
| 11 | 5 | 3.1 | 62 | 24 | 65 | 11 | 1 |
| 12 | 10 | 3.0 | 60 | 21 | 73 | 5 | 1 |
| 13 | 20 | 2.5 | 50 | 15 | 79 | 4 | 2 | tt-MA = trans-trans muconic acid,
ct-MA = cis-trans muconic acid,
cc-MA = cis-cis muconic acid.

EXAMPLE 14

Synthesis of Cis,Trans-Muconic Acid from Crude Cis,Cis-Muconic Acid

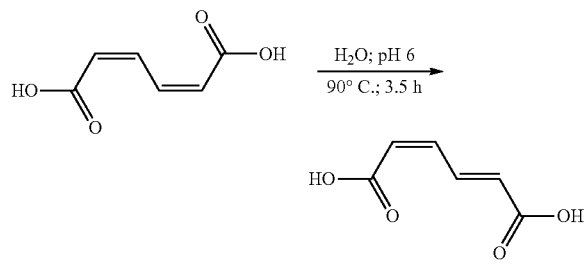

Cis,cis-Muconic acid (100 g) is dissolved in water (1 L, then adjusted to pH 6 by adding base, sodium hydroxide) and the mixture is heated at 90° C. for 3.5 hours. Samples are taken every 30 minutes and analyzed by HPLC. HPLC analyses of these samples show that the isomerization process is almost complete after 1 hour of heating at 90° C. After 3.5 hours of heating at 90° C., the mixture is treated with charcoal (10 g) for 30 minutes and filtered through a Whatman filter paper (#2). The pH of the solution is adjusted to 3.5 by adding base, sodium hydroxide. The precipitate is obtained by filtration, washed with ice-cold water (200 mL), and dried under reduced pressure to yield 64.5 g (65 percent yield) of light yellow cis,trans-muconic acid.

EXAMPLE 15

Synthesis of Trans,Trans Muconic Acid from Cis,Cis Muconic Acid

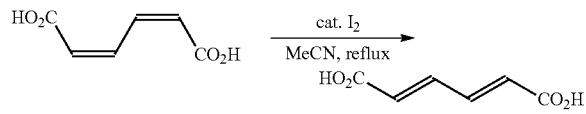

A mixture containing purified cis,cis muconic acid (0.50 g), a catalytic amount of iodine (25 mg), and acetonitrile (35 ml) is heated to reflux for 36 hours. The reaction is performed in the presence of ambient light in the laboratory. The precipitated solid is filtered off from the still hot solution and washed with cold acetonitrile. After drying under high vacuum, 0.40 g (80 percent yield) of pure trans,trans muconic acid are present as a tan-colored powder.

EXAMPLE 16

Synthesis of Trans,Trans Muconic Acid from Cis,Trans Muconic Acid

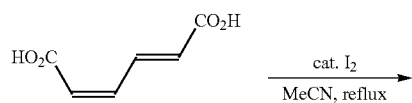

-continued

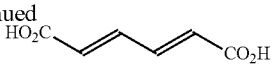

A mixture containing cis, trans muconic acid (1.00 g), a catalytic amount of iodine (53 mg, 3.0 mole percent), and acetonitrile (35 ml) is heated to reflux for 11 hours. The reaction is performed in the presence of ambient light in the laboratory. After cooling to room temperature, the precipitated solid is filtered off and washed with acetonitrile. After drying under high vacuum, 0.80 g (80 percent yield) of pure trans, trans muconic acid are present as a tan-colored powder. The material obtained by this procedure from cis,trans muconic acid is identical to the material obtained from cis,cis muconic acid by the previous procedure.

EXAMPLE 17

Synthesis of Trans,Trans-Muconic Acid from Cis,Trans-Muconic Acid

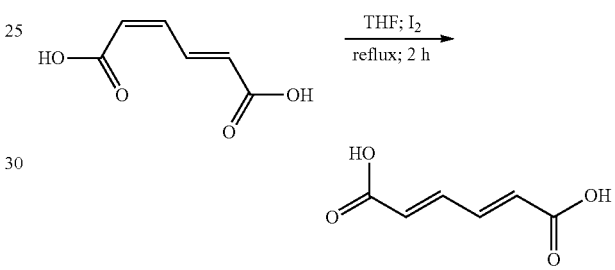

Cis,trans muconic acid (10 g, 70.4 mmol) is dissolved in THF (200 mL) along with 200 mg of iodine (1.1 mole percent). The reaction is performed in the presence of ambient light in the laboratory. The mixture is then brought to reflux and samples are taken every 30 minutes to be analyzed by HPLC. After 2 hours of reflux, the precipitate is filtered, washed with excess THF, and dried to yield 6.2 g of light yellow solid. HPLC analysis of the isolated solid indicated that it is pure trans, trans-muconic acid and that the isomerization is completed after 1 hour of reflux.

EXAMPLE 18

Synthesis of Trans,Trans-Muconic Acid from Cis,Trans-Muconic Acid

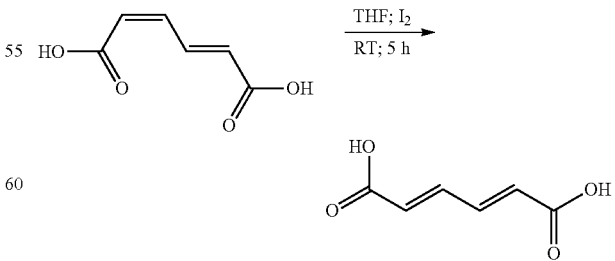

Cis,trans-muconic acid (19 g, 133.8 mmol) is dissolved in THF (250 mL) at room temperature and a crystal of iodine (160 mg, 0.63 mmol, 0.5 mole percent) is added. The reaction is performed in the presence of ambient light in the laboratory. The reaction mixture is allowed to stir at room temperature for 5 hours and the precipitant is filtered, washed with acetonitrile and dried under reduced pressure to yield 16 g of trans, trans-muconic acid, an 84 percent yield.

Esterification of Muconic Acid

EXAMPLE 19

Synthesis of Cis,Cis Dimethyl Muconate from Cis,Cis Muconic Acid

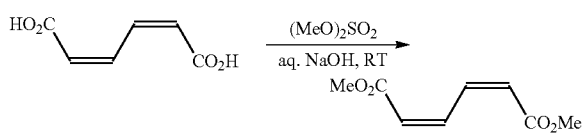

Purified cis,cis muconic acid (10.0 g, 70.4 mmol) is suspended in aqueous sodium hydroxide (NaOH, 42.2 ml, 5.0 M, 211 mmol, 3.0 equivalents). At room temperature, dimethyl sulfate (18.4 ml, 194 mmol, 2.75 equivalents) is added after 15 min and the mixture is rapidly stirred for 6 hours. The mixture is taken up in ethyl acetate and shaken until all solid is dissolved. The organic phase is reextracted 3 times with 1 M (molar) aqueous NaOH and once with saturated aqueous sodium chloride (NaCl). Drying with magnesium sulfate (MgSO$_4$), filtering, and evaporation of all solvent yields an off-white crystalline solid (6.2 g, 36.4 mmol, 52 percent yield) which is identified as pure cis,cis dimethyl muconate, free of any dimethyl sulfate.

EXAMPLE 20

Synthesis of Cis,Trans Dimethyl Muconate from Cis,Trans Muconic Acid

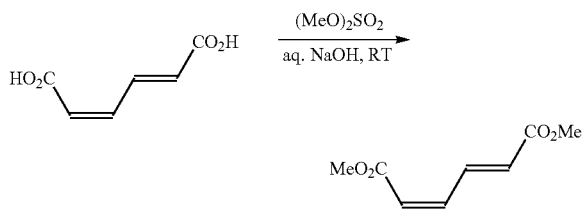

Purified cis,trans muconic acid (10.0 g, 70.4 mmol) is suspended in aqueous NaOH (42.2 ml, 5.0 M, 211 mmol, 3.0 equivalents). At room temperature, dimethyl sulfate (18.4 ml, 194 mmol, 2.75 equivalents) is added after 15 minutes and the mixture is rapidly stirred for 5 hours. The mixture is taken up in ethyl acetate and shaken until all solid is dissolved. The organic phase is reextracted 3 times with 1 M aqueous NaOH and once with saturated aqueous NaCl. Drying with magnesium sulfate (MgSO$_4$), filtering, and evaporation of all solvent yields an off-white crystalline solid (6.0 g, 35.3 mmol, 50 percent yield) which is identified as pure cis, trans dimethyl muconate, free of any dimethyl sulfate.

EXAMPLE 21

Synthesis of Isomeric Dimethyl Muconates from Cis,Cis Muconic Acid

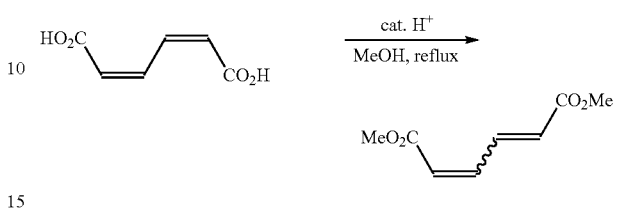

Cis,cis muconic acid (10.0 g, 70.4 mmol) is suspended in methanol (250 ml). A catalytic amount of H$_2$SO$_4$ (0.6 ml) is added and the reaction mixture is refluxed for 18 hours. After concentration, the remaining brown residue is taken up in ethyl acetate and extracted 3 times with saturated aqueous K$_2$CO$_3$. Drying (Na$_2$SO$_4$), filtering, and evaporation of all solvent results in a light brown solid (10.8 g, 63.5 mmol, 90 percent yield), consisting mainly of cis,cis and cis,trans dimethyl muconate, which is used as described hereinafter without further purification.

EXAMPLE 22

Synthesis of Trans,Trans Dimethyl Muconate from Trans,Trans Muconic Acid

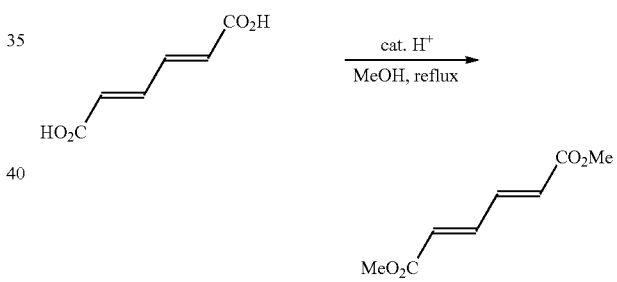

Trans,trans muconic acid (4.6 g, 32.4 mmol) is suspended in methanol (125 ml). A catalytic amount of sulfuric acid, H$_2$SO$_4$ (0.3 ml) is added and the reaction mixture is refluxed for 18 hours. After concentration, the remaining brown residue is taken up in ethyl acetate and extracted 3 times with saturated aqueous potassium carbonate, aq. K$_2$CO$_3$. Drying over sodium sulfate (Na$_2$SO$_4$), filtering, and evaporation of all solvent yields an off-white solid (5.2 g, 30.6 mmol, 94 percent yield), which is identified as pure trans,trans dimethyl muconate.

EXAMPLE 23

Synthesis of Trans,Trans Dimethyl Muconate from Trans,Trans Muconic Acid

Concentrated H$_2$SO$_4$ (0.52 ml, 0.1 volume percent) is added to a stirred suspension of trans,trans muconic acid (60 g, 0.42 mol) in methanol (0.52 l, 0.8 M). The reaction mixture is stirred at reflux for 16 hours. This reaction transforms a low solubility solid into another low solubility solid. The density of crystalline trans,trans dimethyl muconate is higher than that of crystalline trans,trans muconic acid: trans,trans muconic acid is suspended throughout the stirring methanol reaction mixture whereas trans,trans dimethyl muconate remains accumulated on the bottom of the flask at all investigated stirring rates. After cooling to room temperature, the mother liquid is decanted and the precipitate is washed with methanol. To remove all traces of $H_2SO_4$, fresh methanol (200 ml) is introduced and the mixture is heated to reflux for 10 minutes. After cooling to room temperature, the mother liquid is again decanted and the precipitate is washed with methanol. Drying under high vacuum provides clean trans, trans dimethyl muconate (68 g, 0.40 mol, 95 percent).

EXAMPLE 24

Synthesis of Trans,Trans Di-n-Butyl Muconate from Trans,Trans Muconic Acid

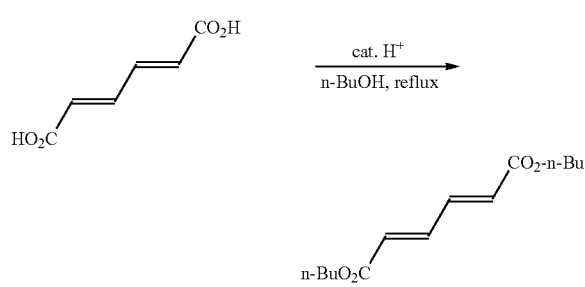

Trans,trans muconic acid (5.0 g, 35.2 mmol) is suspended in normal butanol (40 ml). A catalytic amount of $H_2SO_4$ (0.45 ml) is added and the reaction mixture is refluxed for 16 hours. The reaction mixture is diluted with ethyl acetate and extracted 3 times with saturated aqueoud. $K_2CO_3$. Drying ($Na_2SO_4$), filtering, and evaporation of all solvent yields a light yellow gel (8.3 g, 32.7 mmol, 93 percent yield), which is identified as pure trans,trans di-n-butyl muconate.

EXAMPLE 25

Synthesis of Trans,Trans Di-(2-Ethyl-Hexyl) Muconate from Trans,Trans Muconic Acid

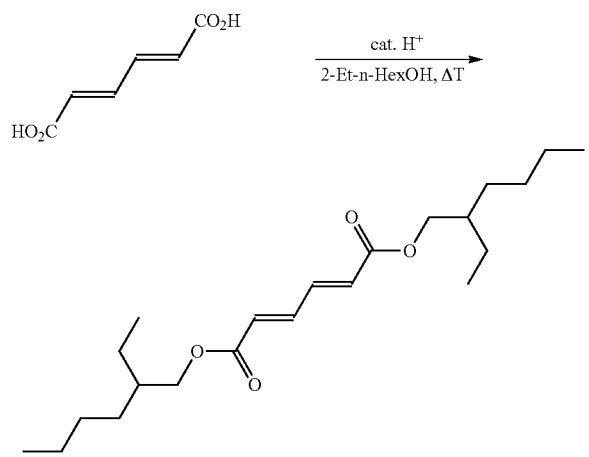

Trans,trans muconic acid (5.0 g, 35.2 mmol) is suspended in 2-ethyl-hexanol (50 ml). A catalytic amount of $H_2SO_4$ (0.45 ml) is added and the reaction mixture is refluxed for 18 hours. Most of the solvent is evaporated and via a short chromatographic separation ($SiO_2$, hexanes as the eluent) a light yellow oil (11.2 g, 30.6 mmol, 87 percent yield) is obtained, which is identified as pure trans,trans di-(2-ethyl-hexyl) muconate.

Isomerization of Cis, Cis and Cis,Trans Dimethyl Muconate to Trans,Trans Dimethyl Muconate

EXAMPLE 26

Synthesis of Trans,Trans Dimethyl Muconate from Cis,Cis Dimethyl Muconate

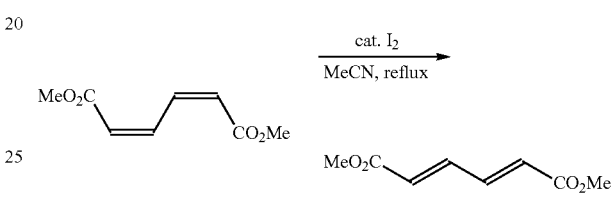

A solution of cis,cis dimethyl muconate (0.60 g, 3.43 mmol) and a catalytic amount of iodine (30 mg, 3.3 mole percent) in acetonitrile (10 ml) is heated to reflux for 15 hours. The reaction is performed in the presence of ambient light in the laboratory. Removal of all solvent on a rotary evaporator followed by high vacuum, washing with 15 ml diethyl ether and hexane in a 3/2 volumetric ratio to remove all of the iodine, and drying under high vacuum yields an off-white crystalline solid (0.58 g, 3.41 mmol, 97 percent yield), which is identified as pure trans,trans dimethyl muconate.

EXAMPLE 27

Synthesis of Trans,Trans Dimethyl Muconate from Cis,Trans Dimethyl Muconate

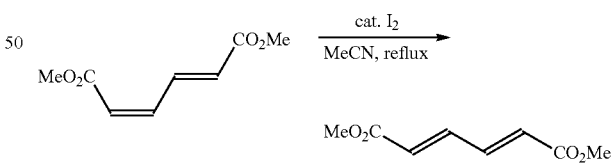

A solution of cis,trans dimethyl muconate (0.60 g, 3.53 mmol) and a catalytic amount of iodine (43 mg, 4.8 mole percent) in acetonitrile (10 ml) is heated to reflux for 25 hours. The reaction is performed in the presence of ambient tight in the laboratory. Removal of all solvent on a rotary evaporator is followed by applying a high vacuum, washing with 15 ml diethyl ether and hexane in a 3/2 volumetric ratio to remove all iodine, and drying under high vacuum yields an off-white crystalline solid (0.60 g, 3.53 mmol, 100 percent yield) which is identified as pure trans,trans dimethyl muconate.

EXAMPLE 28

Synthesis of Trans,Trans Dimethyl Muconate from the Isomeric Dimethyl Muconates

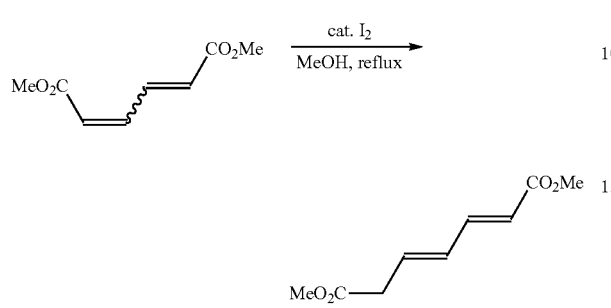

A solution of the mixture of cis,cis and cis,trans dimethyl muconate (10.8 g, 63.5 mmol) obtained in Example 21 and a catalytic amount of $I_2$ (300 mg, 1.9 mol percent) in methanol (250 ml) is heated to reflux for 60 hours, at which time TLC and GC-MS confirms complete conversion. Upon cooling to 0° C., trans,trans dimethyl muconate precipitates. It is collected by filtration, washed with ice-cold methanol, and dried under high vacuum (8.2 g, 48.2 mmol, 76 percent yield). The material obtained by this procedure is identical to the material obtained by the previous two procedures.

Reactions of Trans,Trans Muconic Acid and Trans, Trans Dimethyl Muconate

EXAMPLE 29

Reaction of Trans,Trans Dimethyl Muconate and Maleic Anhydride

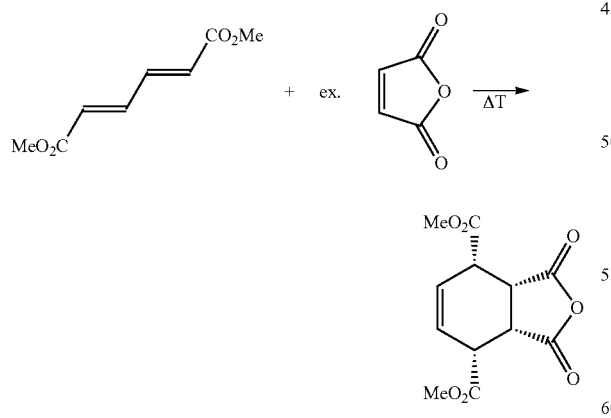

In a 5 ml pressure tube, trans,trans dimethyl muconate (1.0 g, 5.9 mmol) and maleic anhydride (1.7 g, 17.6 mmol, 3 eq.) are heated to 150° C. for 1 hour. $^1$H NMR analysis of the cooled reaction mixture reveals the presence of about 79 percent desired addition product.

EXAMPLE 30

Reaction Between Cis,Cis Dimethyl Muconate and Maleic Anhydride

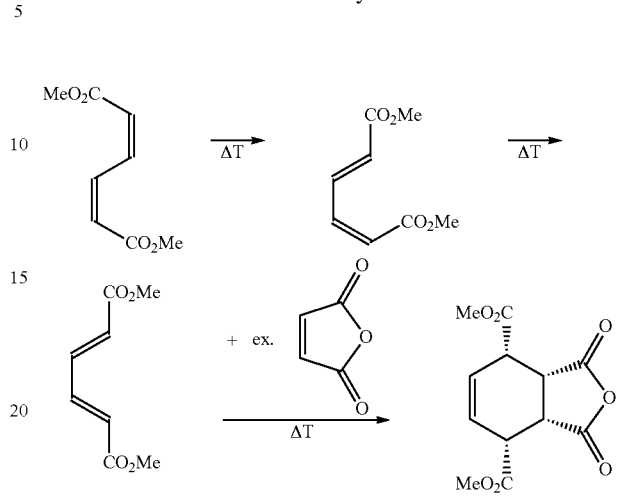

A solution of cis,cis dimethyl muconate (0.1 g, 0.6 mmol) and maleic anhydride (173 mg, 1.8 mmol, 3 eq.) in decahydronaphthalene (2 ml) is heated to 150° C. for 24 hours. All of the cooled reaction mixture is dissolved in DMSO-$d_6$ for $^1$H NMR analysis, showing the presence of about 60 percent unreacted cis,cis dimethyl muconate, 20 percent isomerized trans,trans dimethyl muconate, and 20 percent of the Diels-Alder addition product between trans,trans dimethyl muconate and maleic anhydride.

EXAMPLE 31

Reaction Between Cis,Trans Dimethyl Muconate and Maleic Anhydride

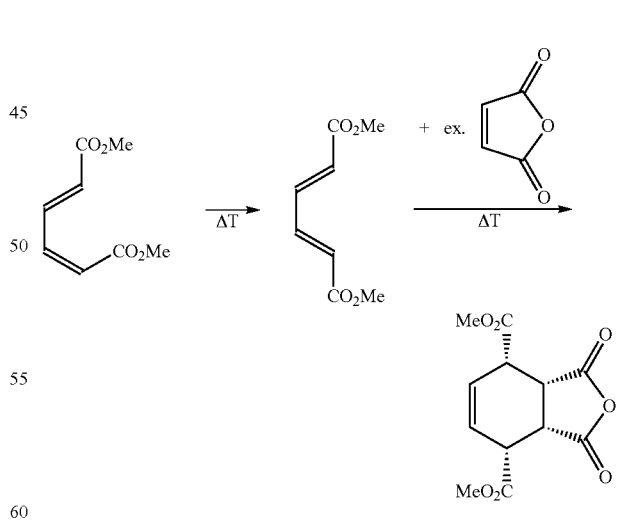

A solution of cis,trans dimethyl muconate (0.1 g, 0.6 mmol) and maleic anhydride (173 mg, 1.8 mmol, 3 eq.) in decahydronaphthalene (2 ml) is heated to 150° C. for 24 hours. All of the cooled reaction mixture is dissolved in DMSO-$d_6$ for $^1$H NMR analysis, showing the presence of about 69 percent unreacted cis,trans dimethyl muconate, 9 percent isomerized trans,trans dimethyl muconate, and 22 percent of the addition product between trans,trans dimethyl muconate and maleic anhydride.

EXAMPLE 32

Preparation of Trimethyl Trimellitate Via Reaction Between Trans,Trans Dimethyl Muconate and Methyl Propiolate

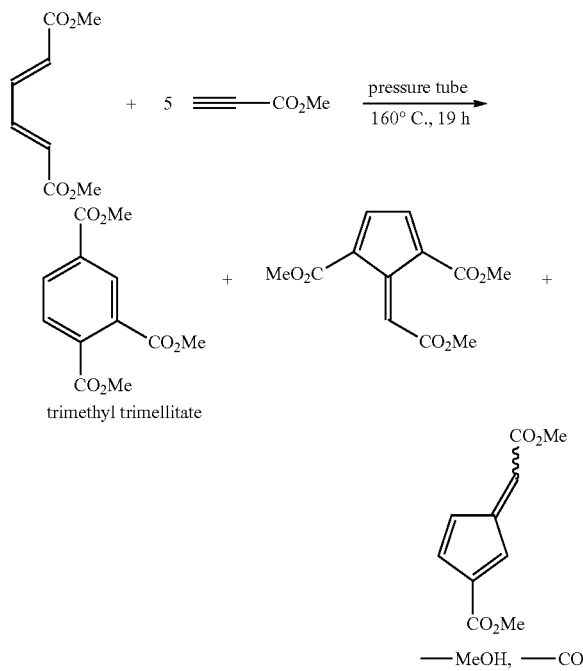

In a 5 ml pressure tube, a solution of trans,trans dimethyl muconate (1.0 g, 5.9 mmol) in methyl propiolate (2.5 ml, 29.4 mmol, 5 eq.) is heated to 160° C. for 19 hour. NMR analysis of the cooled reaction solution reveals that no unreacted trans, trans dimethyl muconate remains. Three substances are found to be present in near equal quantities. Repeated column chromatography (Si35, SF25-40 g, AnaLogix column with 13 percent ethyl acetate/hexane isocratic eluent) of the crude reaction mixture, and analysis of single fractions, allows the identification of the three distinct reaction products: trimethyl trimellitate (23 percent), arising by an oxidation of the initially formed diene product, dimethyl 2-(2-methoxy-2-oxoethylidene)cyclopenta-3,5-diene-1,3-dicarboxylate (29 percent), arising from a cheletropic addition (end-on) of the alkyne to the diene followed by oxidation, and an E/Z mixture of methyl 3-(2-methoxy-2-oxoethylidene)cyclopenta-1,4-dienecarboxylate (27 percent), arising from an attack of the alkyne onto the β-carbon of the ene, followed by methanol elimination to form a cumulene which undergoes rearrangement under expulsion of CO. Similar experiments with cis,cis and cis,trans dimethyl muconate only produce the products derived from trans,trans dimethyl muconate due to initial isomerization to trans,trans dimethyl muconate followed by addition.

EXAMPLE 33

Diels-Alder Reaction Between Trans,Trans Muconic Acid and Acrylic Acid

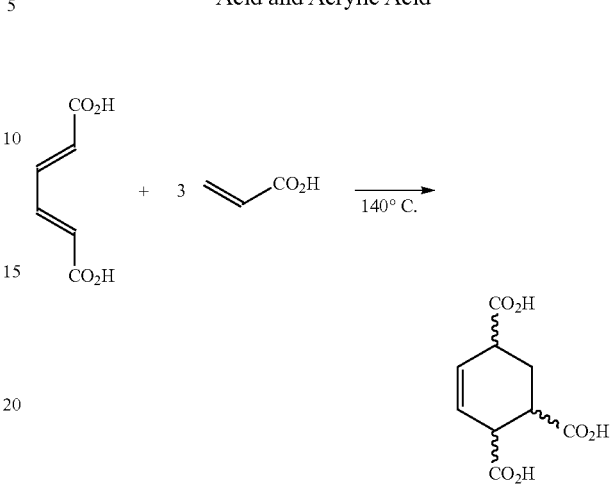

A stirred mixture of trans,trans muconic acid (1.0 g, 7.0 mmol) and acrylic acid (0.96 ml, 14.0 mmol, 2.0 eq.) in a 5 ml round-bottom flask equipped with a reflux condenser is heated to 140° C. for 3 hours. To achieve a larger amount of conversion, more acrylic acid is added over the course of the reaction (1.0 eq. at 2 hours). In order to facilitate the characterization of the product, the reaction mixture is esterified in methanol overnight. GC-MS analysis of the crude esterified product shows the presence of trimethyl cyclohex-5-ene-1,2, 4-tricarboxylate, thus confirming the formation of cyclohex-5-ene-1,2,4-tricarboxylic acid via reaction between trans, trans muconic acid and acrylic acid.

EXAMPLE 34

Preparation of Trimethyl Cyclo-5-ene-1,2,4-tricarboxylate

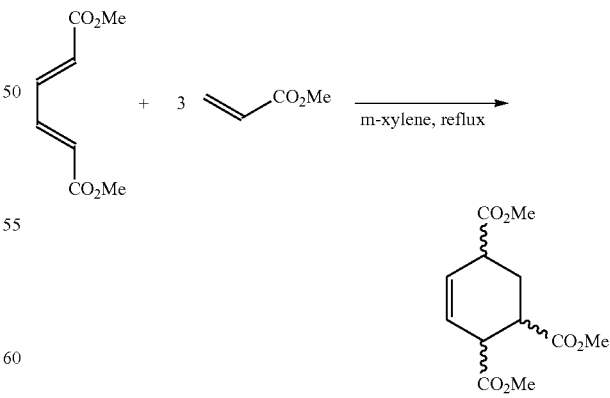

Trans,trans dimethyl muconate (1 g, 5.9 mmol), methyl acrylate (1.6 ml, 17.6 mmol, 3 eq) and hydroquinone (65 mg, 0.59 mmol, 0.1 eq) are mixed in m-xylene (30 ml). The reaction mixture is refluxed under nitrogen for 72 hours. The reaction

EXAMPLE 35

Preparation of 2-butyl-1,4-dimethyl Cyclo-5-ene-1,2,4-tricarboxylate

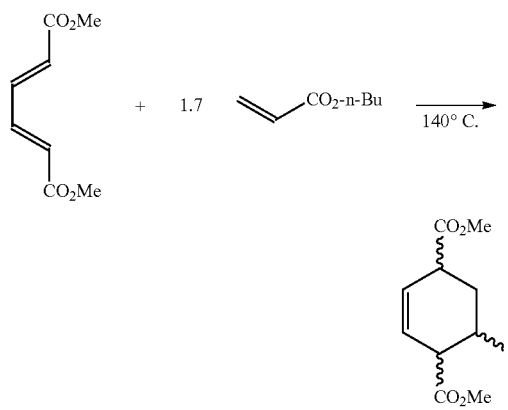

Trans,trans dimethyl muconate (1 g, 5.9 mmol) is mixed with butyl acrylate (0.85 ml, 5.9 mmol, 1.0 eq) and hydroquinone (65 mg, 0.59 mmol, 0.1 eq). The reaction mixture is heated to 140° C. for 1 hour. After one hour, 0.5 equivalents of butyl acrylate (0.42 ml, 2.9 mmol) are added to the mixture and it is heated for an additional hour. Then, 0.2 equivalents of butyl acrylate (0.17 ml, 1.2 mmol) are added to the reaction mixture, which is heated for one more hour. After a total of 3 hours, the reaction mixture is allowed to cool down to room temperature. The excess butyl acrylate is evaporated and the resulting residue is purified by column chromatography using an Analogix BSR SimpliFlash system (Hexanes/Ethyl acetate, 8:2). The desired product is obtained as a mixture of two diastereomers of the expected Diels-Alder addition product with an 81 percent yield (1.4 g, 4.8 mmol, clear gel).

mixture is then concentrated down to a clear colorless gel, which is purified by column chromatography using the Analogix BSR SimpliFlash system (Hexanes/Ethyl acetate, 8:2). A mixture of the two diastereomers of the desired product is isolated as a clear colorless and colorless oil with a 61 percent yield, 0.9 g, 3.6 mmol.

EXAMPLE 36

Preparation of Tributyl Cyclo-5-ene-1,2,4-tricarboxylate

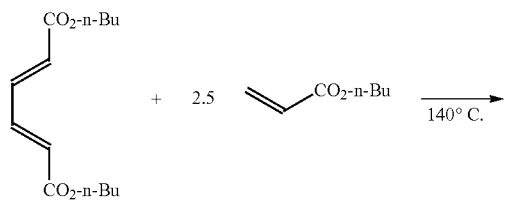

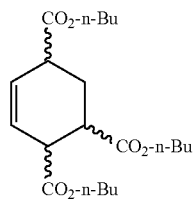

A stirred mixture of trans,trans di-n-butyl muconate (1.0 g, 3.9 mmol) and n-butyl acrylate (0.85 ml, 5.9 mmol, 1.5 eq.) with hydroquinone (0.1 eq) in a 5 ml round-bottom flask equipped with a reflux condenser is heated to 140° C. for 4 hours. To achieve a larger amount of conversion, more n-butyl acrylate is added over the course of the reaction (1.0 eq. at 3 hours). The cooled reaction mixture is purified by column chromatography (Si35, SF25-40 g, AnaLogix column with 10 percent ethyl acetate/hexane isocratic eluent) to provide two diastereomers of the expected addition product (1.1 g, 3.0 mmol, 78 percent yield) as a clear light-yellow oil.

EXAMPLE 37

Preparation of Tri-(2-ethyl-hexyl) Cyclohex-5-ene-1,2,4-tricarboxylate

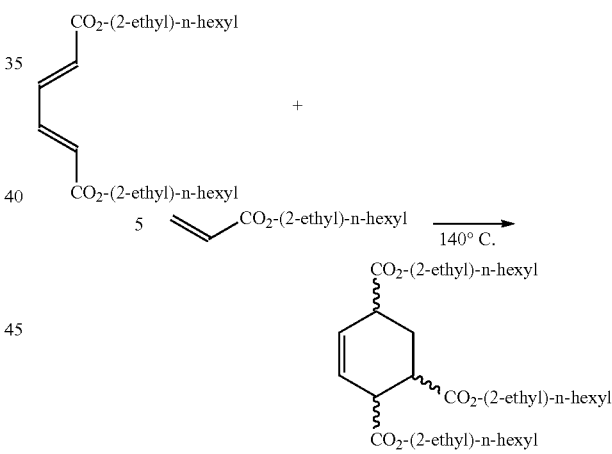

A stirred mixture of trans,trans di-(2-ethyl-hexyl) muconate (1.0 g, 2.7 mmol), 2-ethyl-hexyl acrylate (1.1 ml, 5.4 mmol, 2.0 eq.), and hydroquinone (30 mg, 0.27 mmol, 0.1 eq.) in a 5 ml round-bottom flask equipped with a reflux condenser is heated to 140° C. for 4 hours. To achieve a larger amount of conversion, more 2-ethyl-hexyl acrylate is added over the course of the reaction (2.0 eq. at 1 h, 1.0 eq. at 3 hours). The cooled reaction mixture is purified by column chromatography (Si35, SF25-40 g, AntiLogix column, gradient: 100 percent hexanes to 20 percent ethyl acetate/hexanes) to provide two diastereomers of the addition product (0.72 g, 1.3 mmol, 49 percent yield) in the form of a clear light-yellow oil. When this reaction is run in the absence of hydroquinone, the same two diastereomers of the addition product are formed.

EXAMPLE 38 to 40

Preparation of dimethyl cyclohex-2-ene-1,4-dicarboxylate

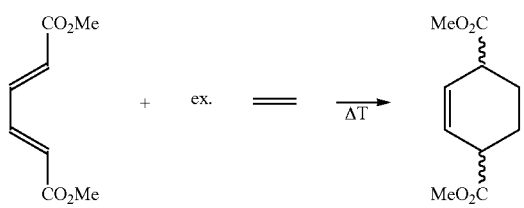

In a Parr pressure reactor, a rapidly stirred solution of trans,trans dimethyl muconate (2.58 g, 15.2 mmol) in m-xylene (120 ml) is heated under an ethylene atmosphere (260 psi at 23° C. after the solution is saturated with ethylene) at a 150° C. set-point temperature (151-168° C. observed) for 24 hours. $^1$H NMR analysis of the near-colorless cooled reaction solution revealed about 96 percent conversion to dimethyl cyclohex-2-ene-1,4-dicarboxylate. Removal of the solvent provided a white-cloudy oil. The precipitated traces of trans,trans dimethyl muconate are separated by taking up the oil in tert-butyl-methyl-ether and filtering it to provide, after removal of the solvent, an over 98 percent pure product (near-colorless oil). Another batch is purified by column chromatography (Si35, SF25-40 g, AnaLogix column with 13 percent ethyl acetate/hexane isocratic eluent) to obtain an analytical sample. Diastereomers of dimethyl cyclohex-2-ene-1,4-dicarboxylate are detected by GC. As shown in the following table, the reaction can also be conduced successfully on a larger scale and also with free trans,trans muconic acid (Examples 41-42). Table 3 shows the amount of dimethyl muconate, pressure (psi), c(M), solvent, set and reaction temperatures, reaction time in hours and the result of the reaction. In Examples 41 and 42 the trans,trans muconic acid is the starting material instead of trans,trans dimethyl muconate.

EXAMPLES 41 and 42

Reaction Between Free Trans,Trans Muconic Acid and Ethylene

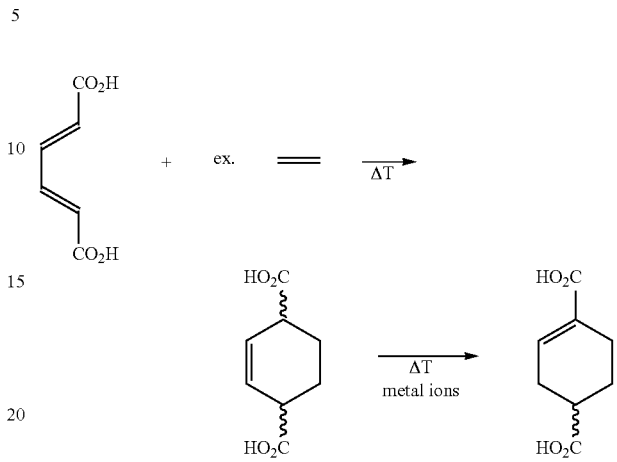

In a Parr pressure reactor, a rapidly stirred (155 rpm) mixture of trans,trans muconic acid (2.10 g, 14.7 mmol) and water (120 ml) is heated under an ethylene atmosphere (270 psi at 23° C. after the solution was saturated with ethylene) at a 150° C. set-point temperature for 3 days. After opening the cooled Parr reactor, an orange solid is present on the ground of a yellow solution. The yellow solution is decanted and the orange solid is dried (paper towel) to provide 0.85 g (5.0 mmol, 34 percent yield). $^1$H NMR analysis identifies it to be the tautomerized ethylene-Diels-Alder addition product. An additional quantity of the tautomerized product was present in the yellow solution. In addition, the yellow solution also contained a small quantity of the untautomerized initial Diels-Alder addition product and decomposed material. A subsequent reaction (Example 42) at 125° C. for 1 day shows that at such lower temperature more (44 percent) untautomerized initial Diels-Alder addition product is present at the time the reaction is worked-up; in addition, 13 percent tautomerized product is present, 41 percent unreacted starting material was recovered, and only 2 percent decomposed material is present. The results of Examples 38 to 42 are shown in Table 3.

TABLE 3

| Ex | M g | P psi | Solvent | c(M) | T ° C. | t d | y percent | Remarks |
|---|---|---|---|---|---|---|---|---|
| 38 | 2.6 | 270 | m-xylene | 0.12 | 150 | 1 | 96 | |
| 39 | 7.6 | 260 | m-xylene | 0.36 | 150 | 2 | 98 | |
| 40 | 2.1 | 250 | n-butanol | 0.12 | 150 | 3 | 74 | n-butyl carboylate product, and 26 percent di n-butyl muconate |
| 41 | 2.1 | 270 | water | 0.12 | 150 | 3 | >34 | >0.85 g (>34 percent) of tautomerized DAp |
| 42 | 2.1 | 270 | water | 0.12 | 125 | 1 | 44 | 13 percent of tautomerized DAp |

M muconate amount in grams c(M) means molar concentration of muconate in solvent.

T is temperature in degrees centigrade.

t is reaction time in days.

y is yield in weight percent.

DAp is Diels Alder product.

EXAMPLES 43 to 47

One-Pot Isomerization and Diels-Alder Followed by Esterification

The reaction sequence is shown in FIG. 1. In a Parr pressure reactor, a stirred suspension of cis,cis muconic acid (8.6 g, 60.6 mmol) and $I_2$ (114 mg, 0.7 mol percent) in diglyme (diglycol methyl ether, 120 ml, 0.5 M) is heated under ethylene pressure (270 psi (1.86 MPa) at 23° C.) to 200° C. for 48 hours. All solvent is removed, and methanol (200 ml) and a catalytic amount of concentrated $H_2SO_4$ (0.2 ml) are added. After reflux for 14 hours, the solution is analyzed by GC to quantify the amounts of dimethyl cyclohex-2-ene-1,4-dicarboxylate (13-19 percent) and dimethyl cyclohex-1-ene-1,4-dicarboxylate (74-76 percent) present. Removal of the solvent and distillation provides clean product. The results are shown in Table 4.

TABLE 4

| Ex | solvent | catalyst/ mol % | T (° C.) | % yield eq-ax $Me_2$-$\Delta^2$ | bis-eq $Me_2$-$\Delta^2$ | $Me_2$-$\Delta^1$ |
| --- | --- | --- | --- | --- | --- | --- |
| 43 | diglyme | $I_2$, 0.6 | 165 | 60 | | 9 |
| 44 | diglyme | $I_2$, 0.7 | 200 | 8 | 11 | 76 |
| 45 | diglyme | none | 200 | 3 | 4 | 4 |
| 46 | MeOH | $I_2$, 0.7 | 200 | 9 | 7 | 5 |
| 47 | diglyme | $I_2$, 0.7 | 200 | 13 | | 74 |

EXAMPLE 48

Synthesis of Dimethyl Cyclohex-2-ene-1,4-dicarboxylate from trans,trans Dimethyl Muconate—Larger Scale In a Parr pressure reactor, a stirred suspension of trans,trans dimethyl muconate (40.8 g, 240 mmol) in diglyme (120 ml, 2.0 M) is heated under ethylene pressure (270 psi (1.86 MPa) at 23° C.) to 165° C. for 24 hours. Analysis of the reaction mixture by GC allows quantification of the products; dimethyl cyclohex-2-ene-1,4-dicarboxylate (75 percent) and dimethyl cyclohex-1-ene-1,4-dicarboxylate (1 percent) are present. Removal of the solvent and distillation provides clean product.

EXAMPLE 49

One Step Cis,Trans Dimethyl Muconate Isomerization to Trans,Trans Dimethyl Muconate and Reaction with Ethylene

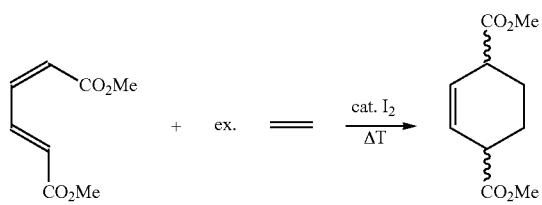

In a Parr reactor, a mixture of cis,trans dimethyl muconate (9.80 g, 57.6 mmol), iodine (73 mg, 0.29 mmol, 0.5 mol percent), and dioxane (120 ml, 0.48 M) is heated to 160° C. for 24 hours under ethylene pressure ($p_{RT}$=270 psi (1.86 MPa)). After cooling to room temperature, a weakly yellow, cloudy suspension is present. All solvent is evaporated on a rotary evaporator from a sample of this suspension to reveal a colorless oil with a yellow solid suspended in it. All of this material is dissolved in dimthylsulfoxide (DMSO-$D_6$) and analyzed by $^1$H NMR spectroscopy: 86 percent of dimethyl cyclohex-2-ene-1,4-dicarboxylate is found to be present.

EXAMPLE 50

One Step Cis,Trans Muconic Acid Isomerization to Trans,Trans Muconic Acid and Reaction with Ethylene

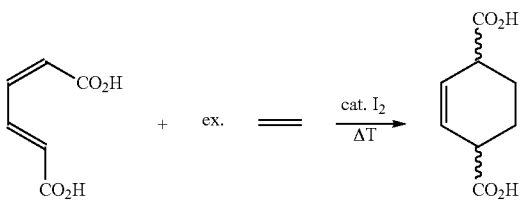

In a Parr reactor, a mixture of cis,trans muconic acid (8.18 g, 57.6 mmol), $I_2$ (293 mg, 1.15 mmol, 2.0 mole percent), and THF (120 ml, 0.48 M) is heated to 160° C. for 25 hours under ethylene pressure ($p_{RT}$=252 psi (1.74 MPa)). After cooling to room temperature, a white solid is found to be suspended in a weakly yellow solution. The solution is filtered to remove the precipitated trans,trans muconic acid and all solvent is evaporated on a rotary evaporator. The residue is suspended in hot ethyl acetate/dioxane; after cooling to room temperature, the precipitated solid is removed by filtration and the filtrate is evaporated to dryness to yield cyclohex-2-ene-1,4-dicarboxylic acid (7.22 g, 42.4 mmol, 75 percent).

Oxidation to Terephthalic Acid and its Esters

EXAMPLE 51

Preparation of Terephthalic Acid by Oxidation of the Reaction Products Between Trans,Trans Muconic Acid and Ethylene

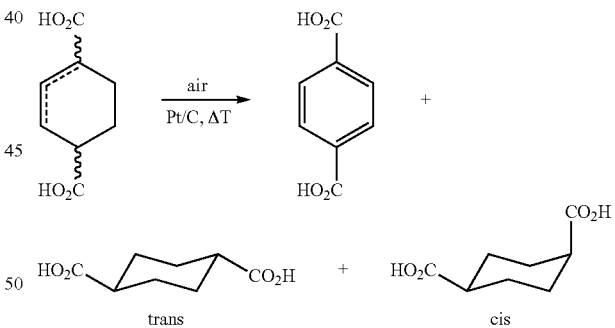

In a Parr pressure reactor, the product of example 50 (0.85 g, 5.0 mmol) is suspended in $H_2O$ (120 ml, 0.04 M) and Pt/C (390 mg, 5 percent Pt/C, 2 mole percent Pt) powder is added. The reactor is pressurized with air (240 psi at 23° C. after saturation of the liquid phase) and its contents heated to 150° C. set-point temperature for 3 days under rapid stirring (155 rpm). After opening the cooled Parr reactor, a white solid, partly submerged under the aqueous Pt/C suspension, is present on the surface of the glass reaction vessel. The combined material is filtered and repeatedly washed using copious quantities of hot methanol to provide, after concentration to dryness, a near white solid (0.43 g). NMR analysis shows the presence of 55 percent terephthalic acid, 40 percent trans-, and 5 percent cis-cyclohexane-1,4-dicarboxylic acid.

EXAMPLE 52

Preparation of Dimethyl Terephthalate—Oxidation with Air at Normal Pressure

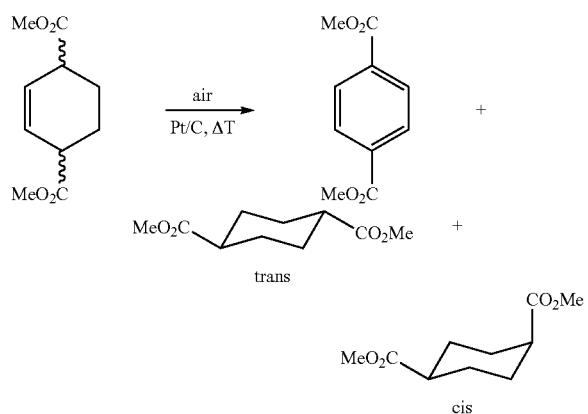

Air is bubbled through a refluxing solution of dimethyl cyclohex-2-ene-1,4-dicarboxylate (0.25 g, 1.26 mmol) in acetic acid (20 ml) containing a catalytic amount of platinum on carbon powder (200 mg, 5 percent Pt/C, 10 mg Pt, 4 mole percent) for a period of 87 hours. $^1$H NMR analysis of the cooled reaction suspension reveals about 69 percent conversion to the desired oxidation product. Filtration and removal of the solvent provides a near-white solid (0.24 g). Purification by column chromatography (Si35, SF40-80 g, AnaLogix column with 13 percent ethyl acetate/hexane isocratic eluent) provides an analytical sample of dimethyl terephthalate.

EXAMPLE 53

Preparation of Dimethyl Terephthalate—Oxidation with Air in a Parr Reactor

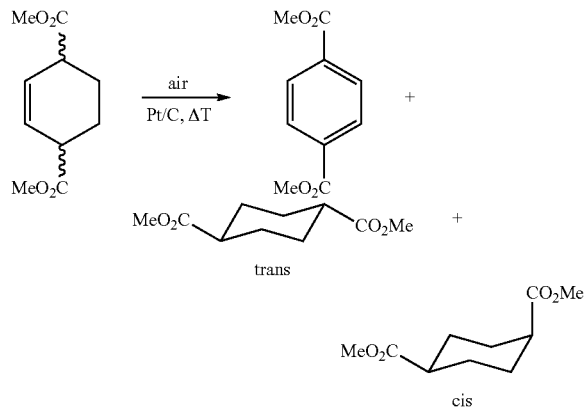

In a Parr pressure reactor, dimethyl cyclohex-2-ene-1,4-dicarboxylate (2.42 g, 12.2 mmol) is dissolved in cyclohexane (120 ml, 0.10 M) and a catalytic amount of platinum on carbon (476 mg, 5 percent Pt/C, 1 mole percent platinum) powder is added. The reactor is pressurized with air (240 psi (1.65 MPa)) at 23° C. after saturation of the solution) and its contents are heated at a 150° C. set-point temperature for 3 days under rapid stirring (160 rpm). After opening the cooled Parr reactor, a suspension of black platinum on carbon (Pt/C) in a near colorless solution is present. All solvent is removed from a sample of the suspension, and the entire residue is dissolved in CDCl$_3$ for $^1$H NMR analysis. Integration of the respective resonances shows the presence of about 23 percent unreacted dimethyl cyclohex-2-ene-1,4-dicarboxylate starting material, of about 59 percent dimethyl terephthalate oxidation product, and of about 18 percent dimethyl cyclohexane-1,4-dicarboxylate disproportionation by-product. Column chromatography (Si35, SF40-150 g, AnaLogix column with 10 percent ethyl acetate/hexane isocratic eluent) provides pure dimethyl terephthalate.

EXAMPLE 54

Reaction of Trans,Trans Dimethyl Muconate with Ethylene and Dehydrogenation in the Same Solvent

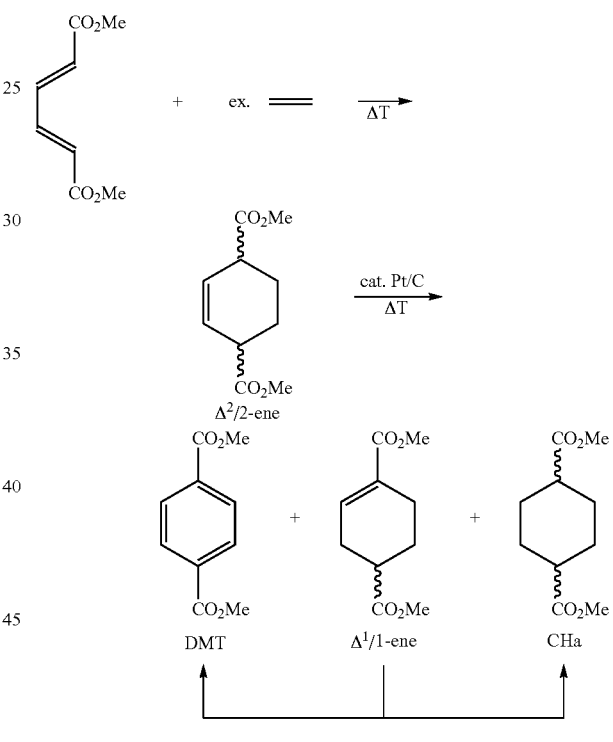

Figure 2:
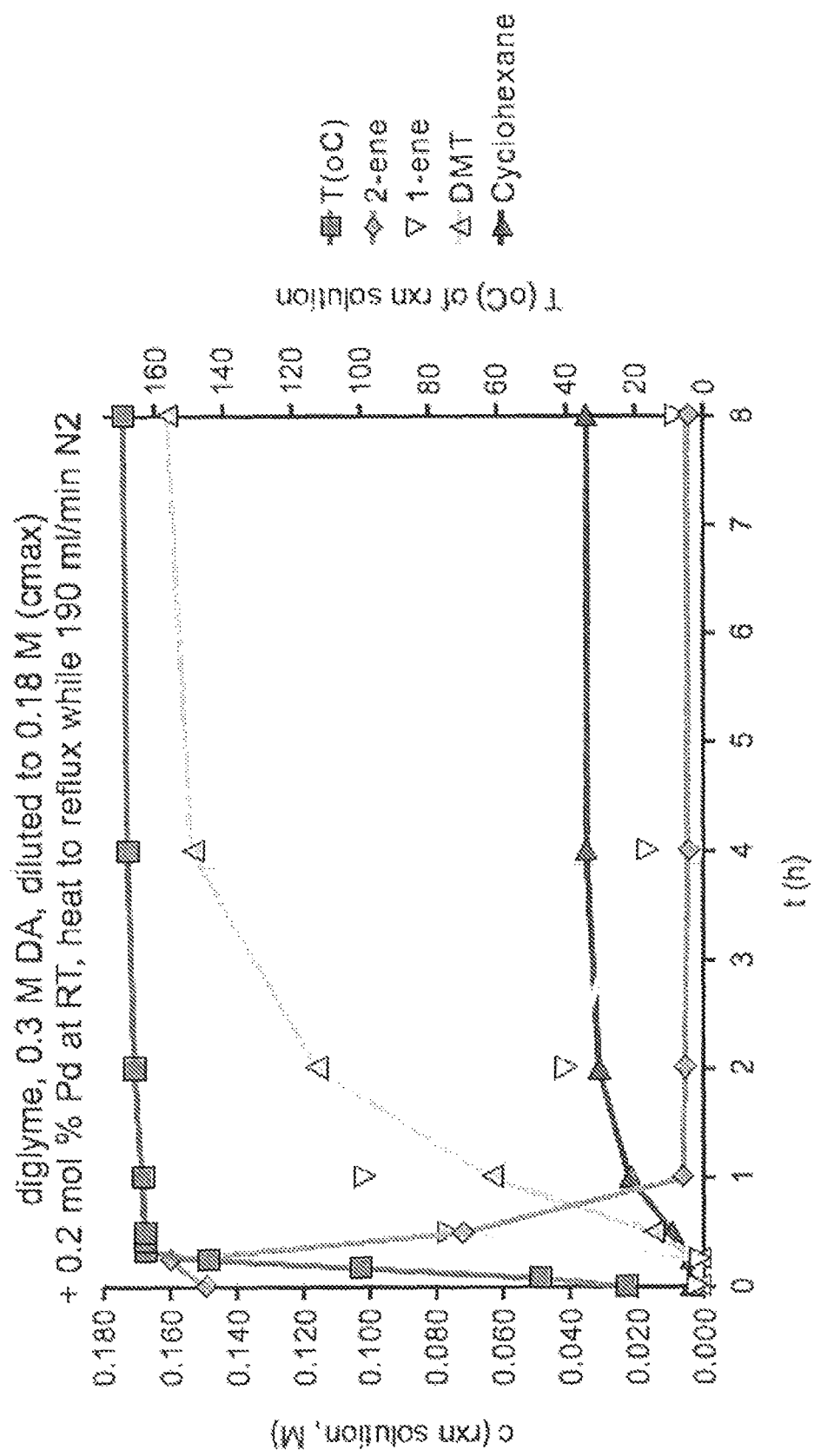
FIG. 2 shows the concentration of materials at various time intervals in Example 54.

In a Parr reactor, a mixture of trans,trans dimethyl muconate (6.13 g, 36.0 mmol) and diglyme (120 ml, 0.30 M) is heated to 165° C. for 24 hours under ethylene pressure ($p_{RT}$=259 psi (1.79 MPa)). After cooling to room temperature, the weakly yellow, clear solution is diluted using diglyme to 200 ml in a volumetric flask, transferred into a round-bottom flask equipped with a magnetic stirring bar, and catalytic palladium on carbon (Pd/C) is added (356 mg of Johnson-Matthey 5 percent Pd/C #6, 0.2 mole percent) at room temperature. The flask is equipped with a reflux condenser, fritted gas dispersion tube, and internal Temperature probe. Under N$_2$ flow (190 ml/min) and stirring (190 rpm) the mixture is heated to reflux ($T_{max,observed}$=169° C.) while samples were taken at appropriate intervals (i=0.0, 0.25, 0.5, 1.0, 2.0, 4.0, 8.0 h) to monitor the progress of the reactions occurring. Rapid (t≦1 h) disappearance of the dimethyl cyclohex-2-ene-1,4-dicarboxylate, $\square^2$, 2-ene is observed concurrent with some material undergoing tautomerization to its thermodynamically more stable isomer (dimethyl cyclohex-1-ene-1,4-dicarboxylate, $\square^1$, 1-ene), while also the desired oxidation/dehydrogenation/aromatization product dimethyl terephthalate (DMT) and some reduced material (dimethyl cyclohexane-1,4-dicarboxylate CHa) are formed. After 8 hours reaction time, 77 percent DMT, 17 percent cyclohexane, and 5 percent tautomer are present. The graph of FIG. 2 shows the concentration of materials at various time intervals.

EXAMPLES 55-63

Synthesis of Dimethyl Terephthalate (DMT)

Batch Reaction

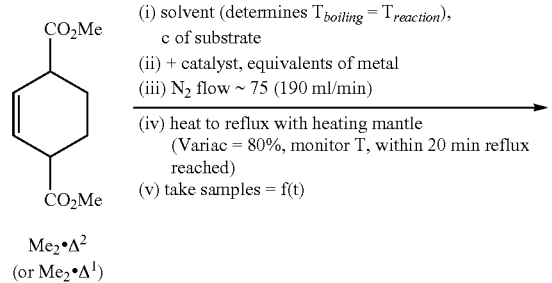

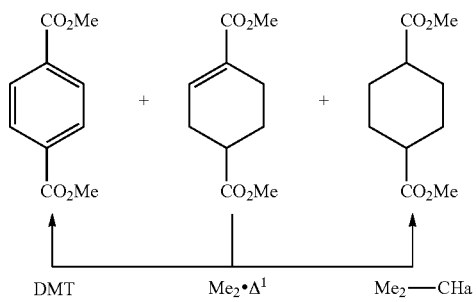

In a flask equipped with a reflux condenser, fritted gas dispersion tube, and internal T probe, a solution of dimethyl cyclohexene-1,4-carboxylate, both the 2-ene and 1-ene tautomer are starting materials, containing heterogeneous catalyst, palladium on a support, is heated to reflux under $N_2$ flow (190 ml/min) and stirring (190 rpm). Samples are taken at appropriate intervals (t=0.0, 0.25, 0.5, 1.0, 2.0, 4.0, 8.0 hours) to monitor the progress of the reactions occurring. Filtration to remove the catalyst, followed by solvent evaporation, and recrystallization of the remaining residue from methanol provides clean dimethyl terephthalate. The results are shown in Table 5.

TABLE 5

| Ex | catalyst | $T_{added}$ | $c_{substrate}$(M) | solvent | % yield after 8 h reflux | | | | $c_{DMT}/c_{CHa}$ at 8 h |
|---|---|---|---|---|---|---|---|---|---|
| | | | | | $Me_2$-$\Delta^2$ | DMT | $Me_2$-$\Delta^1$ | $Me_2$—CHa | |
| 55 | 5% Pd/C, 35 micron, JM #6 | RT | 0.2 mol % 0.18 | m-xylene | 3 | 42 | 46 | 9 | 4.5/1 |
| 56 | 5% Pd/C, 35 micron, JM #6 | RT | 0.1 mol % 0.18 | diglyme | 3 | 39 | 49 | 9 | 4.3/1 |
| 54 | 5% Pd/C, 35 micron, JM #6 | RT | 0.2 mol % 0.18 | diglyme | 0 | 77 | 5 | 17 | 4.6/1 |
| 57 | 5% Pd/C, 35 micron, JM #6 | RT | 0.4 mol % 0.18 | diglyme | 0 | 76 | 0 | 21 | 3.7/1 |
| 58 | 5% Pd/C, 35 micron, JM #6 | RT | 0.2 mol % 0.18 | $Et_2$diglyme | 3 | 24 | 66 | 7 | 3.3/1 |
| 59 | 8.6% Pd/Davisil 635, 60-100 mesh | RT | 0.3 mol % 0.22 | diglyme | 3 | 27 | 58 | 13 | 2.1/1 |
| 60 | 5% Pd/$Al_2O_3$, 50 micron, JM #12 | RT | 0.3 mol % 0.22 | diglyme | 0 | 68 | 0 | 30 | 2.3/1 |
| 61 | 5% Pd/$Al_2O_3$, 50 micron, JM #12 | reflux | 0.3 mol % 0.22 | triglyme | 0 | 75 | 0 | 23 | 3.3/1 |
| 62 | 5% Pd(S)/C, 25 micron, JM #11 | RT | 0.3 mol % 0.22 | diglyme | 0 | 73 | 0 | 25 | 2.9/1 |
| 63 | 5% Pt/C, 30 micron, JM #23 | RT | 0.3 mol % 0.22 | diglyme | 16 | 13 | 65 | 6 | 2.2/1 |

JM = Johnson-Matthey commercial catalyst screening kit.

$T_{final\ reflux}$ = 145° C. (m-xylene), 162° C. (diglyme), 190° C. ($Et_2$diglyme), and 225° C. (triglyme).

Davisil is a magnesium silica gel. Et$_2$diglyme is diethyl diglycol ether. Microns refer to the mean particle size.

EXAMPLE 64

Hydrolysis of Dimethyl Terephthalate to Terephthalic

Acid Following, U.S. Pat. No. 4,302,595, incorporated herein by reference, a suspension of dimethyl terephthalate in H$_2$O is heated to 250° C. for 4 hour in a Parr pressure reactor resulting in hydrolysis to terephthalic acid.

EXAMPLES 66 and 67

High Yield Synthesis of Dimethyl Cyclohexane-1,4-dicarboxylate

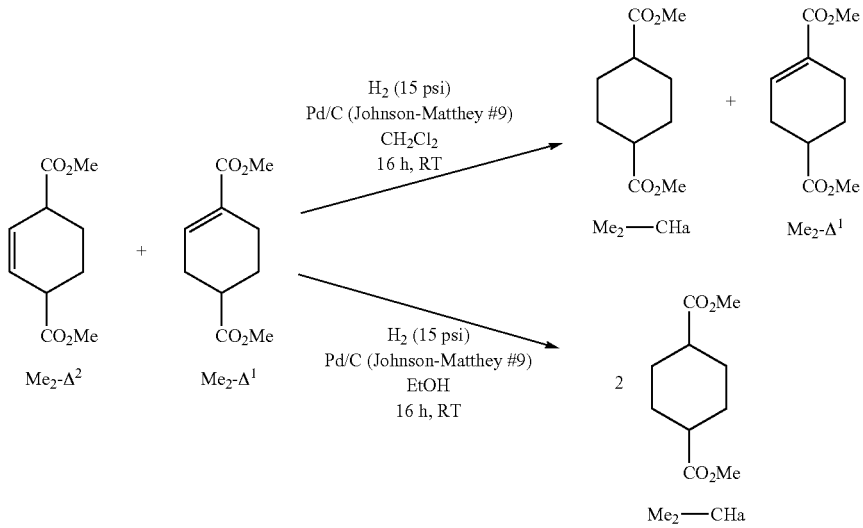

A solution of dimethyl cyclohex-2-ene-1,4-dicarboxylate and dimethyl cyclohex-1-ene-1,4-dicarboxylate is hydrogenated under balloon pressure at room temperature over Pd/C catalyst. If methylene chloride is used as the solvent, primarily the g-ene tautomer is reduced, whereas most of the 1-ene tautomer remains unreacted. If ethanol is used as the solvent both tautomers are reduced.

Substituted Diels-Alder Products and Terephthalates

EXAMPLE 68

Dimethyl 2-Chloro-cyclohexene-1,4-dicarboxylate, Dimethyl Chloro-terephthalate, and Dimethyl 2-Chloro-cyclohexane-1,4-dicarboxylate

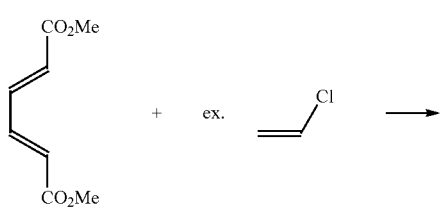

In a Parr pressure reactor, a stirred suspension of trans,trans dimethyl muconate (6.1 g, 36 mmol) in dimethyldipropyleneglycol (120 ml, 0.3 M) is heated under vinyl chloride pressure (18 psi (0.124 MPa) at 23° C.) to 165° C. for 48 hours. After cooling to room temperature, the reaction mixture is diluted using the same solvent to 200 ml in a volumetric flask, transferred into a round-bottom flask equipped with a magnetic stirring bar, and Pd/C catalyst is added (360 mg of Johnson-Matthey 5 percent Pd/C #6, 0.2 mol percent) at room temperature. The flask is equipped with a reflux condenser, fritted gas dispersion tube, and internal T probe. Under N$_2$ flow (190 ml/min) and stirring (190 rpm) the mixture is heated to reflux while samples are taken at appropriate intervals (t=0.0, 0.25, 0.5, 1.0, 2.0, 4.0, 8.0 h) to monitor the progress of the reactions occurring. After 8 hour reaction time, dimethyl chloro-terephthalate is present. Some material also undergoes C—Cl bond cleavage and dimethyl 2-chloro-cyclohexane-1,4-dicarboxylate is also formed.

EXAMPLE 69

Dimethyl 2-Methyl-cyclohexene-1,4-dicarboxylate, Dimethyl Methyl-terephthalate, and Dimethyl 2-Methyl-cyclohexane-1,4-dicarboxylate

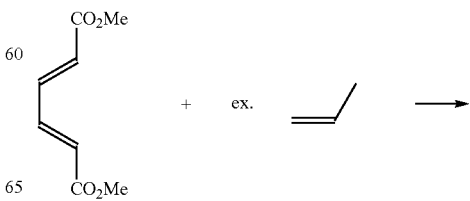

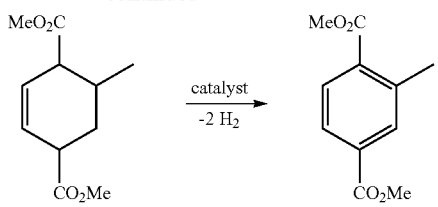

In a Parr pressure reactor, a stirred suspension of trans,trans dimethyl muconate (6.1 g, 36 mmol) in diglyme (120 ml, 0.3 M) is heated under propylene pressure (119 psi (0.0820 MPa) at 23° C.) to 165° C. for 48 hours. After cooling to room temperature, the reaction mixture is transferred to a flask and concentrated (0.5 M). Pd/C catalyst is added (0.3 mol percent of Johnson-Matthey 5 percent Pd/C #6) at room temperature. The flask is equipped with a reflux condenser, fritted gas dispersion tube, and internal Temperature probe. Under $N_2$ flow (190 ml/min) and stirring (190 rpm) the mixture is heated to reflux for 27 hours whereby dimethyl methyl-terephthalate is formed. Some dimethyl 2-methyl-cyclohexane-1,4-dicarboxylate is also produced.

EXAMPLE 70

Trimethyl Cyclohexene-1,2,4-tricarboxylate, Trimethyl Trimellitate, and Trimethyl Cyclohexane-1,2,4-tricarboxylate

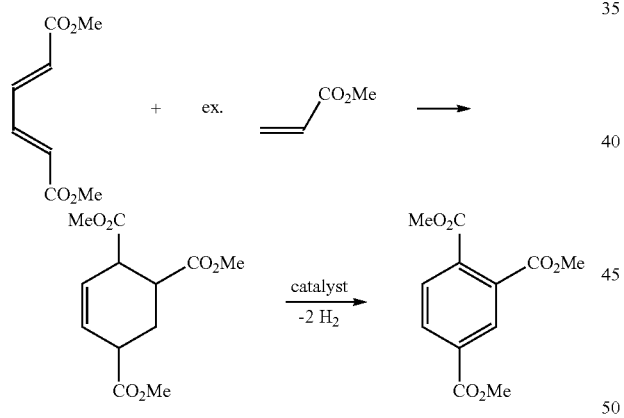

In a 75 ml sealed tube, a stirred suspension of trans,trans dimethyl muconate (10.0 g, 58.8 mmol), two equivalents of methyl acrylate (10.6 ml, 117.6 mmol), neutral $Al_2O_3$ (300 mg of Aldrich 199974, 3 mass percent), and tert-butyl catechol (25 mg, 0.2 mol percent) in diglyme (20 ml, 2.9 M) is heated to 150° C. for 24 hours. After cooling to room temperature, the reaction mixture is filtered, transferred to a flask, and concentrated (0.5 M). Pd/C catalyst is added (856 mg (0.3 mol percent) of Johnson-Matthey 5 percent Pd/C #6) at room temperature. The flask is equipped with a reflux condenser, fritted gas dispersion tube, and internal T probe. Under $N_2$ flow (190 ml/min) and stirring (190 rpm) the mixture is heated to reflux for 27 hours whereby trimethyl trimellitate (46 percent over 2 steps) is formed. Some trimethyl cyclohexane-1,2,4-tricarboxylate is also produced.

EXAMPLE 71

Dimethyl 2-Phenyl-cyclohexene-1,4-dicarboxylate, Dimethyl Phenyl-terephthalate, and Dimethyl 2-Phenyl-cyclohexane-1,4-dicarboxylate

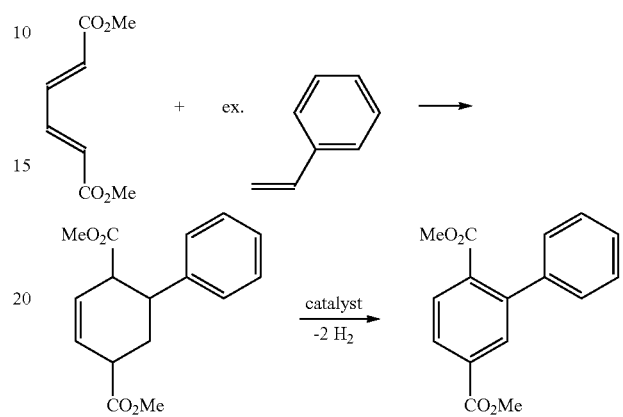

In a 75 ml sealed tube, a stirred suspension of trans,trans dimethyl muconate (10.0 g, 58.8 mmol), two equivalents of styrene (13.5 ml, 117.6 mmol), neutral $Al_2O_3$ (300 mg of Aldrich 199974, 3 mass percent), and tert-butyl catechol (25 mg, 0.2 mol percent) in diglyme (20 ml, 2.9 M) is heated to 150° C. for 24 hours. After cooling to room temperature, the reaction mixture is filtered, transferred to a flask, and concentrated. The residue is redissolved in triglyme (0.5 M). $Pd/Al_2O_3$ catalyst is added (636 mg (0.5 mol percent) of Johnson-Matthey 5 percent $Pd/Al_2O_3$ #12) at room temperature. The flask is equipped with a reflux condenser, fritted gas dispersion tube, and internal Temperature probe. Under $N_2$ flow (190 ml/min) and stirring (190 rpm) the mixture is heated to reflux for 63 hours whereby dimethyl phenyl-terephthalate is formed. Some dimethyl 2-phenyl-cyclohexane-1,4-dicarboxylate is also produced.

EXAMPLE 72

Thermal Isomerization of Cis,Trans Muconic Acid to Trans,Trans Muconic Acid

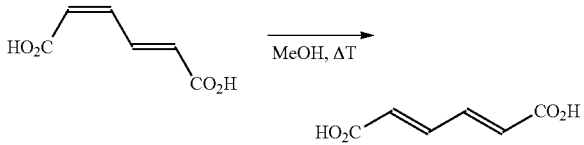

A mixture of cis,trans muconic acid (5.11 g, 36.0 mmol) and Methanol (200 ml, 0.18 M) is heated to reflux. At appropriate intervals (t=0, 2, 4, 24, 48, 72, 96, 168 hours) samples are analyzed by HPLC to determine the amounts of cis,trans muconic acid and trans,trans muconic acid being present. After 168 hours reaction time, 5.1 percent of trans,trans muconic acid are found to be present with the remaining material being unreacted cis, trans muconic acid.

EXAMPLE 73

Pd/C-catalyzed Isomerization of Cis,Trans Muconic Acid to Trans,Trans Muconic Acid

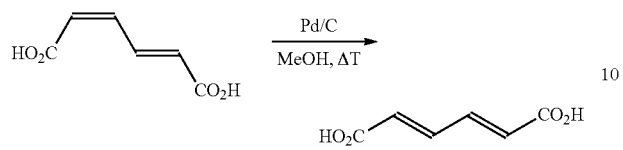

A mixture of cis,trans muconic acid (5.11 g, 36.0 mmol), Pd/C (511 mg of 5 percent Pd/C, 10 mass percent), and methanol (200 ml, 0.18 M) is heated to reflux. At appropriate intervals (t=0, 2, 4, 24, 48, 72, 96, 168 hours) samples are analyzed by HPLC to determine the amounts of cis,trans muconic acid and trans,trans muconic acid being present. After 168 hour reaction time, 22.7 percent of trans,trans muconic acid are found to be present with the remaining material being unreacted cis,trans muconic acid.

Oxidation to Esters of Trimellitic Acid

EXAMPLE 74

Preparation of Trimethyl Trimellitate

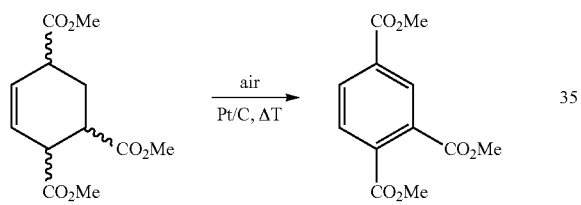

Trimethyl cyclohex-5-ene-1,2,4-tricarboxylate (200 mg, 0.78 mmol) is mixed with 305 mg of 5 percent by weight platinum on a carbon support in m-xylene (30 ml). The reaction mixture is refluxed with the reflux apparatus being open to air for 4 days. The residual platinum on carbon is then filtered off and the filtrate is concentrated down to a clear colorless gel. The desired product is obtained with a 65 percent yield. The yield is determined by GC/MS using a dodecane as an internal standard.

EXAMPLE 75

Preparation of 2-butyl-1,4-dimethyl benzene-1,2,4-tricarboxylate

Tri-n-butyl cyclohex-5-ene-1,2,4-tricarboxylate (500 mg, 1.7 mmol) is mixed with 5 percent by weight platinum on a carbon support (663 mg) in m-xylene (30 ml). The reaction mixture is refluxed with the reflux apparatus being open to air for 4 days. The residual platinum on a carbon support is then filtered off and the filtrate is concentrated down to a clear colorless gel. The resulting residue purified by column chromatography using an Analogix BSR SimpliFlash system (Hexanes/Ethyl acetate, 9:1). Due to very similar polarities between the starting material and the desired product, they cannot be completely separated. In order to determine a yield, the 2-butyl-1,4-dimethylbenzene-1,2,4-tricarboxylate undergoes a transesterification to form the trimethyl trimellitate. The transesterification does not go to completion and the yield determined by GC is 48 percent.

Reduction to Esters of Cyclohexane-1,2,4-tricarboxylic Acid

EXAMPLE 76

Preparation of Trimethyl Cyclohexane-1,2,4-tricarboxylate

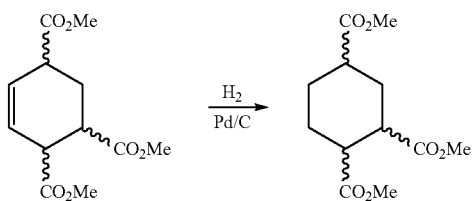 [SMILES: COC(=O)C1C=CC(C(=O)OC)C(C(=O)OC)C1 ; "H2" ; COC(=O)C1CCC(C(=O)OC)C(C(=O)OC)C1]

A solution of trimethyl cyclohex-5-ene-1,2,4-tricarboxylate (0.50 g, 1.9 mmol) in methylene chloride (15 ml) containing a catalytic amount of palladium on carbon (150 mg, 5 percent Pd/C, 7.5 mg Pd, 4 mole percent) is stirred at room temperature under balloon pressure of hydrogen gas for 2 hours, at which point GC-MS analysis shows complete conversion. Filtration and removal of the solvent provides trimethyl cyclohexane-1,2,4-tricarboxylate as a clear, colorless gel (0.42 g, 1.6 mmol, 85 percent yield).

EXAMPLE 77

Isomerization of Cis,Cis-Muconic Acid to Cis,Trans-Muconic Acid in Water

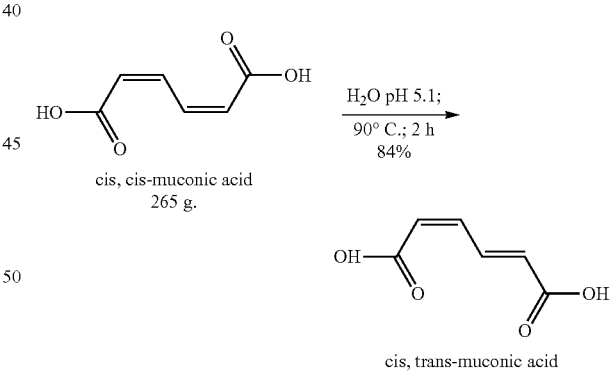

cis,cis-Muconic acid (265 g) is suspended in water (2 L) and the pH of the solution is adjusted to 5.1 with 10 M NaOH (250 mL). The mixture is heated at 90° C. for 2 hours. The progress of the isomerization is monitored by HPLC. After 2 hours of heating at 90° C., the mixture is treated with charcoal (20 g) for 30 minutes and the hot solution is filtered through a thin bed of Celite. The solution is adjusted to a pH of 2 with concentrated sulfuric acid (50 mL) and allowed to cool to 0° C. in an ice-bath. The precipitate is recovered by filtration and dried under reduced pressure overnight to yield 71 g cis,trans-muconic acid as light yellow solid. The filtrate is concentrated to 600 mL and allowed to incubate at 0° C. overnight. More precipitate is observed and is filtered and dried to yield an additional 152 g of cis,trans-muconic acid, an overall yield of 84 percent is achieved.

EXAMPLE 78

Isomerization of Cis,Trans-Muconic Acid to Trans,Trans-Conic Acid in Methanol

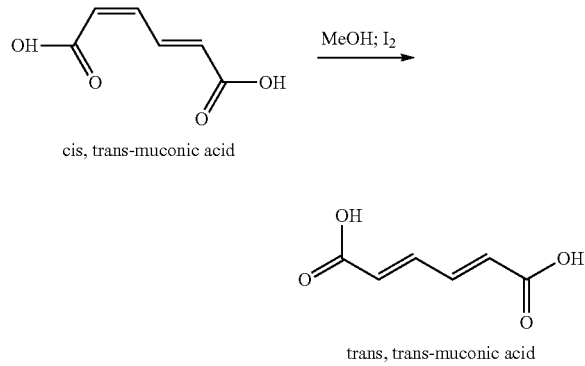

cis,trans-Muconic acid (105 mg, 0.739 mmol) is dissolved in methanol (10 mL) at room temperature and a crystal of iodine (26 mg, 0.102 mmol) is added. The reaction Mixture is allowed to stir at room temperature for 24 hours. The precipitate is filtered, washed with ice-cold acetonitrile and dried under reduced pressure to yield 65 mg of trans,trans-muconic acid, a 62 percent yield.

EXAMPLE 79

Isomerization of Cis,Trans-Muconic Acid to Trans,Trans-Muconic Acid in Ethanol

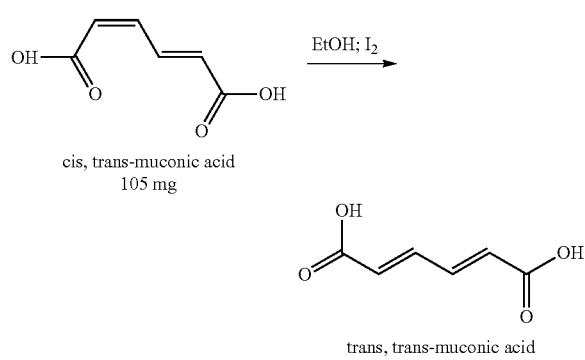

cis,trans-Muconic acid (105 mg, 0.739 mmol) is dissolved in ethanol (10 mL) at room temperature and a crystal of iodine (13 mg, 0.05 mmol) is added. The reaction mixture is allowed to stir at room temperature for 24 hour. The precipitate is filtered, washed with acetonitrile and dried under reduced pressure to yield 70 mg of trans,trans-muconic acid, a 67 percent yield.

EXAMPLE 80

Isomerization of Cis,Trans-Muconic Acid to Trans,Trans-Muconic Acid in n-Propanol

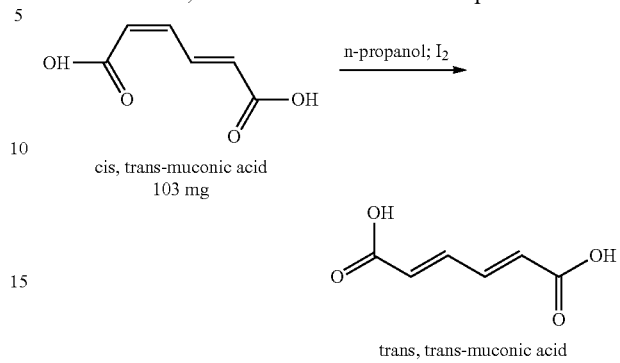

cis,trans-Muconic acid (103 mg, 0.725 mmol) is dissolved in n-propanol (10 mL) at room temperature and a crystal of iodine (10 mg, 0.04 mmol) is added. The reaction mixture is allowed to stir at room temperature for 24 hours. The precipitate is filtered, washed with acetonitrile and dried under reduced pressure to yield 75 mg of trans,trans-muconic acid, a 73 percent yield.

EXAMPLE 81

Isomerization of Cis,Trans-Muconic Acid to Trans,Trans-Muconic Acid in n-Butanol

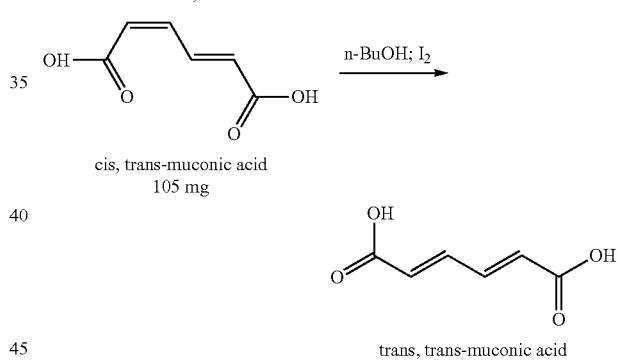

cis,trans-Muconic acid (105 mg, 0.739 mmol) is dissolved in n-butanol (10 mL) at room temperature and a crystal of iodine (17 mg, 0.067 mmol) is added. The reaction mixture is allowed to stir at room temperature for 24 hours. The precipitate is filtered, washed with ice-cold acetonitrile and dried under reduced pressure to yield 80 mg of trans,trans-muconic acid, a 76 percent yield.

EXAMPLE 82

Isomerization of Cis,Trans-Muconic Acid to Trans,Trans-Muconic Acid in Acetone

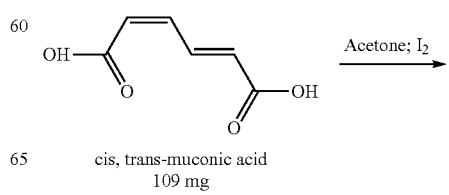

-continued

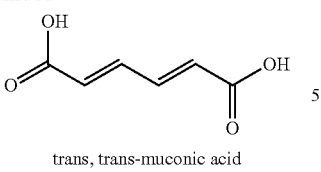
trans, trans-muconic acid cis,trans-Muconic acid (109 mg, 0.767 mmol) is dissolved in acetone (10 mL) at room temperature and a crystal of iodine (13 mg, 0.05 mmol) was added. The reaction mixture is allowed to stir at room temperature for 24 hour. The precipitate is filtered, washed with ice-cold acetonitrile and dried under reduced pressure to yield 15 mg of trans,trans-muconic acid, a 13 percent yield.

EXAMPLE 83

Isomerization of Cis,Trans-Muconic Acid to Trans,Trans-Muconic Acid in Ethyl Acetate

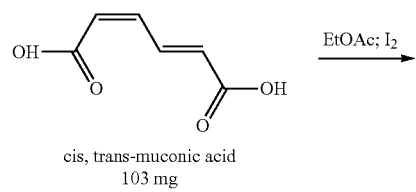
cis, trans-muconic acid
103 mg

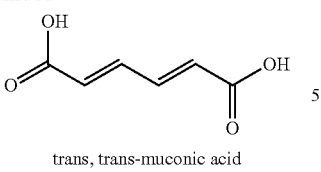
trans, trans-muconic acid cis,trans-muconic acid (103 mg, 0.767 mmol) is dissolved in ethyl acetate (10 mL) at room temperature and a crystal of iodine (27 mg, 0.106 mmol) is added. The reaction mixture is allowed to stir at room temperature for 24 hours. The precipitate is filtered, washed with ice-cold acetonitrile and dried under reduced pressure to yield 60 mg of trans,trans-muconic acid, a 58 percent yield.

EXAMPLE 84

Isomerization of Cis,Trans-Muconic Acid to Trans,Trans-Muconic Acid in Ethyl Ether

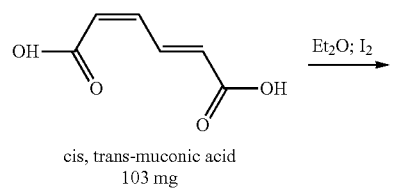
cis, trans-muconic acid
103 mg

-continued

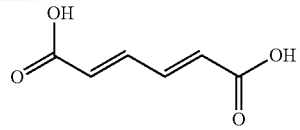
trans, trans-muconic acid cis,trans-Muconic acid (119 mg, 0.838 mmol) is dissolved in ethyl ether (10 mL) at room temperature and a crystal of iodine (7.2 mg, 0.028 mmol) is added. The reaction mixture is allowed to stir at room temperature for 24 hour. The precipitate is filtered, washed with ice-cold acetonitrile and dried under reduced pressure to yield 100 mg of trans,trans-muconic acid, a 84 percent yield.

EXAMPLE 85

Figure 3:
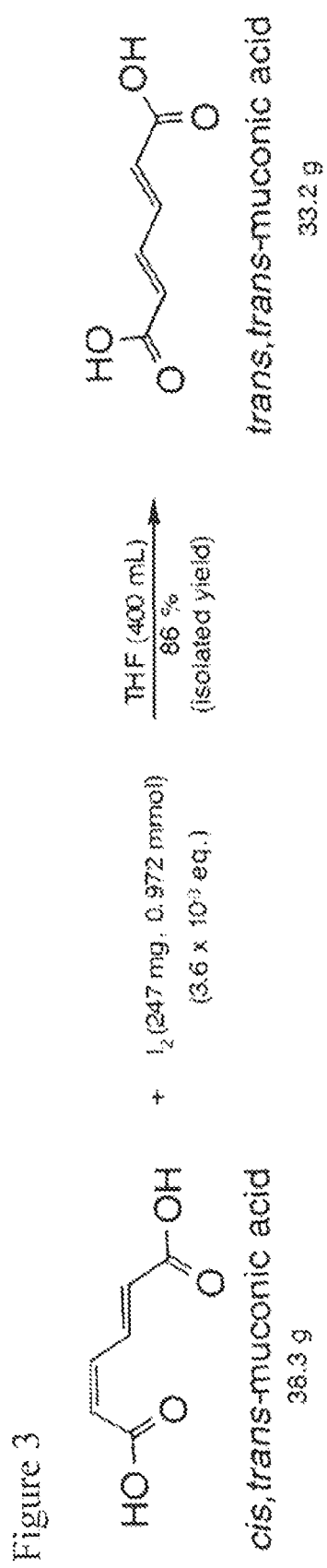
FIG. 3 shows the reaction sequence of Example 85.

Isomerization of Cis,Trans-Muconic Acid to Trans,Trans-Muconic Acid in Tetrahydrofuran cis,trans-Muconic acid (38.3 g, 269.7 mmol) is dissolved in THF (400 mL) at room temperature and a crystal of iodine (247 mg, 0.972 mmol) is added. The reaction mixture is allowed to stir at room temperature for 24 hours. The precipitate is obtained by filtration, washed with ice-cold tetrahydrofuran (2×) and dried under reduced pressure to yield 33.2 g (a 86 percent yield) of trans,trans-muconic acid. The reaction sequence is shown in FIG. 3.

EXAMPLES 86 to 90

Isomerization of Cis,Trans-Dimethyl Muconate to Trans,Trans-Dimethyl Muconate

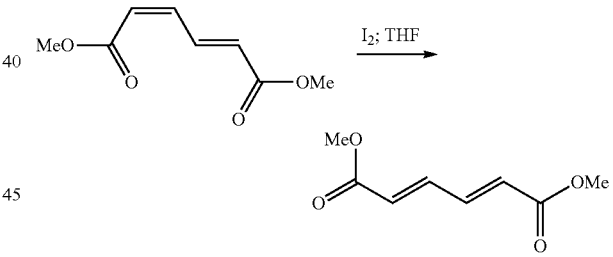

Several experiments for the isomerization of cis,trans-dimethyl muconate to trans,trans-dimethyl muconate are performed according to the following procedure. Cis,trans-dimethyl muconate is dissolved in tetrahydrofuran (50 mL) and stirred. Iodine is then added and the progress of the isomerization is monitored by HPLC. The precipitate, trans,trans-dimethyl muconate, is obtained by filtration and washed with ice-cold tetrahydrofuran. The filtrate is analyzed by HPLC to determine the total yield of the conversion. Table 6 summarizes the results obtained for this reaction.

TABLE 6

| Example | Amount Muconate g | Amount Iodine mg | Time hours | Yield percent Isolated | Yield percent Total |
| --- | --- | --- | --- | --- | --- |
| 86 | 10 | 74.7 | 3 | 88 | 97 |
| 87 | 10 | 75.3 | 5 | 54 | 75 |

TABLE 6-continued

| Example | Amount Muconate g | Amount Iodine mg | Time hours | Yield percent Isolated | Yield percent Total |
|---|---|---|---|---|---|
| 88 | 10 | 79.3 | 24 | 91 | 100 |
| 89 | 10 | 78.6 | 6 | 90 | 94 |
| 90 | 10 | 80.0 | 6 | 91 | 97 |

EXAMPLE 91

Synthesis of Cis,Trans-Dimethyl Muconate

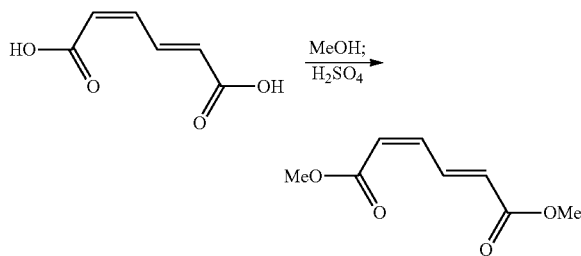

cis,trans-muconic acid (42.6 g, 0.30 mol) is dissolved in methanol (1500 mL) to which is added concentrated sulfuric acid (2 mL, 0.037 mol). The resulting solution is refluxed for 24 hours and the progress of the reaction is monitored by HPLC. Once the conversion of cis,trans-dimethyl muconate is completed as detected by HPLC, the reaction is Cooled to room temperature and concentrated until white solid began crashing out and the reaction mixture is then cooled to 0° C. overnight. The cis,trans-dimethyl muconate is obtained by filtration, washed with cold tetrahydrofuran and dried under reduced pressure to provide a total yield of 95 percent.

EXAMPLE 92

Synthesis of Dimethyl Terephthalate (DMT)-Continuous Flow Reaction

In an Autoclave Engineers BTRS-Jr continuous flow reactor, a 0.2 M solution of dimethyl cyclohexene-1,4-dicarboxylate, both the 2-ene and 1-ene tautomer are suitable substrates, is passed over hot $Pd/Al_2O_3$ [2.5 g of 5 percent $Pd/Al_2O_3$ (Johnson-Matthey #13, uniform metal location, 20 microns mean particle size, 1.23 percent $H_2O$) in a 10 ml catalyst chamber] in an up-stream flow direction under $N_2$ pressure. Selected reaction conditions are shown in the Table 7.

What is claimed is:
1. A method for preparing a compound containing a cyclohexane ring, the compound having formula (I)

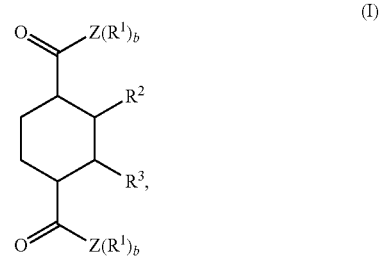

the method comprising:
(1) in a one-pot reaction, isomerizing one or more of cis,cis and cis,trans muconic acids or carboxylate derivatives thereof to form trans,trans muconic acid or carboxylate derivatives thereof, and contacting the trans,trans muconic acid or carboxylate derivatives thereof with a dienophile in a solvent under conditions such that one or more cyclohexene ring containing compounds having carboxylate groups at the 1 and 4 position are formed; and
(2) contacting the one or more cyclohexene ring containing compounds having carboxylate groups at the 1 and 4 position with hydrogen in the presence of one or more hydrogenation catalysts under conditions such that one or more compounds of formula (I) containing a cyclohexane ring having carboxylate groups at the 1 and 4 position are prepared,
wherein the cyclohexene ring containing compounds contain up to about 1 part per trillion of Carbon 14 as determined according to ASTM D6866-08, and 6 or more of the carbon atoms are derived from a muconate microbially synthesized from a biomass;
wherein said carboxylate derivatives contain group

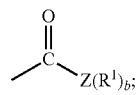

wherein:
$R^1$ is independently in each occurrence hydrogen, a hydrocarbyl group optionally containing one or more heteroatoms or a cation wherein the hydrocarbyl group or cation do not interfere in the formation of the cyclohexene ring containing compounds;

TABLE 7

| Sample | t (h) | Flow rate (ml/min) | P $N_2$, psi (MPa) | T ° C. | % Yield $Me_2$-$\Delta^2$ | % Yield DMT | % Yield $Me_2$-$\Delta^1$ | % Yield Me—CHa | ratio $C_{DMT}/C_{CHa}$ at 8 h |
|---|---|---|---|---|---|---|---|---|---|
| 1 | 0 | 0.2 | 15 (0.103) | 23 | 88 | 0 | 12 | 0 | — |
| 2 | 5 | 0.2 | 200 (0.138) | 300 | 0 | 80 | 10 | 10 | 8/1 |
| 3 | 6 | 0.2 | 200 (0.138) | 300 | 0 | 84 | 7 | 9 | 13/1 |
| 4 | 7 | 1.0 | 365 (2.52) | 365 | 0 | 82 | 5 | 12 | 7/1 |
| 5 | 7.5 | 1.0 | 250 (1.72) | 365 | 0 | 86 | 6 | 9 | 10/1 |

$C_{DMT}/C_{CHa}$ is the mole ratio of Dimethyl Terephthalate to the 1,4-di(methylcarboxylate) cyclohexane R² is independently in each occurrence hydrogen or a hydrocarbyl group optionally containing a heteroatom containing functional group wherein the hydrocarbyl group does not interfere in the formation of the cyclohexene ring containing compounds; and R³ is independently in each occurrence hydrogen or a hydrocarbyl group optionally containing a heteroatom containing functional group wherein the hydrocarbyl group does not interfere in the formation of the cyclohexene ring containing compounds;

or R² and R³ combine to form a cyclic ring that can contain heteroatoms;

Z is independently in each occurrence an anion, oxygen, nitrogen, sulfur, nitrile or a halogen; and b is independently in each occurrence 0, 1 or 2 with the proviso that b is 0 when Z is an anion, halogen or nitrile; b is 1 when Z is oxygen or sulfur; and b is 2 when Z is nitrogen.

2. A method according to claim 1 wherein the one or more hydrogenation catalysts include one or more metals.

3. A method according to claim 1 wherein the cyclohexene ring containing compounds having carboxylate groups at the 1 and 4 position are contacted with hydrogen at ambient temperatures.

4. A method according to claim 1 wherein the cyclohexene ring containing compounds are contacted with hydrogen while being refluxed in one or more solvents.

5. A method according to claim 1 wherein the one or more hydrogenation catalysts contains one or more of nickel, platinum or palladium.

6. A method according to claim 1 wherein the contacting in step (2) occurs at a pressure from about 14.7 psi to about 200 psi.

7. A method according to claim 1 wherein the one or more cyclohexene ring containing compounds correspond to one or more of the following formulas:

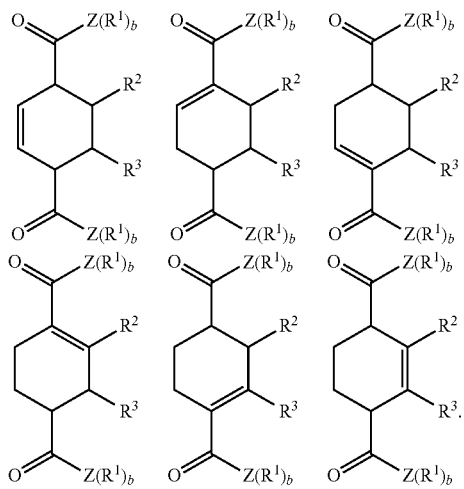

8. A method according to claims 1, further comprising producing one or more precursors to the one or more of cis, cis and cis,trans muconic acids or carboxylate derivatives thereof in a microbial synthesis based fermenter under controlled conditions from the biomass.

9. A method according to claim 1 wherein in step (1), the dienophile comprises one or more unsaturated cyclic compounds, one or more unsaturated esters or aromatic compounds having at least one unsaturated substituent.

10. A method according to claim 1 wherein in step (1), the isomerizing includes contacting the one or more of cis, cis and cis,trans muconic acids or carboxylate derivatives thereof, with one or more isomerization catalysts, or a source of ultraviolet radiation, or both, such that the one or more of cis, cis and cis,trans muconic acids or carboxylate derivatives thereof, isomerize to the trans,trans muconic acid or carboxylate derivatives thereof.

11. A method according to claim 1 wherein the trans,trans muconic acid carboxylate derivatives are esters of muconic acid and wherein the one or more cyclohexene ring containing compounds have alkyl carboxylate groups at the 1 and 4 positions and are prepared by a) in said one-pot reaction, contacting the cis, cis or cis, trans muconic acid and one or more isomerization catalysts, or a source of ultraviolet radiation, or both, such that the cis,cis or cis,trans muconic acid isomerizes to the trans, trans muconic acid, and contacting the trans, trans muconic acid with the dienophile to form one or more cyclohexene compounds having carboxylic acid groups at the 1 and 4 positions;

b) removing the solvent; and c) contacting the one or more cyclohexene compounds having carboxylic acid groups at the 1 and 4 positions with one or more esterifying agents in the presence of one or more strong acids under conditions that one or more cyclohexene ring containing compounds having alkyl carboxylate groups at the 1 and 4 positions are formed.

12. A method according to claim 1, further comprising contacting the one or more compounds of formula (I) containing the cyclohexane ring having carboxylate groups at the 1 and 4 position with an acid such that the carboxylate groups are converted to methylol groups.

13. A method according to claim 1, wherein Z is oxygen and the compound containing the cyclohexane ring corresponds to formula (II):

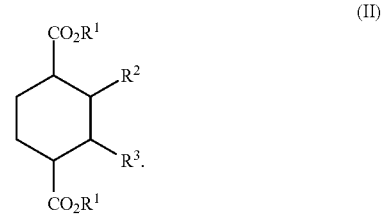

14. A method according to claim 13 wherein the compound containing the cyclohexane ring corresponds to one of the following formulas:

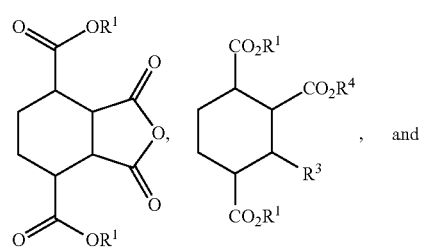

-continued

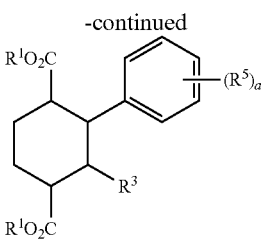

wherein:
R[4] is independently in each occurrence hydrogen, a hydrocarbyl group optionally containing a heteroatom containing functional group;
R[5] is independently in each occurrence a hydrocarbyl group optionally containing a heteroatom containing functional group; and
a is independently in each occurrence an integer of from 0 to 5.

15. A method according to claim 13 wherein $R^2$ is independently in each occurrence selected from chloro, bromo, $C_{1-8}$ alkyl, phenyl, or $C_{1-8}$ alkyl carboxylate, and $R^3$ is hydrogen.

16. A method according to claim 13 wherein $R^2$ is independently in each occurrence chloro, methyl, ethyl or phenyl, and $R^3$ is hydrogen.

17. A method according to claim 1 wherein the biomass includes a carbohydrate.

18. A method for preparing a compound containing a cyclohexane ring, the compound having formula (I)

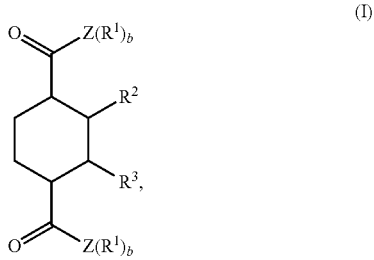

(I)

the method comprising:
contacting one or more cyclohexene ring containing compounds having carboxylate groups at the 1 and 4 position with hydrogen in the presence of one or more hydrogenation catalysts under conditions such that one or more compounds of formula (I) containing a cyclohexane ring having carboxylate groups at the 1 and 4 position are prepared;
wherein said carboxylate derivatives contain group

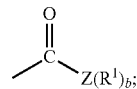

wherein the cyclohexene compounds are derived from muconic acid prepared by microbial synthesis, in a one-pot reaction of (1) isomerizing one or more of cis,cis and cis,trans muconic acids prepared from said microbial synthesis, or carboxylate derivatives thereof, to form trans, trans muconic acid or carboxylate derivatives thereof, and (2) contacting the trans, trans muconic acid or carboxylate derivatives thereof with a dienophile under conditions such that the one or more cyclohexene compounds are formed;
wherein
$R^1$ is independently in each occurrence hydrogen, a hydrocarbyl group optionally containing one or more heteroatoms or a cation wherein the hydrocarbyl group or cation do not interfere in the formation of the cyclohexene ring containing compounds;
$R^2$ is independently in each occurrence hydrogen or a hydrocarbyl group optionally containing a heteroatom containing functional group wherein the hydrocarbyl group does not interfere in the formation of the cyclohexene ring containing compounds; and
$R^3$ is independently in each occurrence hydrogen or a hydrocarbyl group optionally containing a heteroatom containing functional group wherein the hydrocarbyl group does not interfere in the formation of the cyclohexene ring containing compounds;
or $R^2$ and $R^3$ combine to form a cyclic ring that can contain heteroatoms;
Z is independently in each occurrence an anion, oxygen, nitrogen, sulfur, nitrile or a halogen; and
b is independently in each occurrence 0, 1 or 2 with the proviso that b is 0 when Z is an anion, halogen or nitrile; b is 1 when Z is oxygen or sulfur; and b is 2 when Z is nitrogen.

19. A method according to claim 18 wherein the muconic acid is prepared by microbial synthesis from a biomass.

* * * * *